United States Patent
Boyd et al.

(10) Patent No.: US 9,133,157 B2
(45) Date of Patent: Sep. 15, 2015

(54) HIV PROTEASE INHIBITORS

(71) Applicants: Michael John Boyd, Winchester, MA (US); Jean-Francois Chiasson, St-Constant (CA); Sheldon Crane, Pierrefonds (CA); André Giroux, Ste-Anne-de-Bellevue (CA)

(72) Inventors: Michael John Boyd, Winchester, MA (US); Jean-Francois Chiasson, St-Constant (CA); Sheldon Crane, Pierrefonds (CA); André Giroux, Ste-Anne-de-Bellevue (CA)

(73) Assignee: Merck Canada Inc., Kirkland, Province of Quebec (CA)

( * ) Notice: Subject to any disclaimer, the term of this patent is extended or adjusted under 35 U.S.C. 154(b) by 0 days.

(21) Appl. No.: 14/353,865

(22) PCT Filed: Oct. 26, 2012

(86) PCT No.: PCT/CA2012/000998
§ 371 (c)(1),
(2) Date: Apr. 24, 2014

(87) PCT Pub. No.: WO2013/059928
PCT Pub. Date: May 2, 2013

(65) Prior Publication Data
US 2014/0303171 A1    Oct. 9, 2014

Related U.S. Application Data

(60) Provisional application No. 61/551,774, filed on Oct. 26, 2011.

(51) Int. Cl.
| | | |
|---|---|---|
| *A61K 31/381* | (2006.01) | |
| *C07D 333/10* | (2006.01) | |
| *C07D 333/20* | (2006.01) | |
| *C07D 409/12* | (2006.01) | |
| *C07D 413/12* | (2006.01) | |
| *C07D 417/12* | (2006.01) | |
| *C07D 417/14* | (2006.01) | |
| *C07D 471/04* | (2006.01) | |
| *C07D 487/04* | (2006.01) | |
| *C07D 277/28* | (2006.01) | |
| *C07B 59/00* | (2006.01) | |

(52) U.S. Cl.
CPC ............ *C07D 333/20* (2013.01); *C07B 59/002* (2013.01); *C07D 277/28* (2013.01); *C07D 409/12* (2013.01); *C07D 413/12* (2013.01); *C07D 417/12* (2013.01); *C07D 417/14* (2013.01); *C07D 471/04* (2013.01); *C07D 487/04* (2013.01)

(58) Field of Classification Search
USPC ..................... 514/438, 365; 549/77; 548/204
See application file for complete search history.

(56) References Cited

U.S. PATENT DOCUMENTS

| | | | |
|---|---|---|---|
| 7,388,008 | B2 | 6/2008 | Stranix et al. |
| 8,497,383 | B2 | 7/2013 | Coburn et al. |

FOREIGN PATENT DOCUMENTS

| | | | |
|---|---|---|---|
| WO | 0168593 | A2 | 9/2001 |
| WO | 02064551 | A1 | 8/2002 |
| WO | 03074467 | A2 | 9/2003 |
| WO | 2004056764 | A1 | 7/2004 |
| WO | 2006012725 | A1 | 2/2006 |
| WO | 2006114001 | A1 | 11/2006 |
| WO | 2008023273 | A2 | 2/2008 |
| WO | 2008078200 | A2 | 7/2008 |
| WO | 2009042093 | A1 | 4/2009 |
| WO | 2009042094 | A2 | 4/2009 |
| WO | 2010138338 | A1 | 12/2010 |
| WO | 2012055031 | A1 | 5/2012 |
| WO | 2012055034 | A1 | 5/2012 |

*Primary Examiner* — Charanjit Aulakh
(74) *Attorney, Agent, or Firm* — Carol S. Quagliato; Laura M. Ginkel

(57) ABSTRACT

Compounds of Formula I are disclosed: wherein A, $R^1$, $R^2$, $R^3$, $R^{4A}$, $R^{4B}$, $R^5$, $R^6$ and $R^7$ are defined herein. The compounds encompassed by Formula I include compounds which are HIV protease inhibitors. The compounds and their pharmaceutically acceptable salts are useful for the prophylaxis or treatment of infection by HIV and the prophylaxis, treatment, or delay in the onset of AIDS. The compounds and their salts can be employed as ingredients in pharmaceutical compositions, optionally in combination with other antivirals, immunomodulators, antibiotics or vaccines.

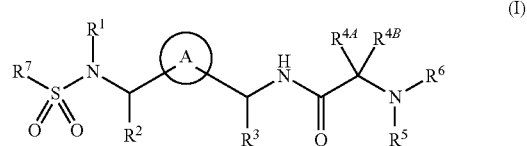

(I)

24 Claims, No Drawings

SEQUENCE LISTING

<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: HIV-1 Protease Peptide
<220> FEATURE:
<221> NAME/KEY: MISC_FEATURE
<223> OTHER INFORMATION: Xaa = betanaphthyl alanine
<220> FEATURE:
<221> NAME/KEY: misc_feature
<222> LOCATION: (5)..(5)
<223> OTHER INFORMATION: Xaa can be any naturally occurring amino acid

<400> SEQUENCE: 1

Val Ser Gln Asn Xaa Pro Ile Val
1               5

HIV PROTEASE INHIBITORS

RELATED APPLICATIONS

This application is a 35 U.S.C. §371 filing from International Application No. PCT/CA2012/000998, filed Oct. 26, 2012, which claims the benefit of U.S. Provisional Application No. 61/551,774, filed Oct. 26, 2011. Each of the aforementioned applications is herein incorporated by reference in its entirety.

REFERENCE TO SEQUENCE LISTING SUBMITTED ELECTRONICALLY

The sequence listing of the present application is submitted electronically via EFS-Web as an ASCII formatted sequence listing with a file name "MRLIFD00037USPCT-SEQTXT-2014APR17.txt", having a creation date of Apr. 17, 2014, and a size of 780 bytes, 4.00 KB. This sequence listing submitted via EFS-Web is part of the specification and is herein incorporated by reference in its entirety.

FIELD OF THE INVENTION

The present invention is directed to HIV protease inhibitors and their pharmaceutically acceptable salts. The compounds are useful for the prophylaxis of HIV infection and HIV replication, the treatment of HIV infection and HIV replication, the prophylaxis of AIDS, the treatment of AIDS, and the delay in the onset and/or progression of AIDS.

BACKGROUND OF THE INVENTION

A retrovirus designated human immunodeficiency virus (HIV), particularly the strains known as HIV type-1 (HIV-1) virus and type-2 (HIV-2) virus, is the etiological agent of acquired immunodeficiency syndrome (AIDS), a disease characterized by the destruction of the immune system, particularly of CD4 T-cells, with attendant susceptibility to opportunistic infections, and its precursor AIDS-related complex ("ARC"), a syndrome characterized by symptoms such as persistent generalized lymphadenopathy, fever and weight loss. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl et al., 1988, Proc. Natl. Acad. Sci. USA 85:4686, demonstrated that genetic inactivation of the HIV encoded protease resulted in the production of immature, non-infectious virus particles. These results indicated that inhibition of the HIV protease represents a viable method for the treatment of AIDS and the prevention or treatment of infection by HIV.

Nucleotide sequencing of HIV shows the presence of a pol gene in one open reading frame. See Ratner et al., 1985, Nature 313:277. Amino acid sequence homology provides evidence that the pol sequence encodes reverse transcriptase, an endonuclease, HIV protease and gag, which encodes the core proteins of the virion. See Toh et al., 1985, EMBO J. 4:1267; Power et al., 1986, Science 231:1567; Pearl et al., 1987, Nature 329:351.

Several HIV protease inhibitors are presently approved for clinical use in the treatment of AIDS and HIV infection, including indinavir (see U.S. Pat. No. 5,413,999), amprenavir (U.S. Pat. No. 5,585,397), saquinavir (U.S. Pat. No. 5,196,438), ritonavir (U.S. Pat. No. 5,484,801), nelfinavir (U.S. Pat. No. 5,484,926), and atazanavir (U.S. Pat. No. 5,849,911 and U.S. Pat. No. 6,087,383). Each of these protease inhibitors is a peptide-derived peptidomimetic, competitive inhibitor of the viral protease which prevents cleavage of the HIV gag-pol polyprotein precursor. Tipranavir (U.S. Pat. No. 5,852,195) is a non-peptide peptidomimetic protease inhibitors also approved for use in treating HIV infection. The protease inhibitors are administered in combination with at least one and typically at least two other HIV antiviral agents, particularly nucleoside reverse transcriptase inhibitors such as zidovudine (AZT) and lamivudine (3TC) and/or non-nucleoside reverse transcriptase inhibitors such as efavirenz and nevirapine. Indinavir, for example, has been found to be highly effective in reducing HIV viral loads and increasing CD4 cell counts in HIV-infected patients, when used in combination with nucleoside reverse transcriptase inhibitors. See, for example, Hammer et al., 1997, New England J. Med. 337:725-733 and Gulick et al., 1997, New England J. Med. 337:734-739.

The established therapies employing a protease inhibitor are not suitable for use in all HIV-infected subjects. Some subjects, for example, cannot tolerate these therapies due to adverse effects. Many HIV-infected subjects often develop resistance to particular protease inhibitors. Accordingly, there is a continuing need for new compounds which are capable of inhibiting HIV protease and suitable for use in the treatment or prophylaxis of infection by HIV and/or for the treatment or prophylaxis or delay in the onset or progression of AIDS.

Of interest as background are the following references which disclose amino acid derivatives with HIV aspartyl protease inhibiting properties, processes for preparing the derivatives, and/or therapeutic uses of the derivatives: International Patent Publication Nos. WO 01/68593, WO 02/064551 A1, WO 03/074467 A2, WO 2004/056764 A1, WO 2006/012725 A1, WO 2006/114001 A1, WO 2007/062526 A1, WO 2008/023273 A2, WO 2008/078200 A2, WO 2010/138338 A1, and U.S. Pat. No. 7,388,008 B2.

Also of interest is WO 2009/042093 which discloses certain lysine sulfonamide derivatives some of which are HIV protease inhibitors and others of which can be metabolized in vivo to HIV protease inhibitors. Many of the derivatives are characterized by the inclusion of branching on the lysine side chain.

SUMMARY OF THE INVENTION

The present invention is directed to certain compounds and their use in the inhibition of HIV protease, the prophylaxis of infection by HIV, the treatment of infection by HIV, and the prophylaxis, treatment, and delay in the onset or progression of AIDS. More particularly, the present invention includes compounds of Formula I:

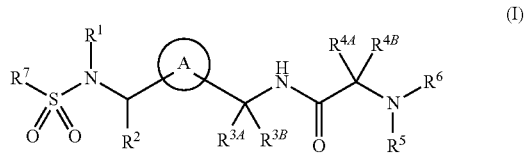

or a pharmaceutically acceptable salt thereof, wherein:
$R^1$ is H, $C_{1-6}$ alkyl, $C_{1-6}$ fluoroalkyl, CycA, AryA, HetA, $C_{1-6}$ alkyl substituted with CycA, $C_{1-6}$ alkyl substituted with AryA, or $C_{1-6}$ alkyl substituted with HetA;

$R^2$ is $C_{1-6}$alkyl-OH;
Ring A is:

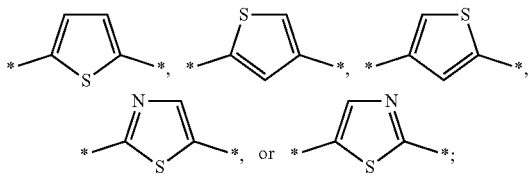

wherein the asterisks (*) denote the points of attachment to the rest of the compound;
$R^{3A}$ is H, $C_{1-6}$ alkyl, $C_{1-6}$ haloalkyl, or CycB;
$R^{3B}$ is H or $C_{1-6}$ alkyl;
$R^{4A}$ is:

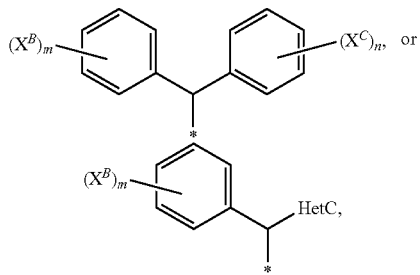

wherein the asterisk (*) denotes the point of attachment to the rest of the compound;
$R^{4B}$ is H or $C_{1-6}$ alkyl;
each $X^B$ and each $X^C$ are independently halo;
m is an integer equal to 0 or 1;
n is an integer equal to 0 or 1;
$R^5$ is $C(O)-R^K$;
$R^K$ is $O-C_{1-6}$ alkyl or AryC;
$R^6$ is H or $C^{1-6}$ alkyl;
$R^7$ is AryQ, HetQ, or HetQ';
AryQ is an aryl which is independently phenyl, naphthyl, tetrahydronaphthyl, indenyl, or dihydroindenyl, wherein the aryl is optionally substituted with from 1 to 3 $X^A$ each of which is independently:
(1) $C_{1-6}$ haloalkyl,
(2) OH
(3) halo,
(4) $NH_2$,
(5) $N(H)C(O)O-C_{1-6}$ alkyl,
(6) $C(O)-C_{1-6}$ alkyl,
(7) $C(O)NH_2$,
(8) $C_{1-6}$ alkyl substituted with:
  (a) OH,
  (b) $NH_2$, or
  (c) CH(O),
(9) $C_{1-6}$ haloalkyl substituted with OH,
(10) HetD
(11) C(O)-HetD, or
(12) $C_{1-6}$ alkyl substituted with HetD; with the proviso that no more than 2 $X^A$ are HetD, C(O)-HetD or $C_{1-6}$ alkyl substituted with HetD;
HetQ is a heteroaryl which is independently (i) a 5- or 6-membered heteroaromatic ring containing from 1 to 4 heteroatoms independently selected from N, O and S, wherein each N is optionally in the form of an oxide or (ii) a 9- or 10-membered bicyclic, fused ring system containing from 1 to 3 heteroatoms independently selected from N, O and S, and wherein at least one of the rings is aromatic, each N in a ring is optionally in the form of an oxide, and each S is optionally S(O) or $S(O)_2$; and wherein the heteroaryl is optionally substituted with from 1 to 3 substituents selected from halo, $NH_2$ and $O-C_{1-6}$ alkyl;
HetQ' is independently a dihydro derivative of the heteroaryl defined in HetQ wherein the dihydro derivative is not or does not contain an aromatic ring; and wherein the derivative is optionally substituted with from 1 to 3 oxo substituents;
CycA is a $C_{3-7}$ cycloalkyl which is optionally substituted with from 1 to 3 halo substituents;
CycB is a $C_{3-7}$ cycloalkyl which is optionally substituted with from 1 to 3 substituents each of which is independently halo or $C_{1-6}$ alkyl;
AryA is an aryl which is independently phenyl or naphthyl, wherein the phenyl or naphthyl is optionally substituted with from 1 to 3 halo substituents;
AryC is an aryl which is independently phenyl or naphthyl, wherein the phenyl or naphthyl is optionally substituted with from 1 to 3 halo substituents;
HetA is a heteroaryl which is independently (i) a 5- or 6-membered heteroaromatic ring containing from 1 to 3 heteroatoms independently selected from N, O and S, or (ii) is a fused, 9- or 10-membered heterobicyclic ring containing from 1 to 3 heteroatoms independently selected from N, O and S, and wherein at least one of the rings is aromatic, each N in a ring is optionally in the form of an oxide, and each S is optionally S(O) or $S(O)_2$; wherein the heteroaromatic ring (i) or the heterobicyclic ring (ii) is optionally substituted with from 1 to 3 YC wherein each YC independently
(1) $C_{1-6}$ alkyl,
(2) $O-C_{1-6}$ alkyl, or
(3) $SO_2-N(C_{1-6}$ alkyl$)_2$;
HetC is a heteroaryl which is independently (i) a 5- or 6-membered heteroaromatic ring containing from 1 to 3 heteroatoms independently selected from N, O and S, or (ii) is a fused, 9- or 10-membered heterobicyclic ring containing from 1 to 3 heteroatoms independently selected from N, O and S, and wherein at least one of the rings is aromatic, each N in a ring is optionally in the form of an oxide, and each S is optionally S(O) or $S(O)_2$; wherein the heteroaromatic ring (i) or the heterobicyclic ring (ii) is optionally substituted with from 1 to 3 $Y^D$ wherein each $Y^D$ independently is $C_{1-6}$alkyl or phenyl; and
each HetD is independently a 5- or 6-membered heteroaromatic ring containing from 1 to 4 heteroatoms independently selected from N, O and S, wherein the heteroaromatic ring is optionally substituted with from 1 to 3 substituents each of which is independently $C_{1-6}$ alkyl.

The present invention also includes pharmaceutical compositions containing a compound of Formula I or a pharmaceutically acceptable salt thereof. The present invention further includes methods involving compounds of Formula I for the treatment of AIDS, the delay in the onset or progression of AIDS, the prophylaxis of AIDS, the prophylaxis of infection by HIV, and the treatment of infection by HIV.

Other embodiments, aspects and features of the present invention are either further described in or will be apparent from the ensuing description, examples and appended claims.

DETAILED DESCRIPTION OF THE INVENTION

The present invention includes, as a first embodiment, compounds of Formula I above and pharmaceutically acceptable salts thereof. The compounds encompassed by Formula I are HIV protease inhibitors.

A second embodiment of the present invention is a compound of Formula I, or a pharmaceutically acceptable salt thereof, wherein Ring A is:

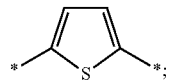

wherein the left asterisk (*) denotes the point of attachment to the left-most moiety in the rest of the compound, and the right asterisk (*) denotes the point of attachment to the right-most moiety in the rest of the compound; and all other variables are as defined in the first embodiment.

A third embodiment of the present invention is a compound of Formula I, or a pharmaceutically acceptable salt thereof, wherein $R^1$ is H, $C_{1-6}$ alkyl, $C_{1-6}$ fluoroalkyl, $(CH_2)_{1-2}CycA$, $(CH_2)_{1-2}$-HetA, or $(CH_2)_{1-2}AryA$ and all other variables are as defined in the first or second embodiment. In one aspect of this embodiment, CycA is cyclopropyl or cyclobutyl, wherein the cycloalkyl is optionally substituted with 1 or 2 fluoro substituents; HetA is a heteroaryl selected from the group consisting of pyrazolyl, oxadiazolyl, pyridinyl, indolyl, and pyrrolopyridinyl; wherein the heteroaryl is optionally substituted with 1 substituent which is $C_{1-6}$ alkyl, O—$C_{1-6}$ alkyl, or $SO_2$—$N(C_{1-6}$ alkyl$)_2$; and AryA is phenyl. In another aspect of this embodiment, $R^1$ is:

(1) H, (2) $CH_2CH_3$, (3) $CH(CH_3)_2$, (4) $CH(CD_3)_2$, (5) $CD(CD_3)_2$, (6) $CH_2CH_2CH_2CH_3$, (7) $CH_2CH(CH_3)_2$, (8) $CH_2CH_2CH(CH_3)_2$, (9) $CH_2CH_2C(CH_3)_3$,

(10) $CH_2CH_2CF_3$,

(11) $CH_2CH_2CH_2CF_3$,

(12) 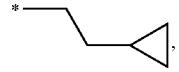

(13) 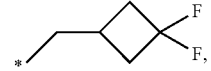

(14) 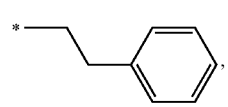

(15) 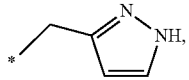

optionally substituted with 1 substituent which is $SO_2N(CH_3)_2$,

(16) 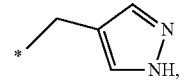

(17) 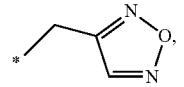

optionally mono-substituted with $CH_3$,

(18) 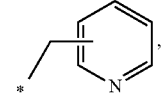

optionally substituted with 1 substituents which is $OCH_3$,

(19) 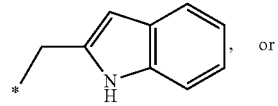, or

(20) 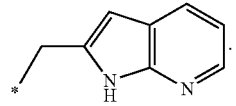.

A fourth embodiment of the present invention is a compound of Formula I, or a pharmaceutically acceptable salt thereof, wherein $R^2$ is $CH_2OH$, and all other variables are as defined in any of the first through third embodiments.

A fifth embodiment of the present invention is a compound of Formula I, or a pharmaceutically acceptable salt thereof, wherein $R^{3A}$ is H, $CH_3$, $CH_2CH_3$, $CF_3$, or cyclopropyl; and $R^{3B}$ is H or $CH_3$, and all other variables are as defined in any of the first through fourth embodiments. In one aspect of this embodiment, $R^{3A}$ is H, $CH_3$, or $CF_3$; and $R^{3B}$ is H.

A sixth embodiment of the present invention is a compound of Formula I, or a pharmaceutically acceptable salt thereof, wherein $R^{4A}$ is:

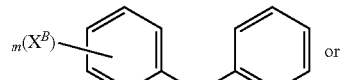 or

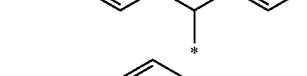

$R^{4B}$ is H, and all other variables are as defined in any of the first through fifth embodiments. In one aspect of this embodiment, HetC is a heteroaryl which is independently (i) a 5- or 6-membered heteroaromatic ring containing from 1 to 3 N atoms or (ii) a fused, 9- or 10-membered heterobicyclic ring containing from 1 to 3 N atoms, and wherein at least one of the rings is aromatic and each N is optionally in the form of an oxide; wherein the heteroaryl is optionally substituted with from 1 to 3 $Y^D$ wherein each $Y^D$ is independently $C_{1-3}$ alkyl or phenyl; and $X^B$ is fluoro. In one subaspect of this aspect, HetC is a heteroaryl which is:

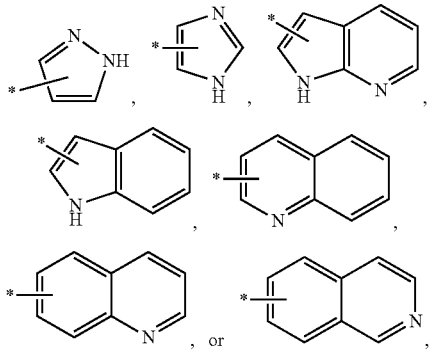

wherein the heteroaryl is optionally substituted with from 1 to 3 $Y^D$ wherein each $Y^D$ is independently $CH_3$ or phenyl. In another aspect of this embodiment, $R^{4A}$ is:

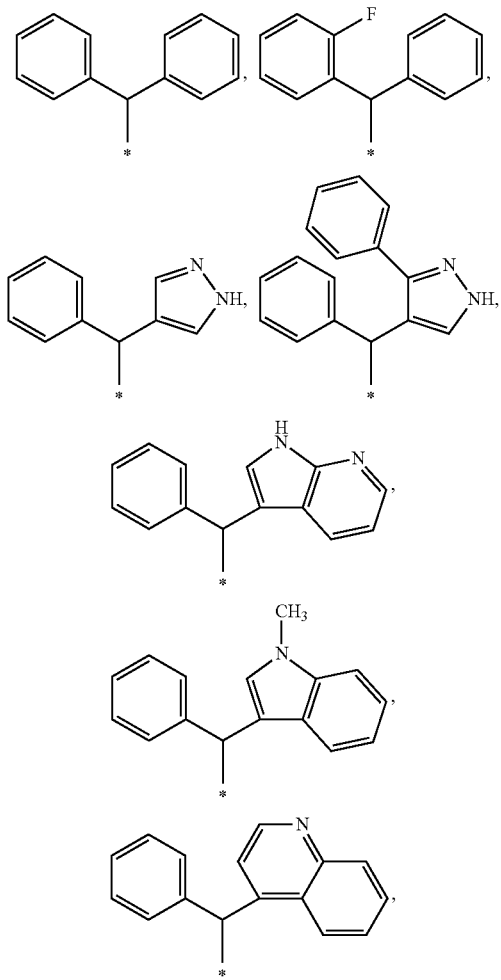

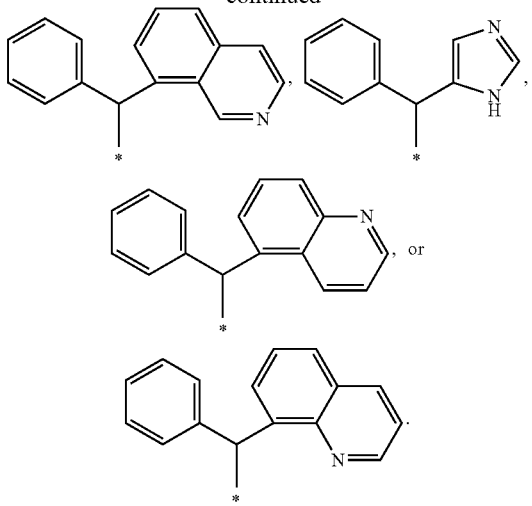

A seventh embodiment of the present invention is a compound of Formula I, or a pharmaceutically acceptable salt thereof, wherein $R^5$ is $C(O)OCH_3$ or $C(O)$-phenyl, and all other variables are as defined in any of the first through sixth embodiments.

An eighth embodiment of the present invention is a compound of Formula I, or a pharmaceutically acceptable salt thereof, wherein AryQ in $R^7$ is phenyl or dihydroindenyl, either of which is optionally substituted with from 1 to 3×A, each of which is independently:
(1) OH,
(2) Cl,
(3) F,
(4) $NH_2$,
(5) $N(H)C(O)O$—$C_{1-4}$ alkyl,
(6) $C(O)$—$C_{1-4}$ alkyl,
(7) $C_{1-4}$ alkyl substituted with
   (a) OH,
   (b) $NH_2$,
(8) $C_{1-4}$ fluoroalkyl substituted with OH,
(9) HetD
(10) $C(O)$—HetD, or
(11) $CH_2$-HetD;
   with the proviso that no more than 2 $X^A$ are HetD, $C(O)$—HetD or $CH_2$-HetD; and wherein HetD is a heteroaromatic ring which is oxazolyl, isoxazolyl, pyrazolyl, triazolyl, tetrazolyl, or pyridinyl, wherein the heteroaromatic ring is optionally substituted with from 1 to 3 substituents which are $C_{1-4}$ alkyl;

HetQ in $R^7$ is a heteroaryl which is thiophenyl (also referred to as thienyl), imidazolyl, pyridinyl, imidazopyridinyl, imidazopyrazinyl, triazolopyridinyl, triazolopyrazinyl, benzoimidazolyl, benzothiophenyl (also referred to as benzothienyl), benzothiadiazolyl, benzotriazolyl, quinolinyl, benzoxazolyl, benzothiazolyl, indolyl, or indazolyl; wherein the heteroaryl is optionally substituted with from 1 to 3 substituents which are $C_1$, $NH_2$ or $OCH_3$;

HetQ' in $R^7$ is a non-aromatic dihydroindolyl, dihydropyridinyl, or dihydroisochromenyl, which is optionally substituted with from 1 to 3 $X^A$ substituents which are Cl or oxo, and
   all other variables are as defined in any of the first through seventh embodiments. In one aspect of this embodiment, $R^7$ is phenyl which is optionally substituted with a total of from 1 to 3 substituents, wherein:

(a) from zero to three substituents which are independently:
(1) $CF_3$,
(2) Cl,
(3) F,
(4) $NH_2$,
(5) $N(H)C(O)OCH_3$,
(6) $C(O)CH_3$,
(7) $C(O)NH_2$,
(8) $CH_2OH$,
(9) $CH(OH)CH_3$,
(10) $CH_2C(CH_3)_2OH$, or
(11) $CH(CF_3)OH$,
(b) from zero to one substituent which is:
(1) $CH_2$-pyridinyl,
(2) C(O)-pyridinyl, or
(3) a heteroaromatic ring which is pyrazolyl optionally substituted with $CH_3$, oxazolyl, tetrazolyl, triazolyl, or isoxazolyl.

In another aspect of this embodiment, $R^7$ is:
(1) phenyl,
(2) 4-aminophenyl,
(3) 4-amino-3-fluorophenyl,
(4) 4-amino-2-fluorophenyl,
(5) 4-amino-2-chlorophenyl,
(6) 4-amino-3-chlorophenyl,
(7) 4-aminocarbonylphenyl,
(8) 4-hydroxymethylphenyl,
(9) 4-hydroxymethyl-3-trifluoromethylphenyl,
(10) 3,5-difluoro-4-hydroxymethylphenyl,
(11) 4-(2-hydroxy-2-methylpropyl)phenyl,
(12) 4-(1-hydroxyethyl)phenyl,
(13) 4-(2,2,2-trifluoro-1-hydroxyethyl)phenyl,
(14) 4-acetylphenyl,
(15) 4-[(methoxycarbonyl)amino]phenyl,
(16) 3-(pyridin-2-ylcarbonyl)phenyl,
(17) 3-(pyridin-2-ylmethyl)phenyl,
(18) 4-(1,3-oxazol-5-yl)phenyl,
(19) 4-(1H-pyrazol-3-yl optionally substituted with $CH_3$) phenyl,
(20) 4-(2H-tetrazol-2-yl)phenyl,
(21) 4-(1H-tetrazol-1-yl)phenyl,
(22) 4-(2H-triazol-2-yl)phenyl,
(23) 4-(1H-triazol-1-yl)phenyl,
(24) 4-(isoxazol-5-yl)phenyl,
(25) 4-(1H-pyrazol-4-yl optionally substituted with $CH_3$) phenyl,
(26) 1-hydroxy-2,3-dihydro-1H-inden-5-yl, or.
(27) 3-hydroxy-2,3-dihydro-1H-inden-5-yl.
In one subaspect of this aspect, $R^7$ is 4-aminophenyl.
In another aspect of this embodiment, $R^7$ is (i) a heteroaryl selected from the group consisting of thiophenyl, pyridinyl, indolyl, benzothiazolyl, indazolyl, benzothiadiazolyl, benzimidazolyl, benzothiophenyl, benzooxazolyl, benzotriazolyl, imidazopyridinyl, imidazopyrazinyl, triazolopyridinyl, triazolopyrazinyl, quinolinyl; wherein the heteroaryl is optionally substituted with from 1 to 3 substituents each of which is independently:
(1) $OCH_3$,
(2) Cl, or
(3) $NH_2$;
or is (ii) a non-aromatic dihydroindolyl, dihydroisoquinolinyl, dihydroisochromenyl, dihydropyridinyl which is optionally substituted with from 1 to 3 substituents each of which is independently oxo and Cl.

In a subaspect of this aspect, $R^7$ is:
(1) 1H-benzimidazol-6-yl,
(2) 1,3-benzooxazol-5-yl,
(3) 1,3-benzothiazol-5-yl,
(4) 1,3-benzothiazol-6-yl,
(5) 1,2,3-benzothiadiazol-6-yl,
(6) 1-benzothiophen-2-yl,
(7) 1H-benzotriazol-6-yl,
(8) 1H-indol-2-yl,
(9) 1H-indol-4-yl,
(10) 1H-indol-5-yl,
(11) 1H-indol-6-yl,
(12) 1H-indazol-5-yl,
(13) 1H-indazol-6-yl,
(14) imidazo[1,2-α]pyrazin-6-yl
(15) 2-chloroimidazo[1,2-α]pyrazin-6-yl
(16) imidazo[1,2-α]pyridin-6-yl,
(17) imidazo[1,2-α]pyridin-7-yl,
(18) 4-aminopyridin-2-yl,
(19) 6-methoxypyridin-3-yl,
(20) quinolin-6-yl,
(21) 4-aminothiophen-2-yl,
(22) 5-aminothiophen-2-yl,
(23) 5-chlorothiophen-2-yl,
(24) [1,2,4]triazolo[1,5-α]pyrazin-6-yl,
(25) [1,2,4]triazolo[1,5-α]pyridin-6-yl,
(26) [1,2,4]triazolo[1,5-α]pyridin-7-yl,
(27) 3-chloro-3a,7a-dihydro-1H-indol-6-yl,
(28) 3,4-dihydro-1H-isochromen-6-yl,
(29) 1-oxo-1,2-dihydroisoquinolin-6-yl, or
(30) 6-oxo-1,6-dihydropyridin-3-yl.

A ninth embodiment of the present invention is a compound of Formula II:

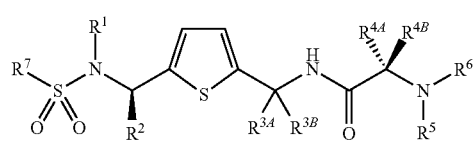

(II)

or a pharmaceutically acceptable salt thereof, and the variables are as defined in any of the first through eighth embodiments. In one aspect of this embodiment, the compound is a compound of formula III:

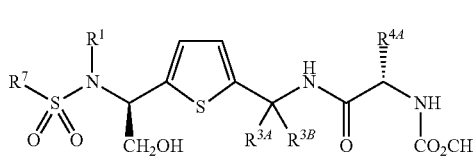

(III)

A tenth embodiment of the invention is a compound of formula I, or a pharmaceutically acceptable salt thereof, wherein the compound is any of the title compounds set forth in Examples 1 to 134.

Another embodiment of the present invention is a compound of Formula I, or a pharmaceutically acceptable salt thereof, as originally defined or as defined in any of the foregoing embodiments, aspects, or subaspects, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest level of purity governs. A compound or salt of 100% purity is one which is free of detectable impurities as determined by a standard method of analysis. The compounds of the invention have two or more asymmetric centers and can occur as mixtures of stereoisomers. It is understood that a substantially pure compound can be either a substantially pure mixture of stereoisomers or a substantially pure individual diastereomer or enantiomer.

Other embodiments of the present invention include the following:

(a) A pharmaceutical composition comprising an effective amount of a compound of Formula I as defined above, or a pharmaceutically acceptable salt thereof, and a pharmaceutically acceptable carrier.

(b) A pharmaceutical composition which comprises the product prepared by combining (e.g., mixing) an effective amount of a compound of Formula I as defined above, or a pharmaceutically acceptable salt thereof, and a pharmaceutically acceptable carrier.

(c) The pharmaceutical composition of (a) or (b), further comprising an effective amount of an anti-HIV agent selected from the group consisting of HIV antiviral agents, immunomodulators, and anti-infective agents.

(d) The pharmaceutical composition of (c), wherein the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(e) The pharmaceutical composition of (d), wherein the antiviral is selected from the group consisting of HIV reverse transcriptase inhibitors and HIV integrase inhibitors.

(f) A combination which is (i) a compound of Formula I as defined above, or a pharmaceutically acceptable salt thereof, and (ii) an anti-HIV agent selected from the group consisting of HIV antiviral agents, immunomodulators, and anti-infective agents; wherein Compound I and the anti-HIV agent are each employed in an amount that renders the combination effective for inhibition of HIV protease, for treatment or prophylaxis of infection by HIV, or for treatment, prophylaxis of, or delay in the onset or progression of AIDS.

(g) The combination of (f), wherein the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(h) The combination of (g), wherein the antiviral is selected from the group consisting of HIV reverse transcriptase inhibitors and HIV integrase inhibitors.

(i) A method for the inhibition of HIV protease in a subject in need thereof which comprises administering to the subject an effective amount of a compound of Formula I or a pharmaceutically acceptable salt thereof.

(j) A method for the prophylaxis or treatment of infection by HIV (e.g., HIV-1) in a subject in need thereof which comprises administering to the subject an effective amount of a compound of Formula I or a pharmaceutically acceptable salt thereof.

(k) The method of (j), wherein the compound of Formula I is administered in combination with an effective amount of at least one other HIV antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(l) The method of (k), wherein the at least one other HIV antiviral is selected from the group consisting of HIV reverse transcriptase inhibitors and HIV integrase inhibitors.

(m) A method for the prophylaxis, treatment or delay in the onset or progression of AIDS in a subject in need thereof which comprises administering to the subject an effective amount of a compound of Formula I or a pharmaceutically acceptable salt thereof.

(n) The method of (m), wherein the compound is administered in combination with an effective amount of at least one other HIV antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(o) The method of (n), wherein the at least one other HIV antiviral is selected from the group consisting of HIV reverse transcriptase inhibitors and HIV integrase inhibitors.

(p) A method for the inhibition of HIV protease in a subject in need thereof which comprises administering to the subject the pharmaceutical composition of (a), (b), (c), (d), or (e) or the combination of (f) or (g).

(q) A method for the prophylaxis or treatment of infection by HIV (e.g., HIV-1) in a subject in need thereof which comprises administering to the subject the pharmaceutical composition of (a), (b), (c), (d), or (e) or the combination of (f) or (g).

(r) A method for the prophylaxis, treatment, or delay in the onset or progression of AIDS in a subject in need thereof which comprises administering to the subject the pharmaceutical composition of (a), (b), (c), (d), or (e) or the combination of (f) or (g).

The present invention also includes a compound of Formula I, or a pharmaceutically acceptable salt thereof, (i) for use in, (ii) for use as a medicament for, or (iii) for use in the manufacture/preparation of a medicament for: (a) therapy (e.g., of the human body), (b) medicine, (c) inhibition of HIV protease, (d) treatment or prophylaxis of infection by HIV, or (e) treatment, prophylaxis of, or delay in the onset or progression of AIDS. In these uses, the compounds of the present invention can optionally be employed in combination with one or more other anti-HIV agents selected from HIV antiviral agents, anti-infective agents, and immunomodulators.

Additional embodiments of the invention include the pharmaceutical compositions, combinations and methods set forth in (a)-(r) above and the uses (i)(a)-(e) through (iii)(a)-(e) set forth in the preceding paragraph, wherein the compound of the present invention employed therein is a compound of one of the embodiments, aspects, subaspects or features described above. In all of these embodiments etc., the compound can optionally be used in the form of a pharmaceutically acceptable salt.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I or a pharmaceutically acceptable carrier and optionally one or more excipients, it is understood that the term "substantially pure" is in reference to a compound of Formula I or its salt per se.

As used herein, the term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and t-butyl, n- and iso-propyl, ethyl and methyl. As another example, "$C_{1-4}$ alkyl" refers to n-, iso-, sec- and t-butyl, n- and isopropyl, ethyl and methyl. As another example, "$C_{1-3}$ alkyl" refers to n-propyl, isopropyl, ethyl and methyl. Alkyl also encompasses saturated aliphatic hydrocarbon radicals wherein one or more hydrogens are replaced with deuterium, for example, $CD_3$.

The term "branched alkyl" refers to an alkyl group as defined above except that straight chain alkyl groups in the specified range are excluded. As defined herein, branched alkyl includes alkyl groups in which the alkyl is attached to the rest of the compound via a secondary or tertiary carbon; e.g., isopropyl is a branched alkyl group.

The term "cycloalkyl" refers to any monocyclic ring of an alkane having a number of carbon atoms in the specified range. Thus, for example, "$C_{3-6}$ cycloalkyl" (or "$C_3$-$C_6$ cycloalkyl") refers to cyclopropyl, cyclobutyl, cyclopentyl, and cyclohexyl, and "$C_{3-5}$ cycloalkyl" refers to cyclopropyl, cyclobutyl, and cyclopentyl.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms have been replaced with a halogen (i.e., F, Cl, Br and/or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.). A fluoroalkyl of particular interest is $CF_3$.

The term "C(O)" refers to carbonyl. The terms "$S(O)_2$" and "$SO_2$" each refer to sulfonyl. The term "S(O)" refers to sulfinyl.

An asterisk ("*") as the end of an open bond in a chemical group denotes the point of attachment of the group to the rest of the compound.

The term "aryl" refers to phenyl, naphthyl, tetrahydronaphthyl, idenyl, dihydroindenyl and the like. An aryl of particular interest is phenyl.

The term "heteroaryl" refers to (i) a 5- or 6-membered heteroaromatic ring containing from 1 to 4 heteroatoms independently selected from N, O and S, or (ii) is a heterobicyclic ring selected from quinolinyl, isoquinolinyl, and quinoxalinyl. Suitable 5- and 6-membered heteroaromatic rings include, for example, pyridyl (also referred to as pyridinyl), pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, oxatriazolyl, thiazolyl, isothiazolyl, and thiadiazolyl. A class of heteroaryls of interest consists of (i) 5- and 6-membered heteroaromatic rings containing from 1 to 3 heteroatoms independently selected from N, O and S, and (ii) heterobicyclic rings selected from quinolinyl, isoquinolinyl, and quinoxalinyl. Heteroaryls of particular interest are pyrrolyl, imidazolyl, pyridyl, pyrazinyl, quinolinyl (or quinolyl), isoquinolinyl (or isoquinolyl), and quinoxalinyl.

Examples of 4- to 7-membered, saturated heterocyclic rings within the scope of this invention include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl. Examples of 4- to 7-membered, unsaturated heterocyclic rings within the scope of this invention include mono-unsaturated heterocyclic rings corresponding to the saturated heterocyclic rings listed in the preceding sentence in which a single bond is replaced with a double bond (e.g., a carbon-carbon single bond is replaced with a carbon-carbon double bond).

It is understood that the specific rings listed above are not a limitation on the rings which can be used in the present invention. These rings are merely representative.

Unless expressly stated to the contrary in a particular context, any of the various cyclic rings and ring systems described herein may be attached to the rest of the compound at any ring atom (i.e., any carbon atom or any heteroatom) provided that a stable compound results.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. As another example, an aryl or heteroaryl described as optionally substituted with "from 1 to 4 substituents" is intended to include as aspects thereof, an aryl or heteroaryl substituted with 1 to 4 substituents, 2 to 4 substituents, 3 to 4 substituents, 4 substituents, 1 to 3 substituents, 2 to 3 substituents, 3 substituents, 1 to 2 substituents, 2 substituents, and 1 substituent.

When any variable (e.g., $X^A$ or $X^B$) occurs more than one time in any constituent or in Formula I or in any other formula depicting and describing compounds of the present invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring (e.g., cycloalkyl, aryl, or heteroaryl) provided such ring substitution is chemically allowed and results in a stable compound.

The compounds of the invention contain chiral centers and, as a result of the selection of substituents and substituent patterns, can contain additional chiral centers, and thus can occur as mixtures of stereoisomers, or as individual diastereomers, or enantiomers. All isomeric forms of these compounds, whether individually or in mixtures, are within the scope of the present invention.

To the extent substituents and substituent patterns provide for the existence of tautomers (e.g., keto-enol tautomers) in the compounds of the invention, all tautomeric forms of these compounds, whether present individually or in mixtures, are within the scope of the present invention. Compounds of the present invention having a hydroxy substituent on a carbon atom of a heteroaromatic ring are understood to include compounds in which only the hydroxy is present, compounds in which only the tautomeric keto form (i.e., an oxo substituent) is present, and compounds in which the keto and enol forms are both present.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present invention are limited to stable compounds embraced by Formula I.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H or D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

The methods of the present invention involve the use of compounds of the present invention in the inhibition of HIV protease (e.g., wild type HIV-1 and/or mutant strains thereof), the prophylaxis or treatment of infection by human immunodeficiency virus and the prophylaxis, treatment or delay in the onset or progression of consequent pathological conditions such as AIDS. Prophylaxis of AIDS, treating AIDS, delaying the onset or progression of AIDS, or treating or prophylaxis of infection by HIV is defined as including, but not limited to, treatment of a wide range of states of HIV infection: AIDS, ARC (AIDS related complex), both symptomatic and asymptomatic, and actual or potential exposure to HIV. For example, the present invention can be employed to treat infection by HIV after suspected past exposure to HIV by such means as blood transfusion, exchange of body fluids, bites, accidental needle stick, or exposure to patient blood during surgery.

The compounds can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, or benzoic acid. When compounds employed in the present invention carry an acidic moiety (e.g., —COOH or a phenolic group), suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts.

The term "administration" and variants thereof (e.g., "administering" a compound) in reference to a compound of Formula I mean providing the compound to the individual in need of treatment or prophylaxis. When a compound is provided in combination with one or more other active agents (e.g., antiviral agents useful for treating or prophylaxis of HIV infection or AIDS), "administration" and its variants are each understood to include provision of the compound and other agents at the same time or at different times. When the agents of a combination are administered at the same time, they can be administered together in a single composition or they can be administered separately.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit HIV protease (wild type and/or mutant strains thereof) and thereby elicit the response being sought (i.e., an "inhibition effective amount"). When the active compound (i.e., active ingredient) is administered as the salt, references to the amount of active ingredient are to the free form (i.e., the non-salt form) of the compound.

In the methods of the present invention (i.e., inhibiting HIV protease, treating or prophylaxis of HIV infection or treating, prophylaxis of, or delaying the onset or progression of AIDS), the compounds of Formula I, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like.

Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions for use in the present invention and of ingredients suitable for use in said compositions is provided in *Remington's Pharmaceutical Sciences*, 18th edition, edited by A. R. Gennaro, Mack Publishing Co., 1990 and in *Remington—The Science and Practice of Pharmacy*, 21st edition, Lippincott Williams & Wilkins, 2005.

The compounds of Formula I can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention is also directed to use of a compound of Formula I with one or more anti-HIV agents. An "anti-HIV agent" is any agent which is directly or indirectly effective in the inhibition of HIV reverse transcriptase, protease, or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, immunomodulators, antiinfectives, or vaccines useful for treating HIV infection or AIDS, such as those disclosed in Table 1 of WO 01/38332 or in the Table in WO 02/30930. Suitable HIV antivirals for use in combination with the compounds of the present invention include, for example, those listed in Table A as follows:

TABLE A

Antiviral Agents for Treating HIV infection or AIDS

| Name | Type |
| --- | --- |
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |

TABLE A-continued

Antiviral Agents for Treating HIV infection or AIDS

| Name | Type |
| --- | --- |
| capravirine | nnRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| efavirenz, EFV, Sustiva ®, Stocrin ® | nnRTI |
| efavirenz + emtricitabine + tenofovir DF, Atripla ® | nnRTI + nRTI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPL-100 (also known as PL-462) (Ambrilia) | PI |
| raltegravir, MK-0518, Isentress ™ | InI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| tipranavir, Aptivus ® | PI |

EI = entry inhibitor;
FI = fusion inhibitor;
InI = integrase inhibitor;
PI = protease inhibitor;
nRTI = nucleoside reverse transcriptase inhibitor;
nnRTI = non-nucleoside reverse transcriptase inhibitor.
Some of the drugs listed in the table are used in a salt form; e.g., abacavir sulfate, indinavir sulfate, atazanavir sulfate, nelfinavir mesylate.

It is understood that the scope of combinations of the compounds of this invention with anti-HIV agents is not limited to the HIV antivirals listed in Table A and/or listed in the above-referenced Tables in WO 01/38332 and WO 02/30930, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson PDR, Thomson PDR, 57th edition (2003), the 58th edition (2004), or the 59th edition (2005). The dosage ranges for a compound of the invention in these combinations are the same as those set forth above.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV protease, e.g., by competitive inhibition.

ABBREVIATIONS

Abbreviations employed herein include the following:
AcOH=acetic acid;
AllocCl=Allyloxycarbonyl chloride;
BOC or Boc=t-butyloxycarbonyl;

BOP=benzotriazol-1-yloxytris-(dimethylamino)phosphonium;
DCM=dichloromethane;
DIAD=diisopropylazodicarboxylate;
DIPEA=N,N-diisopropylethylamine;
DMAP=4-dimethylaminopyridine;
DMF=N,N-dimethylformamide;
DMSO=dimethylsulfoxide;
$Et_2O$=ethyl ether;
$Et_3N$=triethylamine;
EtOH=ethanol;
EtOAc=ethyl acetate;
MeMgBr=methyl magnesium bromide;
MeOH=methanol;
MS=mass spectrometry;
MTBE=methyl tert-butyl ether;
n-BuLi or nBuLi=n-butyllithium;
$NaBH_4$=sodium borohydride;
NCS=N-chlorosuccinimide;
NMR=nuclear magnetic resonance;
Pd/C=palladium on carbon;
$Pd(PPh_3)_4$=(tetrakis(triphenylphosphine)palladium;
$Ph_3P$=triphenylphosphine;
RT=room temperature;
t-BuLi=tert butyllithium;
$Ti(OEt)_4$=titanium ethoxide;
TBAF=tetrabutylammonium fluoride;
TBS=t-butyldimethylsilyl;
TBDMSCl or TBSCl=t-butyldimethylsilyl chloride;
TEA=triethylamine;
THF=tetrahydrofuran;
TMSCl=trimethylsilyl chloride;
TsOH=p-toluenesulfonic acid.

The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The term "Ar" appears in several of the schemes and refers to phenyl optionally substituted with one or more $X^A$.

Compounds of the present invention can be prepared in accordance with Scheme I shown below. The halogenated heterocycle I-1 can be metallated (e.g., with an alkyllithium such as n-BuLi in a suitable solvent such as THF) and then treated with a sulfoximine to afford I-2. The sulfoxide and silyl protecting group in I-2 can then be removed by treatment with acid (e.g., HCl) to afford I-3, after which the alcohol moiety is re-protected with a silyl group (e.g., by treatment with TBSCl in the presence of DMAP, TEA and imidazole in a suitable solvent such as DCM) to provide I-4. The amine in I-4 can then be reductively alkylated with a suitable aldehyde to afford the alkylated amine I-5, which can then be sulfonylated with a suitable sulfonyl halide to provide I-6. The aldehyde moiety can then be introduced via lithium halogen exchange and quenching with DMF. Conversion to an amine followed by installation of the appropriate amino acid and alcohol deprotection give the final compounds. Aldehyde I-7 can then be formed by treating I-6 with an alkyl lithium (e.g., n-BuLi or t-BuLi in THF) followed by quenching with a tertiary amide such as DMF. Aldehyde I-7 can then be converted to amine I-8 by treatment of I-7 with a sulfonamide (e.g., t-butyl sulfonamide) in the presence of a titanium alkoxide (e.g., $Ti(OEt)_4$), followed by borohydride (e.g., $NaBH_4$) reduction, and acid (e.g., HCl) deprotection. Amine I-8 can then be coupled with a suitable carboxylic acid I-9 (e.g., reaction in the presence of BOP) to provide the desired amide I-9.

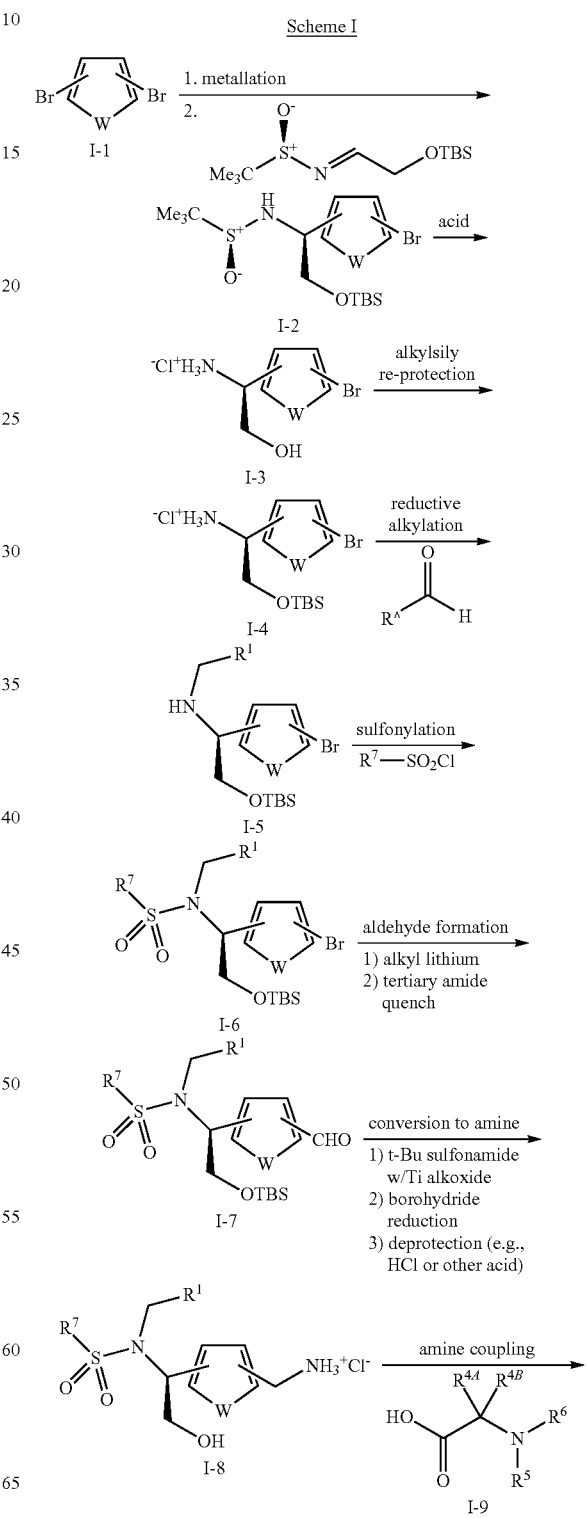

Scheme I

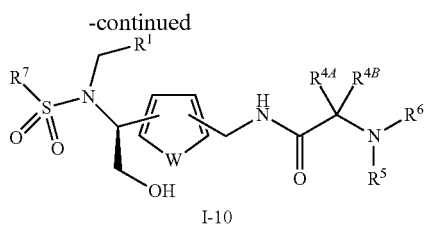

I-10

[W = NH, O or S]

The following intermediates (not commercially available) were prepared as described in the examples below and employed in the preparation of one or more compounds set forth in Examples 1 to 134.

Intermediate Example 1 tert-butyl 3-chloro-6-(chlorosulfonyl)-1H-indole-1-carboxylate

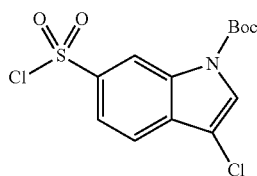 [SMILES: CC(C)(C)OC(=O)n1cc(Cl)c2ccc(S(=O)(=O)Cl)cc21]

tert-Butyl 6-bromo-3-chloro-1H-indole-1-carboxylate (50 mg, 0.151 mmol) was suspended in 1.5 mL ether. The suspension was cooled to −78° C. and t-BuLi (178 μL of a 1.7 M solution in pentane, 0.302 mmol) was added dropwise. The mixture was then stirred for 1 minute, $SO_2$ gas was bubbled through the mixture for 5 minutes, and the mixture was then stirred for an additional 5 minutes. The solvent was removed before DCM (2 mL) and NCS (20.2 mg, 0.151 mmol) were added. The mixture was then stirred for 1 hour and the solvent was removed in vacuo to afford the title compound.

Intermediate Example 2

1-{[tert-butyl(dimethyl)silyl]oxy}-2,3-dihydro-1H-indene-5-sulfonyl chloride

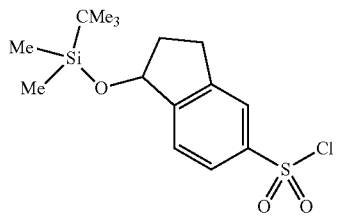

Step 1: [(5-bromo-2,3-dihydro-1H-inden-1-yl)oxy](tert-butyl)dimethylsilane

To a solution of 5-bromo-2,3-dihydro-1H-inden-1-ol (1 g, 4.69 mmol), triethylamine (1.44 mL, 10.3 mmol) and dimethylaminopyridine (0.12 g, 0.94 mmol) in DCM (20 mL) at 0° C. was added TBSCl (1.56 g, 5.16 mmol). The reaction mixture was allowed to reach room temperature overnight, and then was quenched with a saturated solution of sodium bicarbonate (20 mL). The phases were separated and the aqueous layer was extracted twice with DCM (2×20 mL). The organics layers were combined, washed with brine, dried over magnesium sulfate, filtered and concentrated under reduced pressure. The crude material was purified on silica eluting with $Et_2O$ and pentane to afford the title compound.

Step 2: Methyl 3-[(1-{[tert-butyl(dimethyl)silyl]oxy}-2,3-dihydro-1H-inden-5-yl)sulfonyl]propanoate

[(5-bromo-2,3-dihydro-1H-inden-1-yl)oxy](tert-butyl)dimethylsilane (1.62 g, 4.95 mmol), sodium 3-methoxy-3-oxopropane-1-sulfinate (3.45 g, 19.8 mmol) and CuI (3.77 g, 19.8 mmol) were charged in a sealable microwave flask. The flask was closed and degassed twice, after which dry DMSO (10 mL) was added and the reaction mixture was degassed before being heated at 110° C. in an oil bath overnight. The reaction mixture was cooled and diluted with ethyl acetate (40 mL), filtered on a silica gel pad, and eluted with ethyl acetate. The organic solvents were concentrated under reduced pressure. The crude concentrate was purified on silica gel eluting with hexanes and ethyl acetate, then with DCM and methanol to afford the title compound.

Step 3: 1-{[tert-butyl(dimethyl)silyl]oxy}-2,3-dihydro-1H-indene-5-sulfonyl chloride To a solution of methyl 3-[(1-{[tert-butyl(dimethyl)silyl]oxy}-2,3-dihydro-1H-inden-5-yl)sulfonyl]propanoate (140 mg, 0.35 mmol) in THF (1 mL) was added sodium methoxide (0.70 mL, 0.5 M, 0.35 mmol). The reaction mixture was stirred for 20 minutes, then the solvents were removed under reduced pressure and the residue was stripped down from heptanes to generate a white foam. This foam was suspended in DCM (2 mL) at 0° C. and then NCS (47 mg, 0.35 mmol) was added and the reaction mixture was stirred for 1 hour. The reaction was quenched by the addition of brine (2 mL) and the phases were separated using a phase separator. The aqueous layer washed with DCM, and the combined organic layers were concentrated under reduced pressure. The crude concentrate was purified on silica gel eluting with hexanes and ethyl acetate to afford the title compound.

Intermediate Example 3

1-(propan-2-ylsulfonyl)-1H-indazole-5-sulfonyl chloride

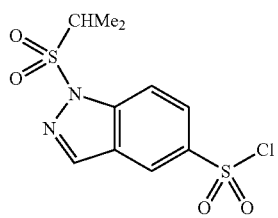

Step 1: 5-bromo-1-(propan-2-ylsulfonyl)-1H-indazole

To a solution of 5-bromo-1H-indazole (2 g, 10.2 mmol) in THF (100 mL) was added sodium hydride (0.61 g, 15.2 mmol) at 0° C. for 1 hour. Dimethylsulfamoyl chloride was then added dropwise, and then the reaction mixture was allowed to reach room temperature overnight. The reaction mixture was then quenched by the addition of a saturated aqueous solution of sodium bicarbonate (100 mL), and the mixture was diluted with ethyl acetate (250 mL). The layers were separated, and the aqueous layer was extracted twice with ethyl acetate (2×250 mL). The organic layers were combined, dried over magnesium sulfate, filtered and concentrated under reduced pressure. The crude concentrate was purified on silica gel eluting with hexanes and ethyl acetate to afford the title compound.

Step 2: Methyl 3-{[1-(propan-2-ylsulfonyl)-1H-indazol-5-yl]sulfonyl}propanoate 5-bromo-1-(propan-2-ylsulfonyl)-1H-indazole (0.85 g, 2.79 mmol), sodium 3-methoxy-3-oxopropane-1-sulfinate (2.42 g, 13.9 mmol) and CuI (2.66 g, 13.9 mmol) were charged in a sealable microwave flask. The flask was closed and degassed twice, after which dry DMSO (3.0 mL) was added and the reaction mixture degassed before being heated at 110° C. in an oil bath overnight. The reaction mixture was cooled and diluted with ethyl acetate (40 mL), and then filtered on a silica gel pad and eluted with ethyl acetate. The organic phases were concentrated under reduced pressure. The crude was purified on silica gel eluting with hexanes and ethyl acetate, then with DCM and methanol to afford the title compound.

Step 3: 1-(propan-2-ylsulfonyl)-1H-indazole-5-sulfonyl chloride

To a solution of methyl 3-{[1-(propan-2-ylsulfonyl)-1H-indazol-5-yl]sulfonyl}propanoate (300 mg, 0.80 mmol) in THF (4 mL) was added sodium methoxide (1.6 mL, 0.5 M, 0.80 mmol). The reaction mixture was stirred for 20 minutes, then the solvents were removed under reduced pressure and the residue was stripped down from heptanes to generate a white foam. This foam was suspended in DCM (4 mL) at 0° C. and then NCS (106 mg, 0.80 mmol) was added and the reaction mixture was stirred for 1 hour. The reaction was quenched by the addition of brine (4 mL) and the phases were separated using a phase separator. The aqueous layer was washed with DCM. The combined organic layers were concentrated under reduced pressure, and the crude was purified on silica gel eluting with hexanes and ethyl acetate to afford the title compound.

Intermediate Example 4 tert-butyl 6-(chlorosulfonyl)-1H-indole-1-carboxylate

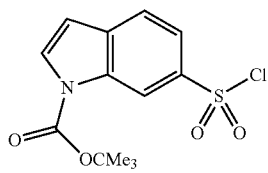

Step 1: Methyl 3-(1H-indol-6-ylsulfonyl)propanoate 6-bromo-1H-indole (3.0 g, 15.3 mmol), sodium 3-methoxy-3-oxopropane-1-sulfinate (8.0 g, 45.9 mmol) and CuI (14.6 g, 77.0 mmol) were charged to a sealable flask. The flask was closed and degassed twice, and then dry DMSO (30 mL) was added and the reaction mixture degassed again before being heated at 110° C. in an oil bath overnight. The reaction mixture was cooled and diluted with ethyl acetate (300 mL). The mixture was filtered on a silica gel pad and eluted with ethyl acetate. The organic phase was concentrated under reduced pressure. The crude was purified on silica gel eluting with hexanes and ethyl acetate, then with DCM and methanol to afford the title compound.

Step 2: tert-butyl 6-[(3-methoxy-3-oxopropyl)sulfonyl]-1H-indole-1-carboxylate

To a solution of methyl 3-(1H-indol-6-ylsulfonyl)propanoate (3.98 g, 9.83 mmol) in acetonitrile (33 mL) was added BOC anhydride (2.57 g, 11.8 mmol) followed by DMAP (0.12 g, 0.98 mmol) and TEA (1.78 mL, 12.8 mmol). The reaction mixture was stirred at room temperature for 30 minutes before being concentrated under reduced pressure. The resulting slurry was then diluted with ethyl acetate (250 mL) and the organic layer was washed with a saturated solution of sodium bicarbonate (250 mL) and brine (250 mL). The organic layers were dried over magnesium sulfate, filtered and concentrated under reduced pressure. The crude was purified on silica gel eluting with hexanes and ethyl acetate to afford the title compound.

Step 3: tert-butyl 6-(chlorosulfonyl)-1H-indole-1-carboxylate

To a solution of tert-butyl 6-[(3-methoxy-3-oxopropyl)sulfonyl]-1H-indole-1-carboxylate (400 mg, 1.13 mmol) in THF (5.5 mL) was added sodium methoxide (2.26 mL, 0.5 M, 1.13 mmol). The reaction mixture was stirred for 20 minutes, then the solvents were removed under reduced pressure and the residue was stripped down from heptanes to generate a white foam. This foam was suspended in DCM (5.5 mL) at 0° C. and then NCS (151 mg, 1.13 mmol) was added and the reaction mixture was stirred for 1 hour. The reaction was quenched by the addition of brine (4 mL) and the phases were separated using a phase separator. The aqueous layer washed with DCM. The combined organics were concentrated under reduced pressure. The crude was purified on silica gel eluting with hexanes and ethyl acetate to afford the title compound.

Intermediate Example 5

4-(2H-tetrazol-2-yl)aniline

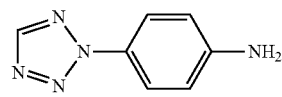

To a solution of 4-fluoro-1-nitrobenzene (12.5 g, 89 mmol) and 1H-tetrazole (6.21 g, 89 mmol) in DMF (89 mL) stirred at room temperature, potassium carbonate (12.24 g, 89 mmol) was added in one portion. The resulting mixture was stirred at 80° C. overnight, and then reaction mixture was worked up by the addition of water at 80° C., then cooled to room temperature, and stirred at room temperature for 30 minutes. The yellow solid was collected by filtration, washed with water, air-dried for 2 hours, and dried in an vacuum oven at 60° C. for 2 hours to afford a mixture of 4-(1H-tetrazol-1-yl)-1-nitrobenzene and 4-(2H-tetrazol-2-yl)-1-nitrobenzene. The product thus obtained was re-dissolved in THF (209 mL) and, while stirring at room temperature, platinum(IV) oxide (0.45 g, 1.982 mmol) was added in one portion. The resulting mixture was stirred at room temperature overnight under a hydrogen atmosphere, after which the reaction mixture was worked up by filtration through a celite pad and the solvent removed by evaporation. The residue was purified and separated by CombiFlash® (0-50% EtOAc/toluene; Teledyne Isco, Inc., Lincoln, Nebr.) to afford the desired 4-(2H-tetrazol-2-yl)aniline as a yellowish solid. $^1$H NMR (400 MHz, DMSO-d$_6$): δ 9.08 (s, 1H), 7.72 (d, 2H), 6.73 (d, 2H), 5.75 (s, 2H).

Intermediate Example 6

4-(1H-1,2,3-triazol-1-yl)aniline and 4-(2H-1,2,3-triazol-2-yl)aniline

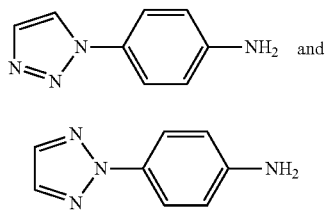

To a solution of 4-fluoro-1-nitrobenzene (10.21 g, 72.4 mmol) and 1H-1,2,3-triazole (5 g, 72.4 mmol) in DMF (72.4 mL) stirred at room temperature, NaH (2.90 g, 72.4 mmol) was added portionwise. The resulting mixture was stirred at room temperature overnight, after which the reaction mixture was worked up by the addition of water and stirred at room temperature for 30 minutes. The yellow solid was collected by filtration, washed with water, air-dried for 2 hours, and then dried in a vacuum oven at 60° C. for 2 hours to afford a mixture of 4-(1H-1,2,3-triazol-1-yl)-1-nitrobenzene and 4-(2H-1,2,3-triazol-2-yl)-1-nitrobenzene. The mixture was re-dissolved in THF (150 mL) and, while stirring at room temperature, platinum(IV) oxide (0.281 g, 1.236 mmol) was added in one portion. The resulting mixture was stirred at room temperature overnight under a hydrogen atmosphere, after which the reaction mixture was worked up by the filtration through a silica gel pad at room temperature and washed with ethyl acetate, and evaporated. The residue was purified and separated by CombiFlash® (0-100% EtOAc/hexane) to afford the title products as a yellowish solid.

4-(1H-1,2,3-triazol-1-yl)aniline—$^1$H NMR (400 MHz, DMSO-d$_6$): δ 8.53 (s, 1H), 7.86 (s, 1H), 7.48 (d, 2H), 6.69 (d, 2H), 5.48 (s, 2H).

4-(2H-1,2,3-triazol-2-yl)aniline—$^1$H NMR (400 MHz, DMSO-d$_6$): δ 7.95 (s, 2H), 7.65 (d, 2H), 6.67 (d, 2H), 5.42 (s, 2H).

Intermediate Example 7

4-(2H-tetrazol-2-yl)benzenesulfonyl chloride

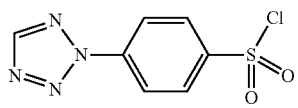 [SMILES: O=S(=O)(Cl)c1ccc(-n2ncnn2)cc1]

To a solution of 4-(2H-tetrazol-2-yl)aniline (2 g, 12.41 mmol) and hydrochloric acid (3.52 mL, 42.8 mmol) in acetonitrile (124 mL) and acetic acid (7 mL) stirred at −10° C., sodium nitrite (2.349 mL, 14.89 mmol) was added dropwise. The resulting mixture was stirred at 0° C. for 10 minutes, after which sulfur dioxide/acetic acid (saturated) (44 mL, 12.41 mmol) was added dropwise to the resulting mixture at a rate such that the reaction temperature is maintained below 5° C. Following the addition of SO$_2$, a solution of copper(II) chloride dihydrate (3.61 mL, 15.51 mmol) was added dropwise. The reaction mixture was allowed to react at 0° C. for 30 minutes and then was warmed to room temperature and stirred at room temperature for 3 hours. The mixture was poured onto 400 g of ice and stirred until all the ice melted. The solid was collected by filtration and washed with water and air-dried to afford the title compound. $^1$H NMR (400 MHz, acetone-d$_6$): δ 9.15 (s, 1H), 8.62 (d, 2H), 8.48 (d, 2H).

Intermediate Examples 8 to 10

The compounds shown in the table below were prepared in accordance with the procedures described above in Intermediate Examples 5 to 7.

| Example number | Structure & Name | Characterization |
|---|---|---|
| 8 | ![structure] 4-(2H-1,2,3-triazol-2-yl)benzenesulfonyl chloride | $^1$H NMR (400 MHz, DMSO-d$_6$): δ 8.14 (s, 2 H), 7.99 (d, 2 H), 7.78 (d, 2 H). |
| 9 | ![structure] 4-(1H-1,2,3-triazol-2-yl)benzenesulfonyl chloride | $^1$H NMR (400 MHz, DMSO-d$_6$): δ 8.86 (s, 1 H), 7.98 (s, 1 H), 7.88 (d, 2 H), 7.79 (d, 2 H). |
| 10 | ![structure] 4-isoxazol-5-ylbenzenesulfonyl chloride | $^1$H NMR (400 MHz, Acetone-d$_6$): δ 8.64 (d, 1 H), 8.32 (s, 4 H), 7.26 (d, 1 H). |

Intermediate Example 11

[1,2,4]triazolo[1,5-α]pyridine-7-sulfonyl chloride

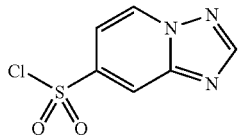 [SMILES: O=S(=O)(Cl)c1ccn2ncnc2c1]

To a solution of 7-(benzylsulfanyl)[1,2,4]triazolo[1,5-c]pyridine (100 mg, 0.414 mmol) in acetonitrile (2 mL) at room temperature was added sufuryl chloride (0.135 mL, 1.658 mmol) in one portion. The mixture was agitated for 1 hour. The white solid was filtered through a Whatman paper #1 (Whatman, Inc., Piscataway, N.J.) and washed with a minimum of cold acetonitrile to afford the title material as white solid. MS: m/z=218.1 ((MH+)).

Intermediate Example 12

[1,2,4]triazolo[1,5-α]pyridine-6-sulfonyl chloride

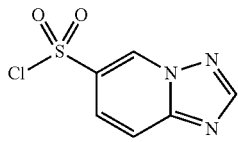 [SMILES: O=S(=O)(Cl)c1ccc2ncnn2c1]

To a solution of 6-(benzylsulfanyl)[1,2,4]triazolo[1,5-α]pyridine (100 mg, 0.414 mmol) in AcOH (2 mL) at room temperature was added NCS (221 mg, 1.658 mmol) in one portion. The mixture was agitated for 45 minutes, after which ice (10 mL) and water (15 mL) were added to the mixture. The white precipitate was filtered through a Whatman paper #1 to afford the title material as white solid. The filtrate was extracted with EtOAc (3×). MS: m/z=218.1 ((MH+)).

Intermediate Example 13

2-chloroimidazo[1,2-a]pyrazine-6-sulfonyl chloride

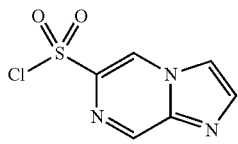

To a solution of 6-(benzylsulfanyl)imidazo[1,2-a]pyrazine (415 mg, 1.720 mmol) in acetic acid (10 mL) at room temperature was added NCS (919 mg, 6.88 mmol). The mixture was stirred for 1 hour at room temperature. The volatile components were evaporated under reduced pressure, and the crude residue was taken in EtOAc and water 1:1. The layers were separated and the combined organic extracts were dried over MgSO₄, filtered through a fitted glass funnel and the filtrate was evaporated to dryness under reduced pressure. The crude residue was purified by flash chromatography (Combiflash® Rf system; SiO₂ 12 grams Cat. No. 69-2203-312, solvent flow 30 mL/minute, elution gradient of 20-100% EtOAc/hexanes). The fractions containing the desired product were pooled and evaporated under reduced pressure to afford the title product as a white solid. MS: m/z=251.9254.4 ((MH+)).

Intermediate Example 14

[1,2,4]triazolo[1,5-a]pyrazine-6-sulfonyl chloride

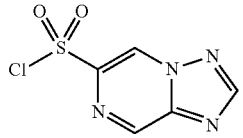 [SMILES: O=S(=O)(Cl)c1cn2ncnc2cn1]

To a solution of 6-(benzylsulfanyl)[1,2,4]triazolo[1,5-a]pyrazine (100 mg, 0.413 mmol) in acetonitrile (1.5 mL) at 0° C. was added HCl 2N (0.413 mL, 0.825 mmol) followed by NCS (220 mg, 1.651 mmol). The mixture was stirred for 2 hours at a temperature that did not exceed 10° C. The mixture was then diluted with DCM and filtered through a Isolute® SPE phase separator cartridge (Biotage, LLC, Charlotte, N.C.). The filtrate was evaporated under reduced pressure to afford the crude title material as colorless oil that solidified on standing. MS: m/z=219.1 ((MH+)).

Intermediate Example 15

N-phenylcarbonyl-β-naphthyl-L-phenylalanine

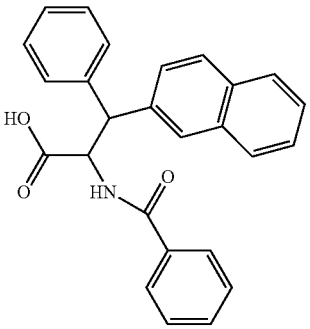 [SMILES: O=C(NC(C(=O)O)C(c1ccccc1)c1ccc2ccccc2c1)c1ccccc1]

Step 1: (4Z)-4-(naphthalen-1-ylmethylidene)-2-phenyl-1,3-oxazol-5(4H)-one

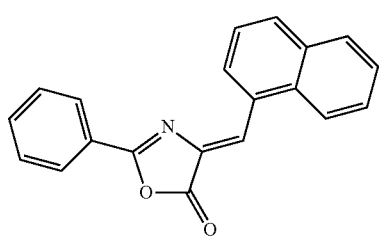 [SMILES: O=C1OC(c2ccccc2)=N/C1=C\c1cccc2ccccc12]

A solution of hippuric acid (4.0 g, 1.0 eq.) was added to a solution acetic anhydride (10 mL), 1-naphthylaldehyde (3.84 g, 1.1 eq.) and sodium acetate (2.21 g, 1.2 eq.). The reaction mixture was then heated at 80° C. for 2 hours, then cooled to room temperature, filtered, and washed with acetic anhydride. After air drying, the solid was washed back with water and air-dried overnight to give the desired compound.

Step 2:
N-phenylcarbonyl-β-naphthyl-L-phenylalanine

Phenylmagnesium bromide in ether (1.604 mL, 4.01 mmol.) was added to a suspension of cuprous chloride I (0.496 g, 5.01 mmol) in 6 mL of ether at room temperature. The reaction mixture was stirred for 15 minutes and the resulting suspension was added to a solution of oxazolone (1 g, 3.34 mmol) in THF (6 mL). The resulting suspension was stirred at room temperature for 1.5 hours before being quenched with HCl. Acid base extraction in ethyl acetate followed with a co-evaporation with heptane ether gave the desired product.

Similar amino acid intermediates suitable for use in the preparation of other compounds of the invention can be prepared in similar fashion.

Intermediate Example 16

N-[(1E)-2-{[tert-butyl(dimethyl)silyl]oxy}ethylidene]-2-methylpropane-2-sulfinamide

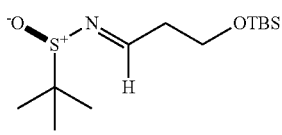

A three necked round bottom flask fitted with a mechanical stirrer, nitrogen inlet and temperature probe was charged with (S)-(−)-2-Methyl-2-Propanesulfinamide (113 g, 0.929 mol) and DCM (2.0 L) at RT (endotherm to 9° C.). Copper(II) Sulfate (309 g, 1.94 mol) was then added followed by (tert-butyldimethylsilyl-oxy)acetaldehyde (150 g, 0.774 mol). After 36 hours the reaction was filtered through a plug of Celite, plug rinsed with DCM (3×200 mL), and concentrated to provide 248 g of the title compound as a light yellow syrup (87 wt %). 1H NMR (CDCl$_3$) δ 8.08 (1H, s), 4.56 (2H, s), 1.22 (9H, s), 0.95 (9H, s), 0.12 (6H, s).

Example 1

N-[(5-{2-hydroxy-1-[(3-methylbutyl)(phenylsulfonyl)amino]ethyl}thiophen-3-yl)methyl]-Nα-(methoxycarbonyl)-β-phenyl-L-phenylalaninamide

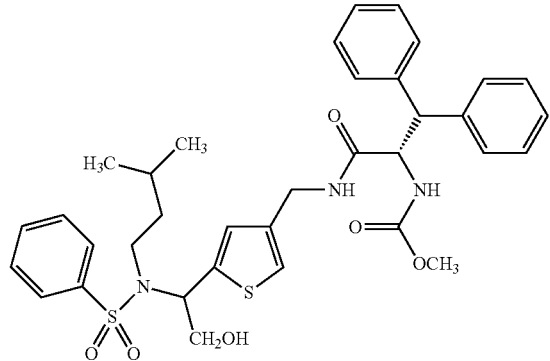 [SMILES: COC(=O)N[C@H](C(=O)NCc1csc(C(CO)N(CCC(C)C)S(=O)(=O)c2ccccc2)c1)C(c1ccccc1)c1ccccc1]

Reaction Sequence:

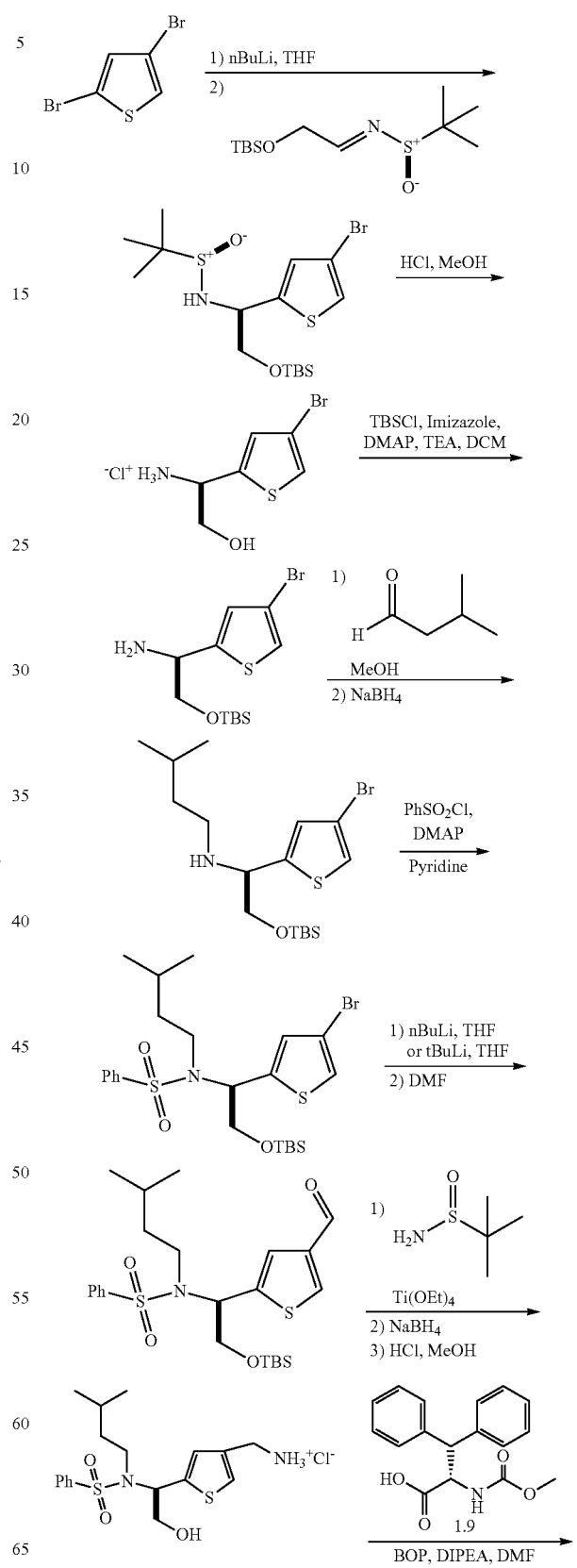

-continued

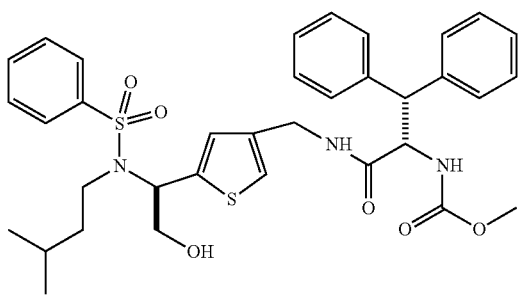

Step 1: N-[1-(4-bromothiophen-2-yl)-2-{[tert-butyl(dimethyl)silyl]oxy}ethyl]-2-methylpropane-2-sulfinamide 2,4-dibromothiophene (3.49 g, 14.41 mmol) was dissolved in Et$_2$O (120 mL) at −78° C., and then n-BuLi (4.32 mL of 2.5 M, 10.8 mmol) was added dropwise and the resulting mixture was stirred for 30 minutes. This solution was cannulated into a solution of N-[(1E)-2-{[tert-butyl(dimethyl)silyl]oxy}ethylidene]-2-methylpropane-2-sulfinamide (2 g, 7.21 mmol) in 120 mL DCM at −78° C. The reaction mixture was quenched with aqueous ammonium chloride and warmed to room temperature. The mixture was extracted with ethyl acetate (3×) and the combined organic fractions were washed with brine, dried (MgSO$_4$), and filtered. The ethyl acetate solvent was then evaporated under reduced pressure, and the resulting product purified on silica gel (EtOAc/hexanes) to give the title compound.

Step 2: 1-(4-bromothiophen-2-yl)-2-hydroxyethanaminium chloride

N-[1-(4-bromothiophen-2-yl)-2-{[tert-butyl(dimethyl)silyl]oxy}ethyl]-2-methylpropane-2-sulfinamide (660 mg, 1.5 mmol) was dissolved in MeOH (15 mL) and the solution was cooled to 0° C., after which HCl (1.87 mL of a 4M solution in dioxane, 7.49 mmol) was added and the mixture was stirred for 120 minutes. The solvents were removed by coevaporation with toluene.

Step 3: 1-(4-bromothiophen-2-yl)-2-{[tert-butyl(dimethyl)silyl]oxy}ethanamine 1-(4-bromothiophen-2-yl)-2-hydroxyethanaminium chloride (300 mg, 1.35 mmol), imidazole (120 mg, 1.76 mmol), DMAP (8.25 mg, 0.068 mmol) and TEA (188 µL, 1.35 mmol) were dissolved in 13.5 mL DCM. TBSCl was then added (265 mg, 1.76 mmol) at 0° C. and the mixture was stirred for 48 hours at room temperature. The mixture was quenched with saturated NaHCO$_3$ and the phases separated. The organic extract was concentrated and purified on silica gel (EtOAc/hexanes).

Step 4: N-[1-(4-bromothiophen-2-yl)-2-{[tert-butyl(dimethyl)silyl]oxy}ethyl]-3-methylbutan-1-amine 1-(4-bromothiophen-2-yl)-2-{[tert-butyl(dimethyl)silyl]oxy}ethanamine (216 mg, 0.642 mmol) was dissolved in 1.5 mL MeOH. Molecular sieves (3 Å) and 3-methylbutanal (79 µL, 0.739 mmol) were then added. The resulting mixture was stirred at room temperature overnight. Sodium borohydride (36.4 mg, 0.963 mmol) was added and the mixture was stirred for 1 hour, and then quenched with aqueous sodium hydrogen carbonate. DCM was added and the phases separated. The solvent was removed under reduced pressure. The resulting solid was used without further purification.

Step 5: N-[1-(4-bromothiophen-2-yl)-2-{[tert-butyl(dimethyl)silyl]oxy}ethyl]-N-(3 methylbutyl)benzenesulfonamide N-[1-(4-bromothiophen-2-yl)-2-{[tert-butyl(dimethyl)silyl]oxy}ethyl]-3-methylbutan-1-amine (248 mg, 0.610 mmol) and DMAP (3.7 mg, 0.031 mmol) were dissolved in 2 mL pyridine and benzenesulfonyl chloride (234 µl, 1.830 mmol) was added. The resulting mixture was heated at 75° C. overnight, after which the mixture was cooled to room temperature, toluene was added and the mixture was concentrated in vacuo. The title compound was purified on silica gel (EtOAc/hexanes).

Step 6: N-[2-{[tert-butyl(dimethyl)silyl]oxy}-1-(4-formylthiophen-2-yl)ethyl]-N-(3-methylbutyl)benzenesulfonamide N-[1-(4-bromothiophen-2-yl)-2-{[tert-butyl(dimethyl)silyl]oxy}ethyl]-N-(3-methylbutyl)benzenesulfonamide (227 mg, 0.415 mmol) was dissolved in 4.1 mL THF and cooled to −78° C. n-BuLi (174 µl (2.5M in hexanes), 0.436 mmol) was added dropwise. The mixture was stirred 5 minutes and DMF (322 µL) was added in one portion. The mixture was stirred 20 minutes and then quenched with aqueous ammonium chloride. The quenched mixture was warmed to room temperature, DCM was added and the phases separated with a phase extractor. The solvent was removed under reduced pressure. The title compound was purified on silica gel (EtOAc/hexanes).

Step 7: N-[2-{[tert-butyl(dimethyl)silyl]oxy}-1-(4-{(E)-[(tert-butylsulfinyl)imino]methyl}thiophen-2-yl)ethyl]-N-(3-methylbutyl)benzenesulfonamide N-[2-{[tert-butyl(dimethyl)silyl]oxy}-1-(4-formylthiophen-2-yl)ethyl]-N-(3-methylbutyl)benzenesulfonamide (125 mg, 0.252 mmol) was dissolved in 0.84 mL THF. Titanium(IV) ethoxide (106 µl, 0.504 mmol) and 2-methylpropane-2-sulfinamide (36.7 mg, 0.303 mmol) were added. The mixture was stirred at room temperature overnight. The reac- Step 8: N-[2-{[tert-butyl(dimethyl)silyl]oxy}-1-(4-{[(tert-butylsulfinyl)amino]methyl}thiophen-2-yl)ethyl]-N-(3-methylbutyl)benzenesulfonamide N-[2-{[tert-butyl(dimethyl)silyl]oxy}-1-(4-{[(tert-butylsulfinyl)imino]methyl}thiophen-2-yl)ethyl]-N-(3-methylbutyl)benzenesulfonamide (146 mg, 0.244 mmol) was dissolved in 2.4 mL MeOH at −78° C. Sodium borohydride (11.99 mg, 0.317 mmol) was added and the mixture was then warmed to room temperature and stirred for 1 hour. The reaction was quenched slowly with saturated NaHCO₃, after which DCM was added and the phases separated with a phase extractor. The DCM was removed under reduced pressure.

Step 9: N-(1-[4-(aminomethyl)thiophen-2-yl]-2-{[tert-butyl(dimethyl)silyl]oxy}ethyl)-N-(3-methylbutyl)benzenesulfonamide N-[2-{[tert-butyl(dimethyl)silyl]oxy}-1-(4-{[(tert-butylsulfinyl)amino]-methyl}thiophen-2-yl)ethyl]-N-(3-methylbutyl)benzenesulfonamide (127 mg, 0.211 mmol) was dissolved in 2.1 mL MeOH. The mixture was cooled to 0° C. before the addition of HCl (0.264 mL of a 4 M solution in dioxane, 1.06 mmol). The mixture was stirred for 120 minutes and the solvents were removed by co-evaporation with toluene.

Step 10: N-[(5-{2-hydroxy-1-[(3-methylbutyl)(phenylsulfonyl)amino]ethyl}thiophen-3-yl)methyl]-Nα-(methoxycarbonyl)-β-phenyl-L-phenylalaninamide
(1)

Part A. N-(methoxycarbonyl)-β-phenyl-L-phenylalanine, which is of formula:

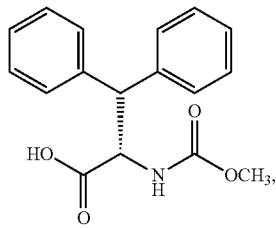 [SMILES: COC(=O)N[C@H](C(=O)O)C(c1ccccc1)c1ccccc1]

was prepared as follows: A suspension of L-diphenylalanine (13.87 g, 57.5 mmol) in THF (100 mL), and saturated NaHCO₃ (3 mL) being stirred at 0° C. was treated with neat methyl chloroformate (11.81 g, 125 mmol), stirred at 0° C. for 10 minutes and then at room temperature for 14 hours. 1 M HCl was then added and the mixture was extracted with DCM, dried over MgSO₄, filtered and concentrated to give the title compound as a white solid, which was used without further purification. MS: m/z=322.1 (MNa+).

Part B. The title compound was prepared as follows: To a mixture of N-(1-[4-(aminomethyl)thiophen-2-yl]-2-{[tert-butyl(dimethyl)silyl]oxy}ethyl)-N-(3-methylbutyl)benzenesulfonamide (87 mg, 0.227 mmol), N-(methoxycarbonyl)-β-phenyl-L-phenylalanine (75 mg, 0.250 mmol) and Hunig's base (131 μL, 0.751 mmol) in 2.3 mL DMF was added BOP reagent (111 mg, 0.25 mmol). The mixture was stirred at room temperature for 1 hour, and then quenched with saturated NaHCO₃. The aqueous layer was extracted 2× with EtOAc, the EtOAc layers were combined and washed 3 times with water, once with brine and dried (MgSO₄). The mixture was filtered, concentrated and purified on silica gel (EtOAc/hexanes). MS: m/z=686.2 (MNa+).

Example 2

N-[(2-{2-hydroxy-1-[(3-methylbutyl)(phenylsulfonyl)amino]ethyl}-1,3-thiazol-5-yl)methyl]-Nα-(methoxycarbonyl)-β-phenyl-L-phenylalaninamide
(2)

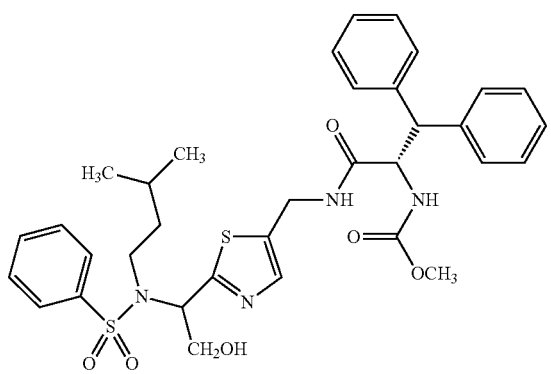 [SMILES: COC(=O)N[C@H](C(=O)NCc1cnc(C(CO)N(CCC(C)C)S(=O)(=O)c2ccccc2)s1)C(c1ccccc1)c1ccccc1]

The title compound was prepared in accordance with the procedure described in Example 1, except that 2-bromothiazole was used in place of 2,4-dibromothiophene in Step 1 and t-BuLi used in place of n-BuLi in Step 6. MS: m/z=665.2 ((MH+)).

Example 3

N-[(5-{2-hydroxy-1-[(3-methylbutyl)(phenylsulfonyl)amino]ethyl}-1,3-thiazol-2-yl)methyl]-Nα-(methoxycarbonyl)-β-phenyl-L-phenylalaninamide

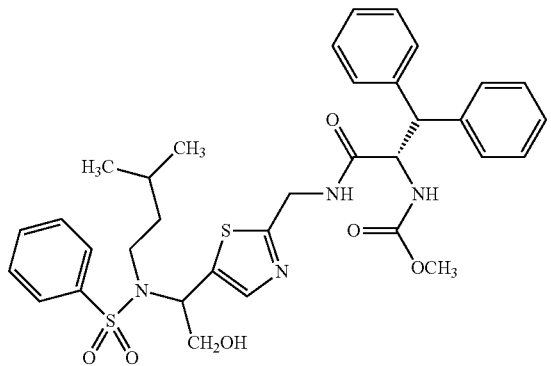 [SMILES: COC(=O)N[C@H](C(=O)NCc1ncc(C(CO)N(CCC(C)C)S(=O)(=O)c2ccccc2)s1)C(c1ccccc1)c1ccccc1]

The title compound was prepared in accordance with the procedure described in Example 1, except that 2-(trimethylsilyl)-1,3-thiazole was used in place of 2,4-dibromothiophene in Step 1. MS: m/z=665.2 ((MH+)).

Examples 4 and 5

The compounds shown in the table below were each prepared in accordance with the procedure described in Example 1.

| Example No. | Structure | Procedure | MS (m/z) |
|---|---|---|---|
| 4 | N-[(5-{2-hydroxy-1-[(3-methylbutyl)(phenylsulfonyl)amino]ethyl}thiophen-2-yl)methyl]-Nα-(methoxycarbonyl)-β-phenyl-L-phenylalaninamide | Example 1 using 2,5-dibromothiophene in Step 1 | 686.2 (MNa+) |
| 5 | N-[(5-{2-hydroxy-1-[{[4-(hydroxymethyl)phenyl]sulfonyl}(3-methylbutyl)amino]ethyl}thiophen-2-yl)methyl]-Nα-(methoxycarbonyl)-β-phenyl-L-phenylalaninamide | Example 4 using the appropriate sulfonyl chloride in Step 5 | 716.2 (MNa+) |

Example 6

N-[(4-{2-hydroxy-1-[(3-methylbutyl)(phenylsulfonyl)amino]ethyl}thiophen-2-yl)methyl]-Nα-(methoxycarbonyl)-β-phenyl-L-phenylalaninamide

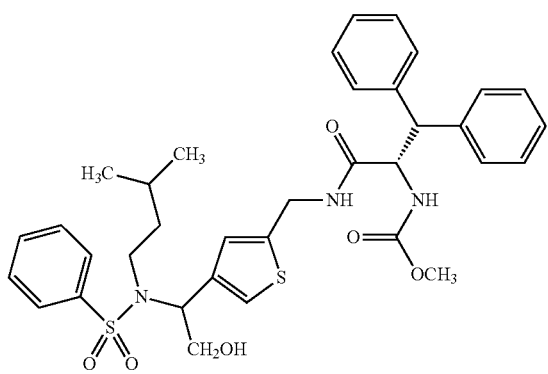 [SMILES: COC(=O)N[C@H](C(=O)NCc1cc(C(CO)N(CCC(C)C)S(=O)(=O)c2ccccc2)cs1)C(c1ccccc1)c1ccccc1]

Step 1
2-(4-bromothiophen-2-yl)-5,5-dimethyl-1,3-dioxane 4-bromothiophene-2-carbaldehyde (884 mg, 4.62 mmol), TsOH hydrate (44 mg, 0.231 mmol) and 2,2-dimethylpropane-1,3-diol (578 mg, 5.55 mmol) were dissolved in 9.2 mL benzene and refluxed in a Dean Stark apparatus for 5 hours. The mixture was cooled to 0° C. and aqueous sodium hydrogen carbonate was added. DCM was added and the phases separated with a phase extractor. The solvent was removed under reduced pressure to give the title compound.

Steps 2 to 6: Steps 2 to 6 are analogous to Steps 1 to 5 in Example 1

Step 7: N-[1-(5-formylthiophen-3-yl)-2-hydroxyethyl]-N-(3-methylbutyl)benzenesulfonamide N-{1-[5-(5,5-dimethyl-1,3-dioxan-2-yl)thiophen-3-yl]-2-hydroxyethyl}-N-(3-methylbutyl)benzenesulfonamide was dissolved in 10 mL AcOH/water (4:1) and stirred for 5 hours. 5 mL of water was and the aqueous layer was extracted 2× with EtOAc. The EtOAc layers were combined, washed 3 times with water, once with brine and dried (MgSO$_4$). The residue was purified on silica gel (EtOAc/hexanes).

Step 8-11: [(4-{2-hydroxy-1-[(3-methylbutyl)(phenylsulfonyl)amino]ethyl}thiophen-2-yl)methyl]-Nα-(methoxycarbonyl)-β-phenyl-L-phenylalaninamide (6)

The title compound was prepared via Steps 8-11 which are analogous to Steps 7-10 in Example 1. MS: m/z=686.1 (MNa$^+$).

Example 7

N-[1-(5-{2-hydroxy-1-[(3-methylbutyl)(phenylsulfonyl)amino]ethyl}thiophen-2-yl)ethyl]-Nα-(methoxycarbonyl)-β-phenyl-L-phenylalaninamide

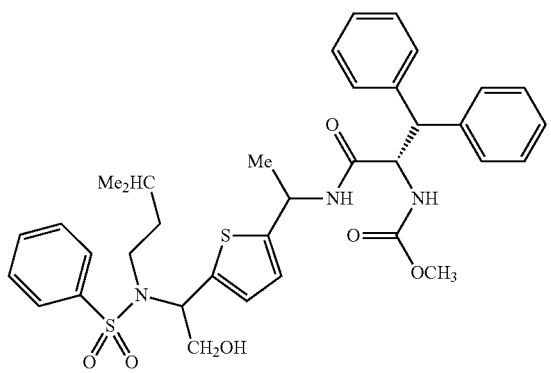

Steps 1 to 7: Steps 1 to 7 are the same as Steps 1 to 7 in Example 4

Step 8: N-[1-(5-{1-[(tert-butylsulfinyl)amino]ethyl}thiophen-2-yl)-2-hydroxyethyl]-N-(3-methylbutyl)benzenesulfonamide N-[2-{[tert-butyl(dimethyl)silyl]oxy}-1-(4-{(E)-[(tert-butylsulfinyl)imino]methyl}thiophen-2-yl)ethyl]-N-(3-methylbutyl)benzenesulfonamide (145 mg, 0.242 mmol) was dissolved in 2.4 mL THF at −0° C. MeMgBr (97 μL (3M in ether), 0.291 mmol) was added and the mixture was then warmed to room temperature and stirred for 2 hours. Another 0.5 eq of MeMgBr solution was added and the mixture was stirred at room temperature overnight. The reaction was quenched slowly with saturated NH₄Cl. DCM was added and the phases separated with a phase extractor. The DCM solvent was removed under reduced pressure. MS: m/z=700.2 (MNa+).

Procedures from steps 9 and 10 from Example 4 are then used to give the title compound.

Examples 8 and 9

The compounds shown in the table below were each prepared in accordance with the procedure described in Example 7.

| Example No. | Structure | Procedure | MS (m/z) |
|---|---|---|---|
| 8 | N-[1-(5-{2-hydroxy-1-[{[4-(hydroxymethyl)phenyl]sulfonyl}(3-methylbutyl)amino]ethyl}thiophen-2-yl)ethyl]-Nα-(methoxycarbonyl)-β-phenyl-L-phenylalaninamide | Example 7 using the appropriate sulfonyl chloride in Step 5 | 730.2 (MNa+) |
| 9 | N-[1-(5-{2-hydroxy-1-[{[4-(hydroxymethyl)phenyl]sulfonyl}(3-methylbutyl)amino]ethyl}thiophen-2-yl)propyl]-Nα-(methoxycarbonyl)-β-phenyl-L-phenylalaninamide | Example 7 using the ethylmagnesium bromide in Step 8 | 744.1 (MNa+) |

Example 10

N-({5-[(1R)-1-{[(4-aminophenyl)sulfonyl](2-methylpropyl)amino}-2-hydroxyethyl]thiophen-2-yl}methyl)-Nα-(methoxycarbonyl)-β-phenyl-L-phenylalaninamide

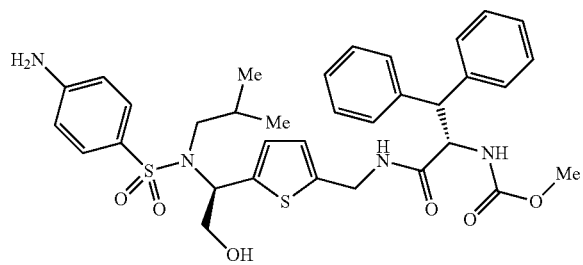 [SMILES: COC(=O)N[C@H](C(=O)NCc1ccc([C@@H](CO)N(CC(C)C)S(=O)(=O)c2ccc(N)cc2)s1)C(c1ccccc1)c1ccccc1]

Step 1: (7E)-2,2,3,3,10,10-hexamethyl-4-oxa-9-thionia-8-aza-3-silaundec-7-en-9-olate

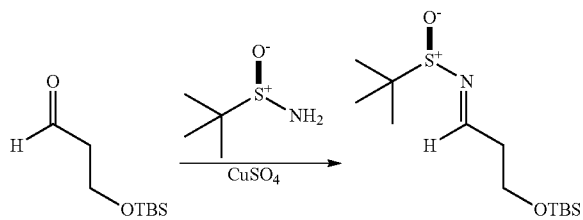

A three necked round bottom flask fitted with a mechanical stirrer, nitrogen inlet and temperature probe was charged with (S)-(−)-2-methyl-2-propanesulfinamide (113 g, 0.929 mol) and DCM (2.0 L) at room temperature (endotherm to 9° C.). Copper(II) sulfate (309 g, 1.94 mol) was then added followed by (tert-butyldimethylsilyl-oxy)acetaldehyde (150 g, 0.774 mol). After 36 hours the reaction mixture was filtered through a plug of Celite, the plug rinsed with DCM (3×200 mL), and the filtrate concentrated to provide the title compound as a light yellow syrup. The crude product was carried forward into the next step without further purification. $^1$H NMR (CDCl$_3$) δ 8.08 (1H, s), 4.56 (2H, s), 1.22 (9H, s), 0.95 (9H, s), 0.12 (6H, s).

Step 2: ((6R)-6-[5-(5,5-dimethyl-1,3-dioxan-2-yl)thiophen-2-yl]-2,2,3,3,9,9-hexamethyl-4-oxa-8-thionia-7-aza-3-siladecan-8-olate

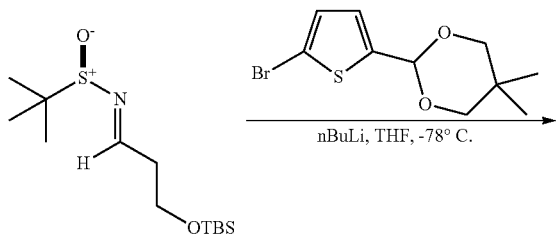

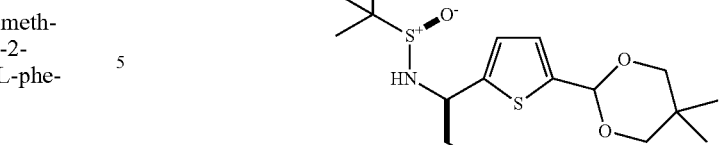

A solution of 2-(5-bromothiophen-2-yl)-5,5-dimethyl-1,3-dioxane (13.54 g, 48.9 mmol) in THF (163 mL) at −78° C. was treated with n-BuLi (32.6 mL, 48.9 mmol) and stirred for 30 minutes. This solution was cannulated into a solution of (7E)-2,2,3,3,10,10-hexamethyl-4-oxa-9-thionia-8-aza-3-silaundec-7-en-9-olate (9.04 g, 32.6 mmol) in CH$_2$Cl$_2$ at −78° C. After 45 minutes, NH$_4$Cl was added and the aqueous phase was extracted three times with ethyl acetate. The combined organics were washed with brine, dried and concentrated under reduce pressure. Purification on silica gel 10% to 60% EtOAc in hexane provided the title compound as a colorless oil. MS: m/z=476.5 ((MH+))

Step 3: (2R)-2-amino-2-[5-(5,5-dimethyl-1,3-dioxan-2-yl)thiophen-2-yl]ethanol hydrochloride

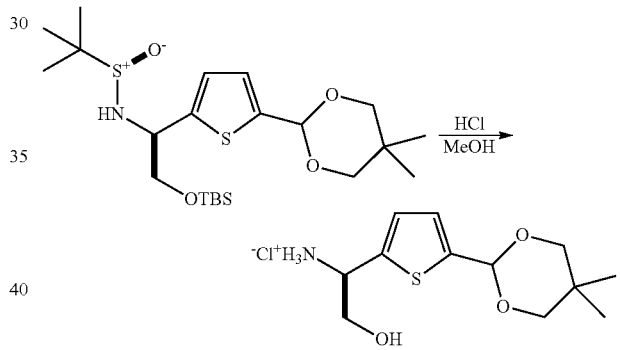

A solution of ((6R)-6-[5-(5,5-dimethyl-1,3-dioxan-2-yl)thiophen-2-yl]-2,2,3,3,9,9-hexamethyl-4-oxa-8-thionia-7-aza-3-siladecan-8-olate (12.7 g, 26.7 mmol) in MeOH (26 mL) cooled to 0° C. was treated with a 4 N hydrogen chloride solution (46.7 mL, 187 mmol) for 2 hours. The solvent was evaporated under reduced pressure, after which toluene was added and the co-solvent mixture was evaporated under reduce pressure to afford a white solid characterized as the title compound. $^1$H NMR ((CD$_3$)$_2$SO) δ 8.50 (1H), 7.17 (1H), 7.04 (1H), 5.70 (1H), 5.65 (1H), 4.53 (1H), 3.80-3.71 (2H), 3.65 (4H), 1.15 (3H), 0.73 (3H).

Step 4: Prop-2-en-1-yl[(1R)-1-(5-formylthiophen-2-yl)-2-hydroxyethyl]carbamate

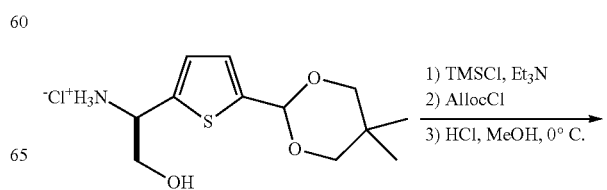

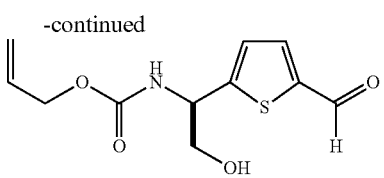

A solution of 2R)-2-amino-2-[5-(5,5-dimethyl-1,3-dioxan-2-yl)thiophen-2-yl]ethanol hydrochloride in dichloromethane (6.8 mL) was treated with triethylamine (0.57 mL, 4.08 mmol) and cooled to 0° C. Chlorotrimethyl silane (0.14 mL, 1.123 mmol) was added and, after stirring the mixture for 30 minutes, allyl chloroformate (0.11 mL, 1.072 mmol) was added. After the mixture was stirred overnight at room temperature, 1 N HCl (100 mL) and MeOH (50 mL) were added and the solution was stirred at room temperature overnight. EtOAc and water were then added and the phases were separated. The organic phase was washed with brine, dried and concentrated under reduced pressure. The crude product was used without further purification. $^1$H NMR ((CD3)$_2$CO) δ 9.90 (1H), 7.82 (1H), 7.25 (1H), 6.90 (1H), 5.96-5.87 (1H), 5.30 (1H), 5.15 (1H), 5.09 (1H), 4.52 (2H), 3.90 (2H), 3.39 (2H), 0.86 (3H).

Step 5: tert-Butyl[({5-[(1R)-2-hydroxy-1-{[(prop-2-en-1-yloxy)carbonyl]amino}ethyl]thiophen-2-yl}methyl)amino]sulfoniumolate

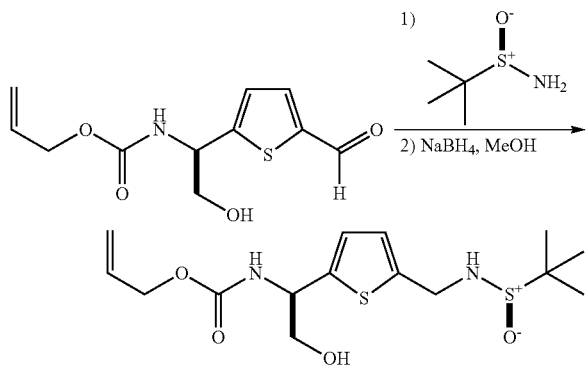

A solution of prop-2-en-1-yl[(1R)-1-(5-formylthiophen-2-yl)-2-hydroxyethyl]carbamate (700 mg, 2.74 mmol) in THF (1.3 mL) and toluene (26 mL) was treated with 2-methyl-2-propanesulfinamide (332 mg, 2.74 mmol) and KHSO$_3$ (659 mg, 5.48 mmol). After 18 hours, ethyl acetate and water were added and the phases separated. The organic phase was washed with brine, dried and concentrated under reduced pressure. MeOH (26 mL) was added to the crude organic concentrate and the solution was cooled to 0° C. After the addition of sodium borohydride (207 mg, 5.48 mmol) the mixture was stirred for 1 hour. NH$_4$Cl and ethyl acetate were then added and the phases separated. The organic phase was washed with brine, dried and concentrated. Purification on silica gel using 5% to 50% ethyl acetate in hexane provided the title compound as a colorless oil. $^1$H NMR ((CD$_3$)$_2$CO) δ 6.90 (1H), 6.80 (1H), 6.0-5.85 (1H), 5.30 (1H), 5.20 (1H), 5.05-4.95 (2H), 4.55 (2H), 4.43-4.21 (3H), 3.90-3.75 (2H), 1.20 (9H).

Step 6: Prop-2-en-1-yl{(1R)-1-[5-(aminomethyl)thiophen-2-yl]-2-hydroxyethyl}carbamate hydrogen chloride A solution of tert-butyl[({5-[(1R)-2-hydroxy-1-{[(prop-2-en-1-yloxy)carbonyl]amino}ethyl]thiophen-2-yl}methyl)amino]sulfoniumolate (700 mg, 1.94 mmol) in MeOH (19 mL) was treated with a 4 N hydrogen chloride solution (0.49 mL, 1.94 mmol) for 1 hour at room temperature. The solvent was evaporated under reduced pressure, after which toluene was added the co-solvents were evaporated solvent under reduce pressure to afford a white solid characterized as the title compound. $^1$H NMR (CD$_3$OD) δ 7.15 (1H), 7.00 (1H), 6.00 (1H), 5.35 (1H), 5.20 (1H), 4.92-4.89 (2H), 4.55 (1H), 4.26 (2H), 3.89-3.75 (3H).

Step 7: N-({5-[(1R)-2-hydroxy-1-{[(prop-2-en-1-yloxy)carbonyl]amino}ethylthiophen-2-yl}methyl)-Nα-(methoxycarbonyl)-β-phenyl-L-phenylalaninamide A solution of N-(methoxycarbonyl)-β-phenyl-L-phenylalanine (822 mg, 2.75 mmol) and prop-2-en-1-yl{(1R)-[5-(aminomethyl)thiophen-2-yl]-2-hydroxyethyl}carbamate hydrogen chloride (670 mg, 2.29 mmol) in DMF (23 mL) were treated with diisopropylethylamine (1.6 mL, 9.15 mmol) and BOP (1.2 g, 2.75 mmol) for 2 hours. Ethyl acetate and water were added and the phases were separated. The organic phase was washed with brine, dried and then concentrated under reduce pressure. The concentrate was then purified on silica gel using 5%-65% ethyl acetate in hexane provided the title compound. MS: m/z=538.8 ((MH+)).

Step 8: N-({5-[(1R)-1-amino-2-{[tert-butyl(dimethyl)silyl]oxy}ethyl]thiophen-2-yl}methyl)-Nα-(methoxycarbonyl)-β-phenyl-L-phenylalaninamide To a solution of N-({5-[(1R)-2-hydroxy-1-{[(prop-2-en-1-yloxy)carbonyl]amino}ethylthiophen-2-yl}methyl)-Nα-(methoxycarbonyl)-β-phenyl-L-phenylalaninamide (1.2 g, 2.23 mmol) in DMF (11 mL) was added TBDMSCl (0.44 g, 2.9 mmol) and imidazole (198 mg, 2.90 mmol) for 18 hours. EtOAc and water were then added and the resulting phases were separated. The organic phase was washed with brine, dried and concentrated under reduced pressure. The organic concentrate was purified on silica gel using 5%-65% ethyl acetate in hexane provided the title compound.

Step 9: N-({5-[(1R)-1-amino-2-{[tert-butyl(dimethyl)silyl]oxy}ethyl]thiophen-2-yl}methyl)-Nα-(methoxycarbonyl)-β-phenyl-L-phenylalaninamide

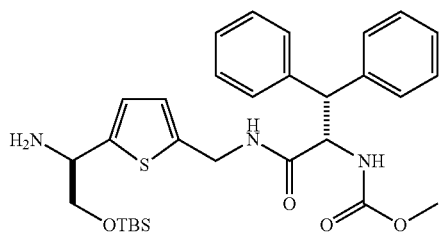 [SMILES: COC(=O)N[C@H](C(=O)NCc1ccc([C@H](N)CO[Si](C)(C)C(C)(C)C)s1)C(c1ccccc1)c1ccccc1]

A solution of prop-2-en-1-yl{(1R)-2-{[tert-butyl(dimethyl)silyl]oxy}-1-[5-({[N-(methoxycarbonyl)-β-phenyl-L-phenylalanyl]amino}methyl)thiophen-2-yl]ethyl}carbamate (1.2 g, 1.841 mmol) in dichloromethane (18.4 mL) was treated with phenylsilane (6.3 mL, 5.52 mmol) and Pd(PPh₃)₄ (106 mg, 0.092 mmol) for 1 hour at room temperature. Ethyl acetate and water were added and the phases were separated. The organic phase was washed with brine, dried, and then concentrated under reduced pressure. The concentrate was purified on silica gel using 5%-65% ethyl acetate in hexane to afford the title compound. ¹H NMR (CD₃OD) δ 7.40-7.15 (11H, 6.79 (1H), 6.40 (1H), 4.98 (1H), 4.38 (1H), 4.21 (2H), 3.82 (1H), 3.70 (1H), 3.52 (3H), 0.91 (9H), 0.10 (6H).

Step 10: N-({5-[(1R)-2-{[tert-butyl(dimethyl)silyl]oxy}-1-{[(4-nitrophenyl)sulfonyl]amino}ethyl]thiophen-2-yl}methyl)-Nα-(methoxycarbonyl)-β-phenyl-L-phenyl alaninamide

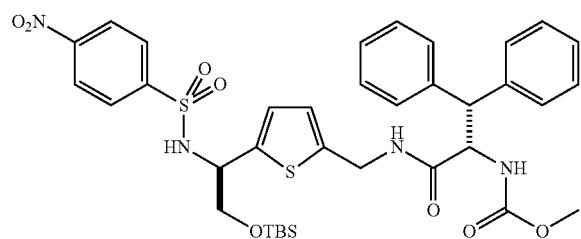 [SMILES: COC(=O)N[C@H](C(=O)NCc1ccc([C@@H](CO[Si](C)(C)C(C)(C)C)NS(=O)(=O)c2ccc([N+](=O)[O-])cc2)s1)C(c1ccccc1)c1ccccc1]

A solution of N-({5-[(1R)-1-amino-2-{[tert-butyl(dimethyl)silyl]oxy}ethyl]-thiophen-2-yl}methyl)-Nα-(methoxycarbonyl)-β-phenyl-L-phenylalaninamide (125 mg, 0.220 mmol) in dichloromethane (4.4 mL) was treated with diisopropylethylamine (0.046 mL, 0.264 mmol) and solid p-nitrobenzensulfonyl chloride (59 mg, 0.264 mmol) and the mixture was stirred at room temperature for 18 hours, quenched with saturated NaHCO₃ (0.5 mL), diluted with DCM, washed with sat. NaHCO₃, dried over MgSO₄, filtered and concentrated. The crude was purified on silica gel 10%-50% ethyl acetate in hexane to provide the title compound. ¹H NMR (CD3)₂CO) δ 8.39 (2H), 8.05 (2H), 7.67 (1H), 7.41 (5H), 7.30-7.15 (6H), 6.65 (1H), 6.42 (1H), 6.30 (1H), 5.10 (1H), 4.72 (1H), 4.50 (1H), 4.23 (1H), 4.13 (1H), 3.82 (2H), 3.49 (3H), 0.84 (9H), 0.01 (6H).

Step 11: N-({5-[(1R)-2-{[tert-butyl(dimethyl)silyl]oxy}-1-{(2-methylpropyl)[(4-nitrophenyl)sulfonyl]amino}ethyl]thiophen-2-yl}methyl)-Nα-(methoxycarbonyl)-β-phenyl-L-phenylalaninamide

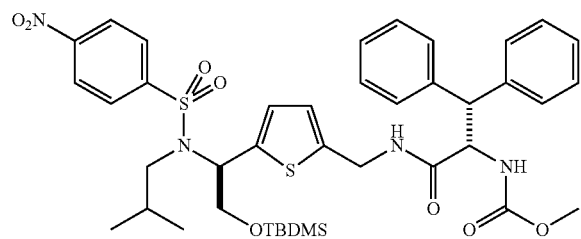 [SMILES: COC(=O)N[C@H](C(=O)NCc1ccc([C@@H](CO[Si](C)(C)C(C)(C)C)N(CC(C)C)S(=O)(=O)c2ccc([N+](=O)[O-])cc2)s1)C(c1ccccc1)c1ccccc1]

A solution of N-({5-[(1R)-2-{[tert-butyl(dimethyl)silyl]oxy}-1-{[(4-nitrophenyl)sulfonyl]amino}ethyl]thiophen-2-yl}methyl)-Nα-(methoxycarbonyl)-β-phenyl-L-phenyl alaninamide (60 mg, 0.080 mmol), Ph₃P (105 mg, 0.398 mmol), isobutanol (0.037 mL, 0.398 mmol) and DIAD (0.077 mL, 0.398 mmol) in THF (0.4 mL) stirred at 40° C. under N2 atmosphere, for 18 hours. Ethyl acetate and water were added and the phases were separated. The organic phase was washed with brine, dried, and concentrated under reduce pressure. The concentrate was purified on silica gel using 5%-65% ethyl acetate in hexane to afford the title compound with impurities. MS: m/z=810.3 ((MH+)).

Step 12: N-[(1S)-1-{5-[(1R)-1-{[(4-aminophenyl)sulfonyl](3,3-imethylbutyl)amino}-2-hydroxyethyl]thiophen-2-yl}-2,2,2-trifluoroethyl]-Nα-(methoxycarbonyl)-β-phenyl-L-phenylalaninamide A solution of N-({5-[(1R)-2-{[tert-butyl(dimethyl)silyl]oxy}-1-{(2-methylpropyl)[(4-nitrophenyl)sulfonyl]amino}ethyl]thiophen-2-yl}methyl)-Nα-(methoxycarbonyl)-β-phenyl-L-phenylalaninamide (100 mg, 0.124 mmol) in EtOH (1.2 mL), was added a 1.5 mL of a saturated solution of NH₄Cl and iron (138 mg, 2.47 mmol) and the mixture was stirred at 80° C. for 30 minutes. EtOAc (10 mL) and water (10 mL) were then added and the resulting phases were separated. The organic phase was washed with brine dried and concentrated. To the crude material in THF (2.0 mL) at 0° C. was added tetrabutylammonium fluoride (0.247 mL, 0.247 mmol). After 1 hour, ethyl acetate and water were added, and the phases were separated. The organic phase was washed with brine, dried over MgSO₄ and concentrated under reduced pressure. The concentrate was purified on silica gel using 10% to 80% ethyl acetate in hexane to afford the title compound as a white solid. MS: m/z=688.2 (MNa+). ¹H NMR δ (ppm) (CH₃COCH₃-d6): 7.60 (1H, s), 7.55 (2H, d, J=8.2 Hz), 7.41-7.33 (4H, m), 7.32-7.12 (6H, m), 6.77 (2H, d, J=8.2 Hz), 6.53 (1H, s), 6.40 (1H, d, J=9.2 Hz), 5.50 (1H, s), 5.11-5.02 (2H, m), 4.49 (1H, d, J=10.8 Hz), 4.24 (2H, d, J=4.9 Hz), 4.09-3.90 (3H, m), 3.50 (3H, s), 2.99 (1H, dd, J=14.1, 8.3 Hz), 2.65 91H, dd, J=14.2, 6.5 Hz), 1.85-1.80 (1H, m), 0.84 (3H, d, J=6.4 Hz), 0.79 (3H, d, J=6.4 Hz).

Examples 11 to 42

The compounds shown in the table below were each prepared in accordance with the procedure described in Example 10.

| Example No. | Structure | Procedure | MS (m/z) |
|---|---|---|---|
| 11 | N-({5-[(1R)-1-{[(4-aminophenyl)sulfonyl][(3,3-difluorocyclobutyl)methyl]amino}-2-hydroxyethyl]thiophen-2-yl}methyl)-Nα-(methoxycarbonyl)-β-phenyl-L-phenylalaninamide | Example 10 using the appropriate alcohol in Step 11 | 735.1 (MNa+) |
| 12 | N-({5-[(1R)-1-{[(4-aminophenyl)sulfonyl](propan-2-yl)amino}-2-hydroxyethyl]thiophen-2-yl}methyl)-Nα-(methoxycarbonyl)-β-phenyl-L-phenylalaninamide | Example 10 using the appropriate alcohol in Step 11 | 673.2 (MNa+) |
| 13 | N-({5-[(1R)-1-{[(4-aminophenyl)sulfonyl](1H-pyrrolo[2,3-b]pyridin-2-ylmethyl)amino}-2-hydroxyethyl]thiophen-2-yl}methyl)-Nα-(methoxycarbonyl)-β-phenyl-L-phenylalaninamide | Example 10 using the appropriate alcohol in Step 11 | 739.2 (MH+) |
| 14 | N-[(5-{(1R)-2-hydroxy-1-[{[3-(2-hydroxy-2-methylpropyl)phenyl]sulfonyl}(2-methylpropyl)phenyl]sulfonyl}(2-methylpropyl)amino]ethyl}thiophen-2-yl)methyl]-Nα-(methoxycarbonyl)-β-phenyl-L-phenylalaninamide | Example 10 using the appropriate sulfonyl chloride in Step 10 | 744.1 (MNa+) |

-continued

| Example No. | Structure | Procedure | MS (m/z) |
|---|---|---|---|
| 15 | N-({5-[(1R)-1-([[(3,3-difluorocyclobutyl)methyl]{[3-(2-hydroxy-2-methylpropyl)phenyl]sulfonyl}amino)-2-hydroxyethyl]thiophen-2-yl}methyl)-Nα-(methoxycarbonyl)-β-phenyl-L-phenylalaninamide | Example 10 using the appropriate sulfonyl chloride in Step 10 and the appropriate alcohol in Step 11 | 792.1 (MNa+) |
| 16 | Methyl {(2S)-1-[({5-[(1R)-1-{[(3,3-difluorocyclobutyl)methyl][(1-oxo-1,2-dihydroisoquinolin-6-yl)sulfonyl]amino}-2-hydroxyethyl]thiophen-2-yl}methyl)amino]-1-oxo-3,3-diphenylpropan-2-yl}carbamate | Example 10 using the appropriate sulfonyl chloride in Step 10 and the appropriate alcohol in Step 11 | 765.6 (MH+) |
| 17 | Methyl {(2S)-1-[({5-[(1R)-1-{[(3,3-difluorocyclobutyl)methyl](3,4-dihydro-1H-isochromen-6-ylsulfonyl)amino}-2-hydroxyethyl]thiophen-2-yl}methyl)amino]-1-oxo-3,3-diphenylpropan-2-yl}carbamate | Example 10 using the appropriate sulfonyl chloride in Step 10 and the appropriate alcohol in Step 11 | 776.0 (MNa+) |
| 18 | N-({5-[(1R)-1-{[(4-aminophenyl)sulfonyl][(4-methyl-1,2,5-oxadiazol-3-yl)methyl]amino}-2-hydroxyethyl]thiophen-2-yl}methyl)-Nα-(methoxycarbonyl)-β-phenyl-L-phenylalaninamide | Example 10 using the appropriate alcohol in Step 11 | 727.0 (MNa+) |

| Example No. | Structure | Procedure | MS (m/z) |
|---|---|---|---|
| 19 | N-({5-[(1R)-1-{[(4-aminophenyl)sulfonyl](1,2,5-oxadiazol-3-ylmethyl)amino}-2-hydroxyethyl]thiophen-2-yl}methyl)-Nα-(methoxycarbonyl)-β-phenyl-L-phenylalaninamide | Example 10 using the appropriate alcohol in Step 11 | 713.0 (MNa+) |
| 20 | N-({5-[(1R)-1-{[(4-aminophenyl)sulfonyl](1,2,5-oxadiazol-3-ylmethyl)amino}-2-hydroxyethyl]thiophen-2-yl}methyl)-Nα-(methoxycarbonyl)-β-phenyl-L-phenylalaninamide | Example 10 using the appropriate alcohol in Step 11 | 713.0 (MNa+) |
| 21 | N-[(5-{1-[(1,3-benzothiazol-5-ylsulfonyl)(propan-2-yl)amino]-2-hydroxyethyl}thiophen-2-yl)methyl]-Nα-(methoxycarbonyl)-β-phenyl-L-phenylalaninamide | Example 10 using the appropriate sulfonyl chloride in Step 10 and the appropriate alcohol in Step 11 | 715.2 (MNa+) |
| 22 | N-[(5-{(1R)-1-[(1,3-benzothiazol-6-ylsulfonyl)(2-methylpropyl)amino]-2-hydroxyethyl}thiophen-2-yl)methyl]-Nα-(methoxycarbonyl)-β-phenyl-L-phenylalaninamide | Example 10 using the appropriate sulfonyl chloride in Step 10 and the appropriate alcohol in Step 11 | 729.1 (MNa+) |

-continued

| Example No. | Structure | Procedure | MS (m/z) |
|---|---|---|---|
| 23 | N-[(5-{(1S)-1-[(1,3-benzothiazol-6-ylsulfonyl)(2-methylpropyl)amino]-2-hydroxyethyl}thiophen-2-yl)methyl]-Nα-(methoxycarbonyl)-β-phenyl-L-phenylalaninamide | Example 10 using the appropriate sulfonyl chloride in Step 10 and the appropriate alcohol in Step 11 | 729.1 (MNa+) |
| 24 | (+/-) N-[(5-{1-[(1,3-benzothiazol-6-ylsulfonyl)(1H-indol-3-ylmethyl)amino]-2-hydroxyethyl}thiophen-2-yl)methyl]-Nα-(methoxycarbonyl)-β-phenyl-L-phenylalaninamide | Example 10 using the appropriate sulfonyl chloride in Step 10 and the appropriate alcohol in Step 11 | 802.0 (MNa+) |
| 25 | N-[(5-{(1R)-1-[(1,3-benzothiazol-6-ylsulfonyl)(1H-indol-3-ylmethyl)amino]-2-hydroxyethyl}thiophen-2-yl)methyl]-Nα-(methoxycarbonyl)-β-phenyl-L-phenylalaninamide | Example 10 using the appropriate sulfonyl chloride in Step 10 and the appropriate alcohol in Step 11 | 802.2 (MNa+) |
| 26 | N-{[5-(1-{(1,3-benzothiazol-6-ylsulfonyl)[(2-methoxypyridin-3-yl)methyl]amino}-2-hydroxyethyl)thiophen-2-yl]methyl}-Nα-(methoxycarbonyl)-β-phenyl-L-phenylalaninamide | Example 10 using the appropriate sulfonyl chloride in Step 10 and the appropriate alcohol in Step 11 | 772 (MH+) |

-continued

| Example No. | Structure | Procedure | MS (m/z) |
|---|---|---|---|
| 27 | 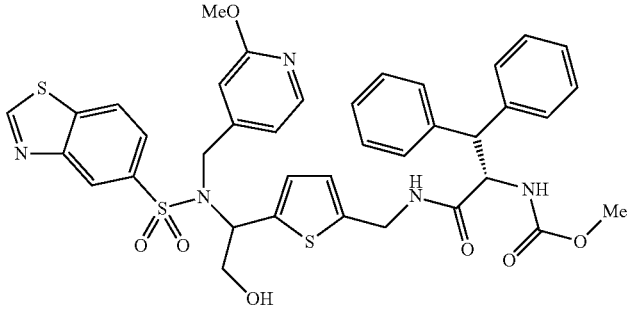<br>(+/−) N-{[5-(1-{[(1,3-benzothiazol-6-ylsulfonyl)[(2-methoxypyridin-4-yl)methyl]amino}-2-hydroxyethyl)thiophen-2-yl]methyl}-Nα-(methoxycarbonyl)-β-phenyl-L-phenylalaninamide | Example 10 using the appropriate sulfonyl chloride in Step 10 and the appropriate alcohol in Step 11 | 772.0 (MH+) |
| 28 | 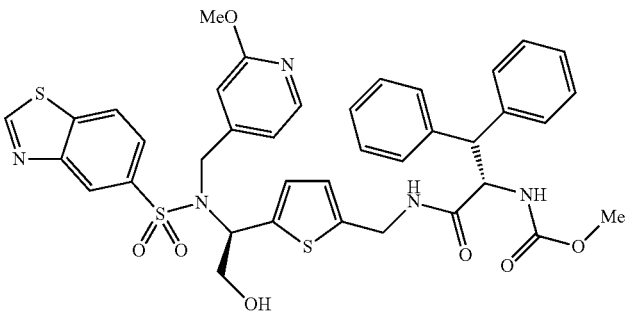<br>N-({5-[(1R)-1-{[(1,3-benzothiazol-6-ylsulfonyl)[(2-methoxypyridin-4-yl)methyl]amino}-2-hydroxyethyl]thiophen-2-yl}methyl)-Nα-(methoxycarbonyl)-β-phenyl-L-phenylalaninamide | Example 10 using the appropriate sulfonyl chloride in Step 10 and the appropriate alcohol in Step 11 | 772.0 (MH+) |
| 29 | 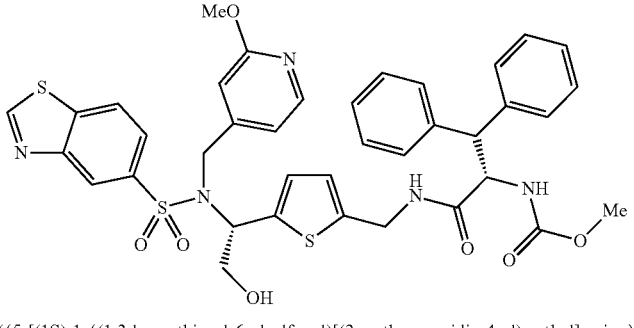<br>N-({5-[(1S)-1-{[(1,3-benzothiazol-6-ylsulfonyl)[(2-methoxypyridin-4-yl)methyl]amino}-2-hydroxyethyl]thiophen-2-yl}methyl)-Nα-(methoxycarbonyl)-β-phenyl-L-phenylalaninamide | Example 10 using the appropriate sulfonyl chloride in Step 10 and the appropriate alcohol in Step 11 | 772.0 (MH+) |
| 30 | 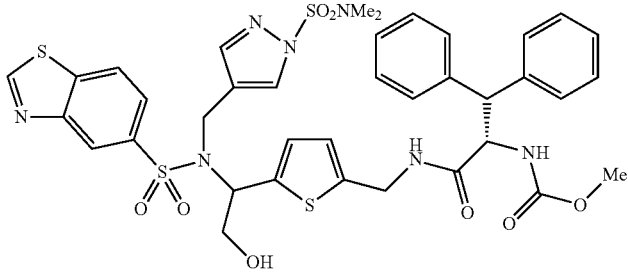<br>N-[(5-{1-[(1,3-benzothiazol-6-ylsulfonyl){[1-(dimethylsulfamoyl)-1H-pyrazol-4-yl]methyl}amino]-2-hydroxyethyl}thiophen-2-yl)methyl]-Nα-(methoxycarbonyl)-β-phenyl-L-phenylalaninamide | Example 10 using the appropriate sulfonyl chloride in Step 10 and the appropriate alcohol in Step 11 | 860.1 (MNa+) |

-continued

| Example No. | Structure | Procedure | MS (m/z) |
|---|---|---|---|
| 31 | (+/-) N-[(5-{1-[(1,3-benzothiazol-6-ylsulfonyl)(1H-pyrazol-4-ylmethyl)amino]-2-hydroxyethyl}thiophen-2-yl)methyl]-Nα-(methoxycarbonyl)-β-phenyl-L-phenylalaninamide | Example 10 using the appropriate sulfonyl chloride in Step 10 and the appropriate alcohol in Step 11 | 731.0 (MH+) |
| 32 | N-[(5-{(1R)-1-[(1,3-benzothiazol-6-ylsulfonyl)(1H-pyrazol-4-ylmethyl)amino]-2-hydroxyethyl}thiophen-2-yl)methyl]-Nα-(methoxycarbonyl)-β-phenyl-L-phenylalaninamide | Example 10 using the appropriate sulfonyl chloride in Step 10 and the appropriate alcohol in Step 11 | 731.0 (MH+) |
| 33 | N-[(5-{(1S)-1-[(1,3-benzothiazol-6-ylsulfonyl)(1H-pyrazol-4-ylmethyl)amino]-2-hydroxyethyl}thiophen-2-yl)methyl]-Nα-(methoxycarbonyl)-β-phenyl-L-phenylalaninamide | Example 10 using the appropriate sulfonyl chloride in Step 10 and the appropriate alcohol in Step 11 | 731.2 (MH+) |
| 34 | N-[(5-{1-[(1,3-benzothiazol-6-ylsulfonyl)(1H-pyrrolo[2,3-b]pyridin-2-ylmethyl)amino]-2-hydroxyethyl}thiophen-2-yl)methyl]-Nα-(methoxycarbonyl)-β-phenyl-L-phenylalaninamide | Example 10 using the appropriate sulfonyl chloride in Step 10 and the appropriate alcohol in Step 11 | 781.2 (MH+) |

| Example No. | Structure | Procedure | MS (m/z) |
|---|---|---|---|
| 35 | N-[(5-{(1R)-1-[(1,3-benzothiazol-6-ylsulfonyl)(1H-pyrrolo[2,3-b]pyridin-2-ylmethyl)amino]-2-hydroxyethyl}thiophen-2-yl)methyl]-Nα-(methoxycarbonyl)-β-phenyl-L-phenylalaninamide | Example 10 using the appropriate sulfonyl chloride in Step 10 and the appropriate alcohol in Step 11 | 781.2 (MH+) |
| 36 | (+/-) N-({5-[(1R)-1-{[(3,3-difluorocyclobutyl)methyl][(1-hydroxy-2,3-dihydro-1H-inden-5-yl)sulfonyl]amino}-2-hydroxyethyl]thiophen-2-yl}methyl)-Nα-(methoxycarbonyl)-β-phenyl-L-phenylalaninamide | Example 10 using the appropriate sulfonyl chloride in Step 10 and the appropriate alcohol in Step 11 | 776.2 (MNa+) |
| 37 | N-({5-[(1R)-1-{[(3,3-difluorocyclobutyl)methyl][(1-hydroxy-2,3-dihydro-1H-inden-5-yl)sulfonyl]amino}-2-hydroxyethyl]thiophen-2-yl}methyl)-Nα-(methoxycarbonyl)-β-phenyl-L-phenylalaninamide | Example 10 using the appropriate sulfonyl chloride in Step 10 and the appropriate alcohol in Step 11 | 776.2 (MNa+) |
| 38 | N-({5-[(1R)-1-{[(3,3-difluorocyclobutyl)methyl][(3-hydroxy-2,3-dihydro-1H-inden-5-yl)sulfonyl]amino}-2-hydroxyethyl]thiophen-2-yl}methyl)-Nα-(methoxycarbonyl)-β-phenyl-L-phenylalaninamide | Example 10 using the appropriate sulfonyl chloride in Step 10 and the appropriate alcohol in Step 11 | 776.0 (Mna+) |

-continued

| Example No. | Structure | Procedure | MS (m/z) |
|---|---|---|---|
| 39 | N-({5-[(1R)-1-{[(3,3-difluorocyclobutyl)methyl]({4-[(1R)-2,2,2-trifluoro-1-hydroxyethyl]phenyl}sulfonyl)amino}-2-hydroxyethyl]thiophen-2-yl}methyl)-Nα-(methoxycarbonyl)-β-phenyl-L-phenylalaninamide | Example 10 using the appropriate sulfonyl chloride in Step 10 and the appropriate alcohol in Step 11 | 797.2 (MH+) |
| 40 | N-({5-[(1R)-1-([(3,3-difluorocyclobutyl)methyl]{[3-(pyridin-2-ylcarbonyl)phenyl]sulfonyl}amino)-2-hydroxyethyl]thiophen-2-yl}methyl)-Nα-(methoxycarbonyl)-β-phenyl-L-phenylalaninamide | Example 10 using the appropriate sulfonyl chloride in Step 10 and the appropriate alcohol in Step 11 | 803.0 (MH+) |
| 41 | N-({5-[(1R)-1-{[(3,3-difluorocyclobutyl)methyl](1H-indol-5-ylsulfonyl)amino}-2-hydroxyethyl]thiophen-2-yl}methyl)-Nα-(methoxycarbonyl)-β-phenyl-L-phenylalaninamide | Example 10 using the appropriate sulfonyl chloride in Step 10 and the appropriate alcohol in Step 11 | 759.1 (MNa+) |
| 42 | N-({5-[(1R)-1-([(3,3-difluorocyclobutyl)methyl]{[3-(pyridin-2-ylmethyl)phenyl]sulfonyl}amino)-2-hydroxyethyl]thiophen-2-yl}methyl)-Nα-(methoxycarbonyl)-β-phenyl-L-phenylalaninamide | Example 10 using the appropriate sulfonyl chloride in Step 10 and the appropriate alcohol in Step 11 | 789.1 (MH+) |

| Example No. | Structure | Procedure | MS (m/z) |
|---|---|---|---|
| 43 | N-({5-[(1R)-1-{[(4-amino-3-fluorophenyl)sulfonyl][(3,3-difluorocyclobutyl)methyl]amino}-2-hydroxyethyl]thiophen-2-yl}methyl)-Nα-(methoxycarbonyl)-β-phenyl-L-phenylalaninamide | Example 10 using the appropriate sulfonyl chloride in Step 10 and the appropriate alcohol in Step 11 | 753.1 (MNa+) |

Example 44

N-[(1S)-1-{5-[(1R)-1-{[(4-aminophenyl)sulfonyl](3,3-dimethylbutyl)amino}-2-hydroxyethyl]thiophen-2-yl}-2,2,2-trifluoroethyl]-Nα-(methoxycarbonyl)-β-phenyl-L-phenylalaninamide

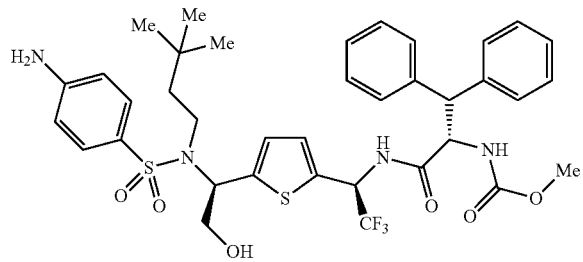 [SMILES: COC(=O)N[C@H](C(=O)N[C@H](c1ccc([C@@H](CO)N(CCC(C)(C)C)S(=O)(=O)c2ccc(N)cc2)s1)C(F)(F)F)C(c1ccccc1)c1ccccc1]

Step 1: (6R)-2,2,3,3,9,9-hexamethyl-6-(thiophen-2-yl)-4-oxa-8-thionia-7-aza-3-siladecan-8-olate A three necked round bottom flask fitted with a temperature probe, nitrogen inlet, mechanical stirrer and slow addition funnel was charged with N-[(1E)-2-{[tert-butyl(dimethyl)silyl]oxy}ethylidene]-2-methylpropane-2-sulfinamide (176 g, 0.530 mol) and DCM (2 L). At an internal temperature of −65° C., 2-thienyl lithium (1.0 M in THF) (0.794 L, 0.794 mol) was added dropwise such that the internal temperature was maintained <−65° C. The reaction mixture was stirred for 60 minutes, quenched at −65° C. with methanol (0.214 L, 5.30 mol), diluted with NH₄Cl (2 L) and warmed to room temperature. The layers were then separated and the aqueous layer was back extracted with DCM (2 L). The combined organic layers were dried over Na₂SO₄, filtered and concentrated. The crude concentrate was pre-loaded onto silica, divided into 4 batches, and purified by automated flash chromatography (4×1.5 kg SiO₂ columns, hexanes:EtOAc; 5% to 50% gradient over to provide the title compound as an amber oil. ¹H NMR ((CD₃)₂CO) δ 7.42 (1H, d, J=4.0 Hz), 7.14 (1H, s), 7.01 (1H, J=4.0, 3.5 Hz), 4.78-4.75 (1H, m), 4.48 (1H, s), 3.95-3.92 (1H, m), 3.86-3.82 (1H, m), 1.23 (9H, s), 0.94 (9H, s), 0.12 (6H, s).

Step 2: tert-Butyl{[(1E)-2,2,2-trifluoroethylidene]amino}sulfoniumolate

A three necked round bottom flask fitted with a magnetic stir bar, nitrogen inlet and reflux condenser was charged with (R)-(+)-2-methyl-2-propanesulfinamide (47.0 g, 0.388 mol), trifluoroacetaldehyde mono hydrate (75 wt % in water, 50.0 g, 0.323 mol) and DCM (400 mL). 4 Å sieves (200 g) were then added, and the mixture was heated to reflux in a 45° C. oil bath for 5 hours and then allowed to cool to room temperature. The reaction mixture was filtered, and the pad was washed with DCM. The DCM was concentrated to give a viscous yellow syrup, which was distilled (house vacuum=30 mmHg, oil bath=105° C.) to give the title compound as a clear liquid (bp=55° C. @ 30 mm Hg). ¹H NMR (CDCl₃) δ 8.02 (1H, bs), 1.29 (9H, s).

Step 3 (6R)-6-{5-[(1S)-1-{[tert-butyl(oxido)sulfonio]amino}-2,2,2-trifluoroethyl]thiophen-2-yl}-2,2,3,3,9,9-hexamethyl-4-oxa-8-thionia-7-aza-3-siladecan-8-olate A three necked round bottom flask fitted with a temperature probe, nitrogen inlet, mechanical stirrer and slow addition funnel was charged with (6R)-2,2,3,3,9,9-hexamethyl-6-(thiophen-2-yl)-4-oxa-8-thionia-7-aza-3-siladecan-8-olate (80.0 g, 0.217 mol) and THF (1.0 L). The mixture was cooled to an internal temperature of −25° C. and n-BuLi (2.5 M in hexanes, 234 mL, 0.585 mol) was added dropwise over 15 minutes (temperature between −25 and −22° C.). The reaction mixture was then stirred for 1 hour at −25° C. The orange solution was cooled to −65° C. and tert-Butyl{[(1E)-2,2,2-trifluoroethylidene]amino}sulfoniumolate (87.0 g, 0.434 mol) was added dropwise such that the internal temperature was maintained below 60° C. The reaction mixture was allowed to stir 10 minutes, and then quenched at −65° C. with methanol (88.0 mL, 2.17 mol). The orange solution was allowed to warm to room temperature. The solution was diluted with water (2.0 L) and cut. The aqueous phase was back extracted with MTBE (1.0 L). The combined organic phases were dried over Na₂SO₄, filtered and concentrated. The concentrate was purified by automated flash chromatography (1.5 kg SiO₂ column, hexanes:EtOAc; 50% to 100% gave a light yellow foam. The fractions containing a mixture of diastereomers were concentrated and purified by a second flash chromatography (1.5 kg SiO₂ column—same conditions as above) and combined to provide the title compound as a light yellow foam. ¹H NMR ((CD₃)₂CO) δ 7.19 (1H, d, J=3.5 Hz), 7.07 (1H, d, J=3.5 Hz), 5.41-5.29 (2H, m), 4.73 (1H, q, J=5.0 Hz), 4.50 (1H, s), 3.94 (1H, dd, J=10.0, 5.0 Hz), 3.85 (1H, dd, J=10.0, 7.0 Hz), 1.18 (9H, s), 1.17 (9H, s), 0.90 (9H, s), 0.08 (3H, s), 0.08 (3H, s).

Step 4: (2R)-2-amino-2-{5-[(1S)-1-amino-2,2,2-trifluoroethyl]thiophen-2-yl}ethanol dihydrochloride salt To a solution of (6R)-6-{5-[(1S)-1-{[tert-butyl(oxido)sulfonio]amino}-2,2,2-trifluoroethyl]thiophen-2-yl}-2,2,3,3,9,9-hexamethyl-4-oxa-8-thionia-7-aza-3-iladecan-8-late(4) tert-butyl[(2S,3E)-1-{[tert-butyl(diphenyl)silyl]oxy}-4-(2-nitrophenyl)-but-3-en-2-yl]carbamate (5.0 g, 8.88 mmol) in MeOH (89 mL) cooled to 0° C. was added 4 N hydrogen chloride solution (22.2 mL, 89 mmol) for 2 hours. Solvent was removed by evaporation under reduced pressure, toluene was added, and the co-solvents were evaporated under reduce pressure to render a white solid characterized as the title compound. ¹H NMR ((CD₃)₂CO) δ 7.42 (1H), 7.35 (1H), 5.82 (1H), 4.75 (1H), 3.97 (1H), 3.87 (1H).

Step 5: Prop-2-en-1-yl[(1R)-1-{5-[(1S)-1-amino-2,2,2-trifluoroethyl]thiophen-2-yl}-2-{[tert-butyl(dimethyl)silyl]oxy}ethyl]carbamate To a solution of (2R)-2-amino-2-{5-[(1S)-1-amino-2,2,2-trifluoroethyl]thiophen-2-yl}ethanol dihydrochloride salt (2.78 g, 8.88 mmol) in dichloromethane (49 mL) cooled to 0° C. was added Hunig's base (9.3 mL), 53.3 mmol). Allyl chloroformate (0.95 mL, 8.88 mmol) was then added and the mixture was stirred overnight at room temperature. t-butyldimethylsilylchloride (4.0 g, 26.6 mmol) and dimethylaminopyridine (0.11 g, 0.89 mmol) were then added to the solution and the solution was stirred overnight. Solvent was removed by evaporation and the resulting crude mixture was purified on silica eluting with 10% to 60% ethyl acetate in hexane to give the title compound as a colorless oil. MS: m/z=460.5 (MNa+).

Step 6: Prop-2-en-1-yl[(1R)-2-{[tert-butyl(dimethyl)silyl]oxy}-1-{5-[(1S)-2,2,2-trifluoro-1-{[N-(methoxycarbonyl)-b-phenyl-L-phenylalanyl]amino}ethyl]thiophen-2-yl}ethyl]carbamate To a solution of N-(methoxycarbonyl)-β-phenyl-L-phenylalanine (3.2 g, 10.6 mmol) in dichloromethane (70 mL) was cooled to −15° C., and then was added N-methylmorpholine (1.17 mL, 10.6 mmol) and isobutyl chloroformate and the mixture was stirred for 30 minutes. A solution of prop-2-en-1-yl[(1R)-1-{5-[(1S)-1-amino-2,2,2-trifluoroethyl]thiophen-2-yl}-2-{[tert-butyl(dimethyl)silyl]oxy}ethyl]carbamate (3.1 g, 7.07 mmol) and Hunig's base (1.48 mL, 8.48 mmol) in dichloromethane (70 mL) cooled to −15° C. was added to the mixed anhydride solution. The mixture was allowed to warm up to room temperature by stirring overnight. Sodium bicarbonate was added and the phases were separated using a phase separator and concentrated under reduced pressure. The crude was purified on silica gel using 10% to 60% ethyl acetate in hexane to provide the title compound as an oil. MS: m/z=742.2 (MNa+).

Step 7: N-[(1S)-1-{5-[(1R)-1-amino-2-{[tert-utyl(dimethyl)silyl]oxy}ethyl]thiophen-2-yl}-2,2,2-trifluoroethyl]-Nα-(methoxycarbonyl)-β-phenyl-L-phenylalaninamide A solution of prop-2-en-1-yl[(1R)-2-{[tert-butyl(dimethyl)silyl]oxy}-1-{5-[(1S)-2,2,2-trifluoro-1-{[N-(methoxycarbonyl)-b-phenyl-L-phenylalanyl]amino}ethyl]thiophen-2-yl}ethyl]carbamate (3.5 g, 4.86 mmol) in THF (97 mL) was cooled to 0° C. and PdP(Ph₃)₄ (0.56 g, 0.49 mmol) and morpholine (8.5 mL, 97.0 mmol) were added. After 3 hours the reaction mixture was concentrated and purified on an amino silica gel column using 10% to 75% ethyl acetate in hexane providing the title compound as a white solid. MS: m/z=619.2 (M-NH₂).

Step 8: N-{2-[(3S)-4-{[tert-butyl(diphenyl)silyl]oxy}-3-{(3-methylbutyl)[(4-nitrophenyl)sulfonyl]amino}butyl]phenyl}-Nα-(methoxycarbonyl)-β-phenyl-L-phenylalaninamide To a solution of N-[(1S)-1-{5-[(1R)-1-amino-2-{[tert-butyl(dimethyl)silyl]oxy}ethyl]thiophen-2-yl}-2,2,2-trifluoroethyl]-Nα-(methoxycarbonyl)-β-phenyl-L-phenylalaninamide (90 mg, 0.142 mmol) in dichloromethane (1.5 mL) was added triethylamine (0.024 mL, 0.170 mmol) and solid p-nitrobenzensulfonyl chloride (38 mg, 0.70 mmol) and the mixture was stirred at room temperature for 18 hours, quenched with saturated NaHCO₃ (0.5 mL), diluted with DCM, washed with saturated NaHCO₃, dried over MgSO₄, filtered and concentrated. The crude concentrate was purified on silica gel 10%-50% ethyl acetate in hexane to provide the title compound as a solid. MS m/z=843.9 (MNa+).

Step 9: N-[(1S)-1-{5-[(1R)-2-{[tert-butyl(dimethyl)silyl]oxy}-1-{(3,3-dimethyl butyl)[(4-nitrophenyl)sulfonyl]amino}ethyl]thiophen-2-yl}-2,2,2-trifluoroethyl]-Nα-(methoxycarbonyl)-β-phenyl-L-phenylalaninamide To a solution of N-{2-[(3S)-4-{[tert-butyl(diphenyl)silyl]oxy}-3-{(3-methylbutyl)[(4-nitrophenyl)sulfonyl]amino}butyl]phenyl}-Nα-(methoxycarbonyl)-β-phenyl-L-phenyl alaninamide (20 mg, 0.024 mmol), Ph₃P (38 mg, 0.146 mmol) and 3,3-dimethylbutan-1-ol (0.018 mL, 0.146 mmol) in THF (1.5 mL) stirred at an external temperature of 0° C. under N₂ atmosphere, was added neat DIAD (0.028 mL, 0.146 mmol) and the mixture stirred at the same temperature for 4 hours. The solution was then concentrated under reduced pressure and purified using 10% to 65% ethyl acetate in hexane to afford the title compound as an oil. MS: m/z=924.2 (MNa+).

Step 10: N-[(1S)-1-{5-[(1R)-1-{[(4-aminophenyl)sulfonyl](3,3-imethylbutyl)amino}-2-hydroxyethyl]thiophen-2-yl}-2,2,2-trifluoroethyl]-Nα-(methoxycarbonyl)-β-phenyl-L-phenylalaninamide To a solution of N-[(1S)-1-{5-[(1R)-2-{[tert-butyl(dimethyl)silyl]oxy}-1-{(3,3-dimethyl butyl)[(4-nitrophenyl)sulfonyl]amino}ethyl]thiophen-2-yl}-2,2,2-trifluoroethyl]-Nα-(methoxycarbonyl)-β-phenyl-L-phenylalaninamide (13 mg, 0.014 mmol) in EtOH (1.0 mL), was added a 1.5 mL of a saturated solution of NH₄Cl and iron (17 mg, 0.28 mmol) and the mixture was stirred at 80° C. for 30 minutes. EtOAc (10 mL) and water (10 mL) were then added, the phases were separated, and the organic phase was with brine, dried and concentrated. To the crude material in THF (2.0 mL) at 0° C. was added tetrabutylammonium fluoride (0.028 mL, 0.028 mmol). After stirring at 0° C. for 1 hour, ethyl acetate and water were added, and the resulting phases separated. The organic phase was washed with brine, dried over MgSO₄, concentrated under reduced pressure, and then purified on silica gel using 10% to 80% ethyl acetate in hexane provided the title compound as a white solid. MS: m/z=783.1 (MNa+). ¹H NMR δ (ppm) (CH₃SOCH₃-d₆): 9.28 (1H, d, J=9.2 Hz), 7.55 (1H, d, J=8.5 Hz), 7.46 (2H, d, J=8.5 Hz), 7.34-7.23 (6H, m), 7.15 (1H, t), 7.00-6.92 (3H, m), 6.66-6.61 (3H, m), 6.54 (1H, s), 6.01 (2H, s), 5.64-5.61 (1H, m), 5.21 (1H, t, J=9.8 Hz), 5.11 (1H, t, J=5.4 Hz), 5.02 (1H, d, J=6.5 Hz), 4.26 (1H, d, J=11.7 Hz), 3.83-3.77 (1H, m), 3.69-3.65 (1H, m), 3.43 (3H, s), 3.08-3.05 (1H, m), 2.90-2.85 (1H, m), 1.40-1.25 (2H, m), 0.75 (9H, s).

Examples 45 to 124

The compounds shown in the table below were each prepared in accordance with the procedure described in Example 44.

| Example No. | Structure | Procedure | MS (m/z) |
|---|---|---|---|
| 45 | 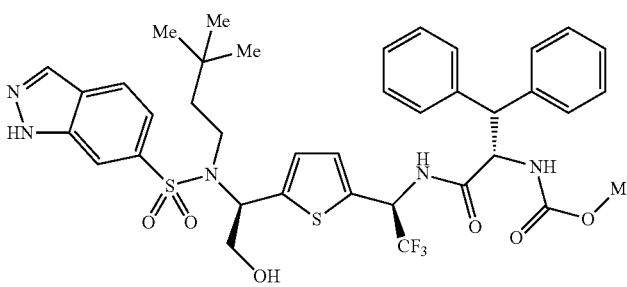 N-[(1S)-1-(5-{(1R)-1-[(3,3-dimethylbutyl)(1H-indazol-5-ylsulfonyl)amino]-2-hydroxyethyl}thiophen-2-yl)-2,2,2-trifluoroethyl]-Nα-(methoxycarbonyl)-β-phenyl-L-phenylalaninamide | Example 44 using the appropriate sulfonyl chloride in Step 8 | 808.2 (MNa+) |
| 46 | 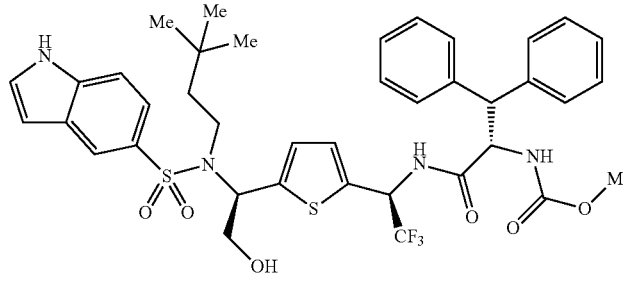 N-[(1S)-1-(5-{(1R)-1-[(3,3-dimethylbutyl)(1H-indol-6-ylsulfonyl)amino]-2-hydroxyethyl}thiophen-2-yl)-2,2,2-trifluoroethyl]-Nα-(methoxycarbonyl)-β-phenyl-L-phenylalaninamide | Example 44 using the appropriate sulfonyl chloride in Step 8 | 807.1 (MNa+) |
| 47 | 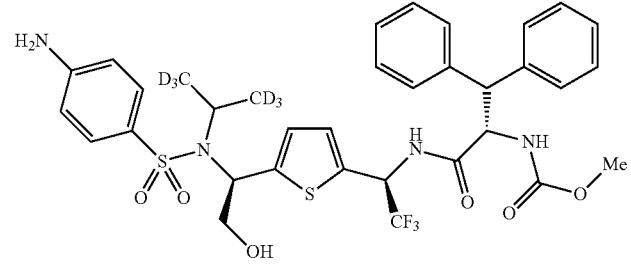 [SMILES: [2H]C([2H])([2H])C(N([C@H](CO)c1ccc([C@@H](NC(=O)[C@@H](NC(=O)OC)C(c2ccccc2)c2ccccc2)C(F)(F)F)s1)S(=O)(=O)c1ccc(N)cc1)C([2H])([2H])[2H]] N-[(1S)-1-{5-[(1R)-1-{[(4-aminophenyl)sulfonyl][(1,1,1,3,3,3-²H₆)propan-2-yl]amino}-2-hydroxyethyl]thiophen-2-yl}-2,2,2-trifluoroethyl]-Nα-(methoxycarbonyl)-β-phenyl-L-phenylalaninamide | Example 44 using the appropriate alcohol in Step 9 | 748.2 (MNa+) |

-continued

| Example No. | Structure | Procedure | MS (m/z) |
|---|---|---|---|
| 48 | N-[(1S)-1-{5-[(1R)-1-{[(5-chlorothiophen-2-yl)sulfonyl](propan-2-yl)amino}-2-hydroxyethyl]thiophen-2-yl}-2,2,2-trifluoroethyl]-Nα-(methoxycarbonyl)-β-phenyl-L-phenylalaninamide | Example 44 using the appropriate sulfonyl chloride in Step 8 and the appropriate alcohol in Step 9 | 619.2 (M-thiophene) |
| 49 | (βS)-N-[(1S)-1-{5-[(1R)-1-{[(4-aminophenyl)sulfonyl](propan-2-yl)amino}-2-hydroxyethyl]thiophen-2-yl}-2,2,2-trifluoroethyl]-Nα-(methoxycarbonyl)-β-1H-pyrrolo[2,3-b]pyridin-3-yl-L-phenylalaninamide | Example 44 using the appropriate alcohol in Step 9 | 780.4 (MNa+) |
| 50 | N-[(1S)-1-{5-[(1R)-1-{[(5-aminothiophen-2-yl)sulfonyl](propan-2-yl)amino}-2-hydroxyethyl]thiophen-2-yl}-2,2,2-trifluoroethyl]-Nα-(methoxycarbonyl)-β-phenyl-L-phenylalaninamide | Example 44 using the appropriate sulfonyl chloride in Step 8 and the appropriate alcohol in Step 9 | 725.0 (MH+) |
| 51 | N-[(1S)-1-(5-{(1R)-1-[(3,3-dimethylbutyl)(imidazo[1,2-c]pyridin-7-ylsulfonyl)amino]-2-hydroxyethyl}thiophen-2-yl)-2,2,2-trifluoroethyl]-Nα-(methoxycarbonyl)-β-phenyl-L-phenylalaninamide | Example 44 using the appropriate sulfonyl chloride in Step 8 | 786.1 (MH+) |

| Example No. | Structure | Procedure | MS (m/z) |
|---|---|---|---|
| 52 | N-[(1S)-1-(5-{(1R)-1-[{[3,5-difluoro-4-(hydroxymethyl)phenyl]sulfonyl}(3,3-dimethylbutyl)amino]-2-hydroxyethyl}thiophen-2-yl)-2,2,2-trifluoroethyl]-Nα-(methoxycarbonyl)-β-phenyl-L-phenylalaninamide | Example 44 using the appropriate sulfonyl chloride in Step 8 | 834.1 (MNa+) |
| 53 | N-[(1S)-1-(5-{(1R)-1-[(3,3-dimethylbutyl){[4-(hydroxymethyl)phenyl]sulfonyl}amino]-2-hydroxyethyl}thiophen-2-yl)-2,2,2-trifluoroethyl]-Nα-(methoxycarbonyl)-β-phenyl-L-phenylalaninamide | Example 44 using the appropriate sulfonyl chloride in Step 8 | 798.1 (MNa+) |
| 54 | N-[(1S)-1-{5-[(1R)-1-{[(4-aminothiophen-2-yl)sulfonyl](propan-2-yl)amino}-2-hydroxyethyl]thiophen-2-yl)-2,2,2-trifluoroethyl]-Nα-(methoxycarbonyl)-β-phenyl-L-phenylalaninamide | Example 44 using the appropriate sulfonyl chloride in Step 8 and the appropriate alcohol in Step 9 | 767.2 (MH+) |
| 55 | N-[(1S)-1-(5-{(1R)-1-[(3,3-dimethylbutyl)(1H-indol-2-ylsulfonyl)amino]-2-hydroxyethyl}thiophen-2-yl)-2,2,2-trifluoroethyl]-Nα-(methoxycarbonyl)-β-phenyl-L-phenylalaninamide | Example 44 using the appropriate sulfonyl chloride in Step 8 | 807.1 (MNa+) |

| Example No. | Structure | Procedure | MS (m/z) |
|---|---|---|---|
| 56 | N-[(1S)-1-(5-{(1R)-1-[(3,3-dimethylbutyl){[4-(hydroxymethyl)-3-(trifluoromethyl)phenyl]sulfonyl}amino]-2-hydroxyethyl}thiophen-2-yl)-2,2,2-trifluoroethyl]-Nα-(methoxycarbonyl)-β-phenyl-L-phenylalaninamide | Example 44 using the appropriate sulfonyl chloride in Step 8 | 866.1 (MNa+) |
| 57 | N-[(1S)-1-{5-[(1R)-1-{[(5-aminopyridin-2-yl)sulfonyl](3,3-dimethylbutyl)amino}-2-hydroxyethyl]thiophen-2-yl}-2,2,2-trifluoroethyl]-Nα-(methoxycarbonyl)-β-phenyl-L-phenylalaninamide | Example 44 using the appropriate sulfonyl chloride in Step 8 | 762.1 (MH+) |
| 58 | N-[(1S)-1-(5-{(1R)-1-[(1,2,3-benzothiadiazol-6-ylsulfonyl)(3,3-dimethylbutyl)amino]-2-hydroxyethyl}thiophen-2-yl)-2,2,2-trifluoroethyl]-Nα-(methoxycarbonyl)-β-phenyl-L-phenylalaninamide | Example 44 using the appropriate sulfonyl chloride in Step 8 | 826.0 (MNa+) |
| 59 | N-[(1S)-1-(5-{(1R)-1-[(3,3-dimethylbutyl)(1H-indol-4-ylsulfonyl)amino]-2-hydroxyethyl}thiophen-2-yl)-2,2,2-trifluoroethyl]-Nα-(methoxycarbonyl)-β-phenyl-L-phenylalaninamide | Example 44 using the appropriate sulfonyl chloride in Step 8 | 785.0 (MH+) |

| Example No. | Structure | Procedure | MS (m/z) |
| --- | --- | --- | --- |
| 60 | N-[(1S)-1-{5-[(1R)-1-{[(4-aminophenyl)sulfonyl](2-methylpropyl)amino}-2-hydroxyethyl]thiophen-2-yl}-2,2,2-trifluoroethyy]-Nα-(methoxycarbonyl)-β-phenyl-L-phenylalaninamide | Example 44 using the appropriate alcohol in Step 9 | 755.0 (MNa+) |
| 61 | N-[(1R)-1-{5-[(1R)-1-{[(4-aminophenyl)sulfonyl](2-methylpropyl)amino}-2-hydroxyethyl]thiophen-2-yl}-2,2,2-trifluoroethyl]-Nα-(methoxycarbonyl)-β-phenyl-L-phenylalaninamide | Example 44 using the appropriate alcohol in Step 9 | 755.0 (MNa+) |
| 62 | N-[(1S)-1-{5-[(1R)-1-1[(4-aminophenyl)sulfonyl](ethyl)amino}-2-hydroxyethyl]thiophen-2-yl}-2,2,2-trifluoroethyl]-Nα-(methoxycarbonyl)-β-phenyl-L-phenylalaninamide | Example 44 using the appropriate alcohol in Step 9 | 727.2 (MNa+) |
| 63 | N-[(S)-{[4(1R)-1-{[(4-aminophenyl)sulfonyl](2-methylpropyl)amino}-2-hydroxyethyl]thiophen-2-yl}(cyclopropyl)methyl]-Nα-(methoxycarbonyl)-β-phenyl-L-phenylalaninamide | Example 44 using the appropriate alcohol in Step 9 | 727.2 (MNa+) |

-continued

| Example No. | Structure | Procedure | MS (m/z) |
|---|---|---|---|
| 64 | N-[2-(5-{2-hydroxy-1-[(3-methylbutyl)(phenylsulfonyl)amino]ethyl}thiophen-2-yl)propan-2-yl]-Nα-(methoxycarbonyl)-(3-phenyl-L-phenylalaninamide | Example 44 using the appropriate sulfonyl chloride in Step 8 and the appropriate alcohol in Step 9 | 714.1 (MNa+) |
| 65 | Nα-(methoxycarbonyl)-β-phenyl-N-[(1S)-2,2,2-trifluoro-1-(5-{(1R)-2-hydroxy-1-[{[4-(hydroxymethyl)phenyl]sulfonyl}(propan-2-yl)amino]ethyl}thiophen-2-yl)ethyl]-L-phenylalaninamide | Example 44 using the appropriate sulfonyl chloride in Step 8 and the appropriate alcohol in Step 9 | 756.1 (MNa+) |
| 66 | N-({5-[(1R)-1-([(3,3-difluorocyclobutyl)methyl]{[4-(1-hydroxyethyl)phenyl]sulfonyl}amino)-2-hydroxyethyl]thiophen-2-yl}methyl)-Nα-(methoxycarbonyl)-β-phenyl-L-phenylalaninamide | Example 44 using the appropriate sulfonyl chloride in Step 8 and the appropriate alcohol in Step 9 | 778.2 (MNa+) |
| 67 | N-({5-[(1R)-1-{[(4-acetylphenyl)sulfonyl][(3,3-difluorocyclobutyl)methyl]amino}-2-hydroxyethyl]thiophen-2-yl}methyl)-Nα-(methoxycarbonyl)-β-phenyl-L-phenylalaninamide | Example 44 using the appropriate sulfonyl chloride in Step 8 and the appropriate alcohol in Step 9 | 776.1 (MNa+) |

| Example No. | Structure | Procedure | MS (m/z) |
|---|---|---|---|
| 68 | N-{(1S)-1-[5-(1-{(3,3-dimethylbutyl)[(6-methoxypyridin-3-yl)sulfonyl]amino}-2-hydroxyethyl)thiophen-2-yl]-2,2,2-trifluoroethyl}-Nα-(methoxycarbonyl)-β-phenyl-L-phenylalaninamide | Example 44 using the appropriate sulfonyl chloride in Step 8 | 843.1 (MNa+) |
| 69 | N-[(1S)-1-{5-[(1R)-1-{(3,3-dimethylbutyl)[(6-oxo-1,6-dihydropyridin-3-yl)sulfonyl]amino}-2-hydroxyethyl]thiophen-2-yl}-2,2,2-trifluoroethyl]-Nα-(methoxycarbonyl)-β-phenyl-L-phenylalaninamide | Example 44 using the appropriate sulfonyl chloride in Step 8 | 899.2 (MNa+) |
| 70 | N-[(1S)-1-(5-{1-[(3,3-dimethylbutyl)({4-[(methoxycarbonyl)amino]phenyl}sulfonyl)amino]-2-hydroxyethyl}thiophen-2-yl)-2,2,2-trifluoroethyl]-Nα-(methoxycarbonyl)-β-phenyl-L-phenylalaninamide | Example 44 using the appropriate sulfonyl chloride in Step 8 | 841.2 (MNa+) |
| 71 | N-[(1S)-1-(5-{(1R)-1-[(3,3-dimethylbutyl)(imidazo[1,2-a]pyridin-6-ylsulfonyl)amino]-2-hydroxyethyl}thiophen-2-yl)-2,2,2-trifluoroethyl]-Nα-(methoxycarbonyl)-β-phenyl-L-phenylalaninamide | Example 44 using the appropriate sulfonyl chloride in Step 8 | 786.2 (MH+) |

| Example No. | Structure | Procedure | MS (m/z) |
|---|---|---|---|
| 72 | N-[(1S)-1-{5-[(1R)-1-{[(3-chloro-3a,7a-dihydro-1H-indol-6-yl)sulfonyl](3,3-dimethylbutyl)amino}-2-hydroxyethyl]thiophen-2-yl}-2,2,2-trifluoroethyl]-Nα-(methoxycarbonyl)-β-phenyl-L-phenylalaninamide | Example 44 using the appropriate sulfonyl chloride in Step 8 | 814.2 (MNa+) |
| 73 | Methyl [(2S)-1-{[(1S)-1-(5-{(1R)-1-[(3,3-dimethylbutyl)(quinolin-6-ylsulfonyl)amino]-2-hydroxyethyl}thiophen-2-yl)-2,2,2-trifluoroethyl]amino}-1-oxo-3,3-diphenylpropan-2-yl]carbamate | Example 44 using the appropriate sulfonyl chloride in Step 8 | 797.2 (MH+) |
| 74 | N-[(1S)-1-(5-{(1R)-1-[(1H-benzimidazol-6-ylsulfonyl)(3,3-dimethylbutyl)amino]-2-hydroxyethyl}thiophen-2-yl)-2,2,2-trifluoroethyl]-Nα-(methoxycarbonyl)-β-phenyl-L-phenylalaninamide | Example 44 using the appropriate sulfonyl chloride in Step 8 | 786.1 (MH+) |
| 75 | N-[(1S)-1-{5-[(1R)-1-{[(4-aminophenyl)sulfonyl](propan-2-yl)amino}-2-hydroxyethyl]thiophen-2-yl}ethyl]-Nα-(methoxycarbonyl)-β-phenyl-L-phenylalaninamide | Example 44 using the appropriate alcohol in Step 9 | 687.1 (MNa+) |

-continued

| Example No. | Structure | Procedure | MS (m/z) |
|---|---|---|---|
| 76 | N-[(1S)-1-{5-[(1R)-1-{[(4-aminophenyl)sulfonyl](2-methylpropyl)amino}-2-hydroxyethyl]thiophen-2-yl}ethyl]-Nα-(methoxycarbonyl)-β-phenyl-L-phenylalaninamide | Example 44 using the appropriate alcohol in Step 9 | 701.2 (MNa+) |
| 77 | N-[(1S)-1-{5-[(1R)-1-{[(4-aminophenyl)sulfonyl](propan-2-yl)amino}-2-hydroxyethyl]thiophen-2-yl}-2,2,2-trifluoroethyl]-Nα-(methoxycarbonyl)-β-phenyl-L-phenylalaninamide | Example 44 using the appropriate alcohol in Step 9 | 741.1 (MNa+) |
| 78 | Nα-(methoxycarbonyl)-β-phenyl-N-[(1S)-2,2,2-trifluoro-1-(5-{(1R)-2-hydroxy-1-[(1H-indol-5-ylsulfonyl)(propan-2-yl)amino]ethyl}thiophen-2-yl)ethyl]-L-phenylalaninamide | Example 44 using the appropriate sulfonyl chloride in Step 8 and the appropriate alcohol in Step 9 | 765.1 (MNa+) |
| 79 | Nα-(methoxycarbonyl)-β-phenyl-N-[(1S)-2,2,2-trifluoro-1-(5-{(1R)-2-hydroxy-1-[(1H-indol-6-ylsulfonyl)(propan-2-yl)amino]ethyl}thiophen-2-yl)ethyl]-L-phenylalaninamide | Example 44 using the appropriate sulfonyl chloride in Step 8 and the appropriate alcohol in Step 9 | 765.0 (MNa+) |

| Example No. | Structure | Procedure | MS (m/z) |
|---|---|---|---|
| 80 | N-[(1S)-1-{5-[(1R)-1-{[(4-amino-3-fluorophenyl)sulfonyl](propan-2-yl)amino}-2-hydroxyethyl]thiophen-2-yl}-2,2,2-trifluoroethyl]-Nα-(methoxycarbonyl)-β-phenyl-L-phenylalaninamide | Example 44 using the appropriate sulfonyl chloride in Step 8 and the appropriate alcohol in Step 9 | 759.1 (MNa+) |
| 81 | Nα-(methoxycarbonyl)-β-phenyl-N-[(1S)-2,2,2-trifluoro-1-(5-{(1R)-2-hydroxy-1-[(1H-indazol-6-ylsulfonyl)(propan-2-yl)amino]ethyl}thiophen-2-yl)ethyl]-L-phenylalaninamide | Example 44 using the appropriate sulfonyl chloride in Step 8 and the appropriate alcohol in Step 9 | 744.1 (MH+) |
| 82 | N-[(1S)-1-{5-[(1R)-1-{[(4-amino-3-chlorophenyl)sulfonyl](propan-2-yl)amino}-2-hydroxyethyl]thiophen-2-yl}-2,2,2-trifluoroethyl]-Nα-(methoxycarbonyl)-β-phenyl-L-phenylalaninamide | Example 44 using the appropriate sulfonyl chloride in Step 8 and the appropriate alcohol in Step 9 | 775.0 (MH+) |
| 83 | N-[(1S)-1-{5-[(1R)-1-{[(4-aminophenyl)sulfonyl](3-methylbutyl)amino}-2-hydroxyethyl]thiophen-2-yl}-2,2,2-trifluoroethyl]-Nα-(methoxycarbonyl)-β-phenyl-L-phenylalaninamide | Example 44 using the appropriate alcohol in Step 9 | 769.0 (MNa+) |

-continued

| Example No. | Structure | Procedure | MS (m/z) |
|---|---|---|---|
| 84 | 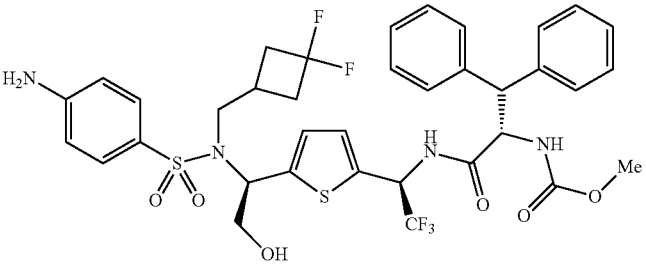 [SMILES: COC(=O)N[C@H](C(=O)N[C@H](c1ccc([C@@H](CO)N(CC2CC(F)(F)C2)S(=O)(=O)c2ccc(N)cc2)s1)C(F)(F)F)C(c1ccccc1)c1ccccc1]<br>N-[(1S)-1-{5-[(1R)-1-{[(4-aminophenyl)sulfonyl][(3,3-difluorocyclobutyl)methyl]amino}-2-hydroxyethyl]thiophen-2-yl}-2,2,2-trifluoroethyl]-Nα-(methoxycarbonyl)-β-phenyl-L-phenylalaninamide | Example 44 using the appropriate alcohol in Step 9 | 803.0 (MNa+) |
| 85 | 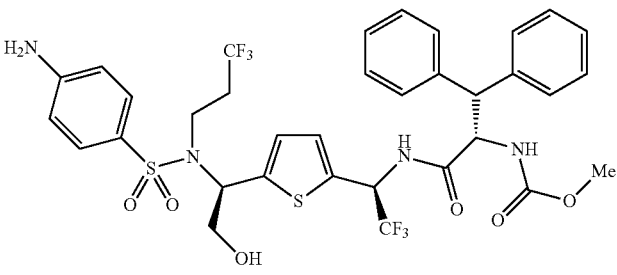 [SMILES: COC(=O)N[C@H](C(=O)N[C@H](c1ccc([C@@H](CO)N(CCC(F)(F)F)S(=O)(=O)c2ccc(N)cc2)s1)C(F)(F)F)C(c1ccccc1)c1ccccc1]<br>N-[(1S)-1-{5-[(1R)-1-{[(4-aminophenyl)sulfonyl](3,3,3-trifluoropropyl)amino}-2-hydroxyethyl]thiophen-2-yl}-2,2,2-trifluoroethyl]-Nα-(methoxycarbonyl)-β-phenyl-L-phenylalaninamide | Example 44 using the appropriate alcohol in Step 9 | 795.1 (MNa+) |
| 86 | 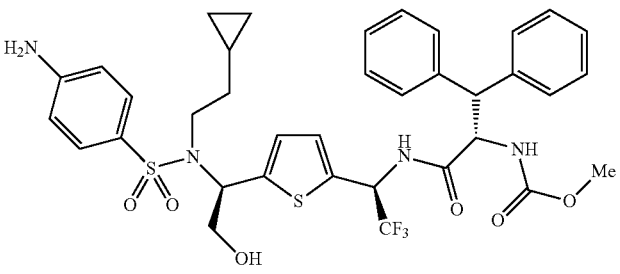 [SMILES: COC(=O)N[C@H](C(=O)N[C@H](c1ccc([C@@H](CO)N(CCC2CC2)S(=O)(=O)c2ccc(N)cc2)s1)C(F)(F)F)C(c1ccccc1)c1ccccc1]<br>N-[(1S)-1-{5-[(1R)-1-{[(4-aminophenyl)sulfonyl](2-cyclopropylethyl)amino}-2-hydroxyethyl]thiophen-2-yl}-2,2,2-trifluoroethyl]-Nα-(methoxycarbonyl)-(3-phenyl-L-phenylalaninamide | Example 44 using the appropriate alcohol in Step 9 | 768.1 (MNa+) |
| 87 | 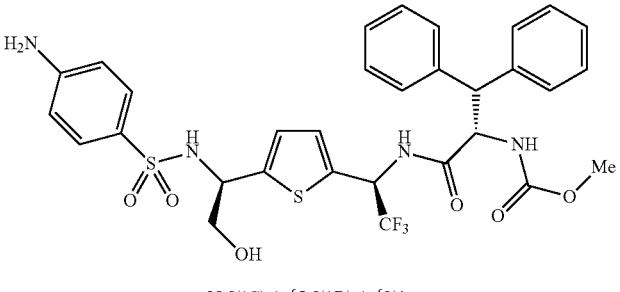<br>N-[(1S)-1-{5-[(1R)-1-{[(4-aminophenyl)sulfonyl]amino}-2-hydroxyethyl]thiophen-2-yl}-2,2,2-trifluoroethyl]-Nα-(methoxycarbonyl)-β-phenyl-L-phenylalaninamide | Example 44 using the appropriate alcohol in Step 9 | 700.0 (MNa+) |

-continued

| Example No. | Structure | Procedure | MS (m/z) |
|---|---|---|---|
| 88 | 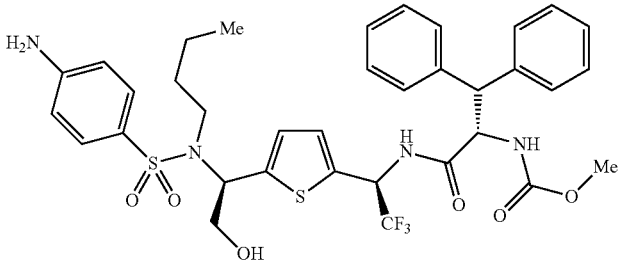 [SMILES: CCCCN([C@H](CO)c1ccc([C@@H](NC(=O)[C@@H](NC(=O)OC)C(c2ccccc2)c2ccccc2)C(F)(F)F)s1)S(=O)(=O)c1ccc(N)cc1]<br>N-[(1S)-1-{5-[(1R)-1-{[(4-aminophenyl)sulfonyl](butyl)amino}-2-hydroxyethyl]thiophen-2-yl}-2,2,2-trifluoroethyl]-Nα-(methoxycarbonyl)-β-phenyl-L-phenylalaninamide | Example 44 using the appropriate alcohol in Step 9 | 756.1 (MNa+) |
| 89 | 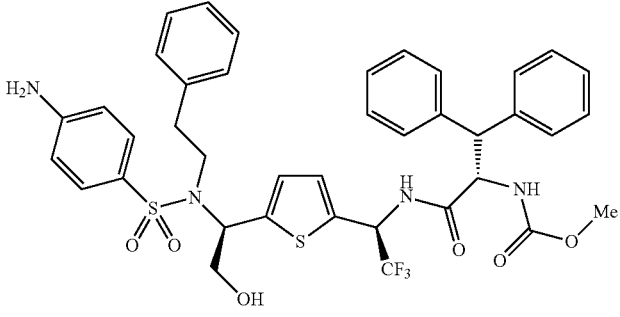 [SMILES: COC(=O)N[C@H](C(=O)N[C@H](c1ccc([C@@H](CO)N(CCc2ccccc2)S(=O)(=O)c2ccc(N)cc2)s1)C(F)(F)F)C(c1ccccc1)c1ccccc1]<br>N-[(1S)-1-{5-[(1R)-1-{[(4-aminophenyl)sulfonyl](2-phenylethyl)amino}-2-hydroxyethyl]thiophen-2-yl}-2,2,2-trifluoroethyl]-Nα-(methoxycarbonyl)-β-phenyl-L-phenylalaninamide | Example 44 using the appropriate alcohol in Step 9 | 803.0 (MNa+) |
| 90 | 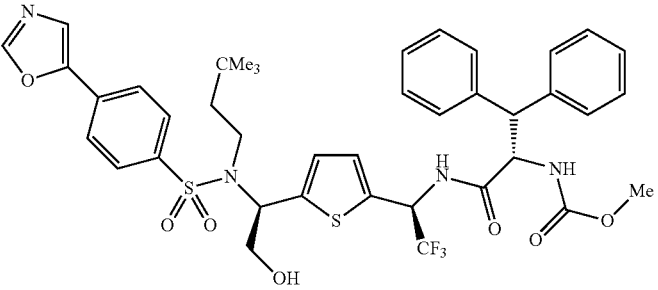<br>N-[(1S)-1-(5-{(1R)-1-[(3,3-dimethylbutyl){[4-(1,3-oxazol-5-yl)phenyl]sulfonyl}amino]-2-hydroxyethyl}thiophen-2-yl)-2,2,2-trifluoroethyl]-Nα-(methoxycarbonyl)43-phenyl-L-phenylalaninamide | Example 44 using the appropriate sulfonyl chloride in Step 8 | 835.2 (MNa+) |
| 91 | 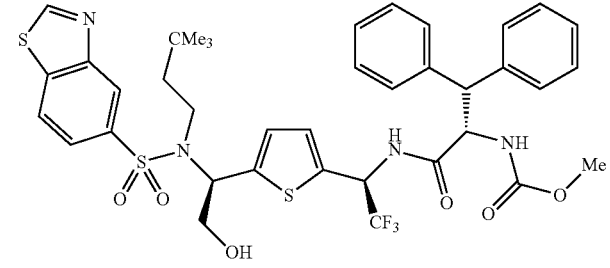<br>N-[(1S)-1-(5-{(1R)-1-[(1,3-benzothiazol-5-ylsulfonyl)(3,3-dimethylbutyl)amino]-2-hydroxyethyl}thiophen-2-yl)-2,2,2-trifluoroethyl]-Nα-(methoxycarbonyl)-β-phenyl-L-phenylalaninamide | Example 44 using the appropriate sulfonyl chloride in Step 8 | 825.1 (MNa+) |

| Example No. | Structure | Procedure | MS (m/z) |
|---|---|---|---|
| 92 | N-[(1S)-1-(5-{(1R)-1-[(3,3-dimethylbutyl)[4-(1-methyl-1H-pyrazol-3-yl)phenyl]sulfonyl}amino]-2-hydroxyethyl}thiophen-2-yl)-2,2,2-trifluoroethyl]-Nα-(methoxycarbonyl)-β-phenyl-L-phenylalaninamide | Example 44 using the appropriate sulfonyl chloride in Step 8 | 826.2 (MH+) |
| 93 | N-[(1S)-1-(5-{(1R)-1-[(3,3-dimethylbutyl)(1H-indazol-5-ylsulfonyl)amino]-2-hydroxyethyl}thiophen-2-yl)-2,2,2-trifluoroethyl]-Nα-(methoxycarbonyl)-β-phenyl-L-phenylalaninamide | Example 44 using the appropriate sulfonyl chloride in Step 8 | 808.2 (MNa+) |
| 94 | N-[(1S)-1-(5-{(1R)-1-[(3,3-dimethylbutyl)(1H-indol-6-ylsulfonyl)amino]-2-hydroxyethyl}thiophen-2-yl)-2,2,2-trifluoroethyl]-Nα-(methoxycarbonyl)-β-phenyl-L-phenylalaninamide | Example 44 using the appropriate sulfonyl chloride in Step 8 | 807.1 (MNa+) |
| 95 | N-[(1S)-1-(5-{(1R)-1-[(1-benzothiophen-2-ylsulfonyl)(3,3-dimethylbutyl)amino]-2-hydroxyethyl}thiophen-2-yl)-2,2,2-trifluoroethyl]-Nα-(methoxycarbonyl)-β-phenyl-L-phenylalaninamide | Example 44 using the appropriate sulfonyl chloride in Step 8 | 824.0 (MNA+) |

-continued

| Example No. | Structure | Procedure | MS (m/z) |
|---|---|---|---|
| 96 | N-[(1S)-1-(5-{(1R)-1-[(1,3-benzoxazol-5-ylsulfonyl)(3,3-dimethylbutyl)amino]-2-hydroxyethyl}thiophen-2-yl)-2,2,2-trifluoroethyl]-Nα-(methoxycarbonyl)-β-phenyl-L-phenylalaninamide | Example 44 using the appropriate sulfonyl chloride in Step 8 | 809.0 (MNa+) |
| 97 | N-[(1S)-1-{5-[(1R)-1-{[(4-amino-3-fluorophenyl)sulfonyl](3,3-dimethylbutyl)amino}-2-hydroxyethyl]thiophen-2-yl}-2,2,2-trifluoroethyl]-Nα-(methoxycarbonyl)-β-phenyl-L-phenylalaninamide | Example 44 using the appropriate sulfonyl chloride in Step 8 | 801.1 (MNa+) |
| 98 | N-[(1S)-1-{5-[(1R)-1-{[(4-amino-2-fluorophenyl)sulfonyl](3,3-dimethylbutyl)amino}-2-hydroxyethyl]thiophen-2-yl}-2,2,2-trifluoroethyl]-Nα-(methoxycarbonyl)-β-phenyl-L-phenylalaninamide | Example 44 using the appropriate sulfonyl chloride in Step 8 | 801.1 (MNa+) |
| 99 | N-[(1S)-1-(5-{(1R)-1-[(3,3-dimethylbutyl)(imidazo[1,2-a]pyrazin-6-ylsulfonyl)amino]-2-hydroxyethyl}thiophen-2-yl)-2,2,2-trifluoroethyl]-Nα-(methoxycarbonyl)-β-phenyl-L-phenylalaninamide | Example 44 using the appropriate sulfonyl chloride in Step 8 | 787.2 (MH+) |

| Example No. | Structure | Procedure | MS (m/z) |
|---|---|---|---|
| 100 | N-[(1S)-1-(5-{(1R)-1-[(1,3-benzothiazol-6-ylsulfonyl)(3,3-dimethylbutyl)amino]-2-hydroxyethyl}thiophen-2-yl)-2,2,2-trifluoroethyl]-Nα-(methoxycarbonyl)-β-phenyl-L-phenylalaninamide | Example 44 using the appropriate sulfonyl chloride in Step 8 | 825.1 (MNa+) |
| 101 | N-[(1S)-1-(5-{(1R)-1-[(1H-benzotriazol-6-ylsulfonyl)(3,3-dimethylbutyl)amino]-2-hydroxyethyl}thiophen-2-yl)-2,2,2-trifluoroethyl]-Nα-(methoxycarbonyl)-β-phenyl-L-phenylalaninamide | Example 44 using the appropriate sulfonyl chloride in Step 8 | 787.2 (MH+) |
| 102 | N-[(1S)-1-(5-{(1R)-1-[(3,3-dimethylbutyl)(1H-indazol-6-ylsulfonyl)amino]-2-hydroxyethyl}thiophen-2-yl)-2,2,2-trifluoroethyl]-Nα-(methoxycarbonyl)-β-phenyl-L-phenylalaninamide | Example 44 using the appropriate sulfonyl chloride in Step 8 | 786.1 (MH+) |
| 103 | N-[(1S)-1-(5-{(1R)-1-[(3,3-dimethylbutyl)(1H-indol-5-ylsulfonyl)amino]-2-hydroxyethyl}thiophen-2-yl)-2,2,2-trifluoroethyl]-Nα-(methoxycarbonyl)-β-phenyl-L-phenylalaninamide | Example 44 using the appropriate sulfonyl chloride in Step 8 | 807.1 (MNa+) |

| Example No. | Structure | Procedure | MS (m/z) |
|---|---|---|---|
| 104 | N-[(1S)-1-(5-{(1R)-1-[(1,3-benzothiazol-6-ylsulfonyl)(3,3,3-trifluoropropyl)amino]-2-hydroxyethyl}thiophen-2-yl)-2,2,2-trifluoroethyl]-Nα-(methoxycarbonyl)-β-phenyl-L-phenylalaninamide | Example 44 using the appropriate sulfonyl chloride in Step 8 and the appropriate alcohol in Step 9 | 815.0 (MH+) |
| 105 | N-[(1S)-1-(5-[(1R)-1-[(1,3-benzothiazol-6-ylsulfonyl)(4,4,4-trifluorobutyl)amino]-2-hydroxyethyl}thiophen-2-yl)-2,2,2-trifluoroethyl]-Nα-(methoxycarbonyl)-β-phenyl-L-phenylalaninamide | Example 44 using the appropriate sulfonyl chloride in Step 8 and the appropriate alcohol in Step 9 | 829.0 (MH+) |
| 106 | N-[(1S)-1-{5-[(1R)-1-{(1,3-benzothiazol-6-ylsulfonyl)[(2-$^2$H)propan-2-yl]amino}-2-hydroxyethyl]thiophen-2-yl}-2,2,2-trifluoroethyl]-Nα-(methoxycarbonyl)-β-phenyl-L-phenylalaninamide | Example 44 using the appropriate sulfonyl chloride in Step 8 and the appropriate alcohol in Step 9 | 768.1 (MH+) |
| 107 | Nα-(methoxycarbonyl)-β-phenyl-N-[(1S)-2,2,2-trifluoro-1-{5-[(1R)-2-hydroxy-1-1(1H-indazol-5-ylsulfonyl)[(2-$^2$H)propan-2-yl]amino}ethyl]thiophen-2-yl}ethyl-L-phenylalaninamide | Example 44 using the appropriate sulfonyl chloride in Step 8 and the appropriate alcohol in Step 9 | 773.0 (MNa+) |

| Example No. | Structure | Procedure | MS (m/z) |
|---|---|---|---|
| 108 | N-[(1S)-1-{5-[(1R)-1-{[(4-amino-2-fluorophenyl)sulfonyl][(2-²H)propan-2-yl]amino}-2-hydroxyethyl]thiophen-2-yl}-2,2,2-trifluoroethyl]-Nα-(methoxycarbonyl)-β-phenyl-L-phenylalaninamide | Example 44 using the appropriate sulfonyl chloride in Step 8 and the appropriate alcohol in Step 9 | 766.0 (MNa+) |
| 109 | methyl [(1S)-2-{[(1)-1-(5-{(1R)-1-[{[4-(aminocarbonyl)phenyl]sulfonyl}(isopropyl)amino]-2-hydroxyethyl}-2-thienyl)-2,2,2-trifluoroethyl]amino}-1-(diphenylmethyl)-2-oxoethyl]carbamate | Example 44 using the appropriate sulfonyl chloride in Step 8 and the appropriate alcohol in Step 9 | 747.10 (MH+) |
| 110 | N-((1S)-1-{5-[(1R)-1-((3,3-dimethylbutyl)1[4-(2H-tetrazol-2-yl)phenyl]sulfonyl}amino)-2-hydroxyethyl]-2-thienyl}-2,2,2-trifluoroethyl)-Nα-(methoxycarbonyl)-β-phenyl-L-phenylalaninamide | Example 44 using the appropriate sulfonyl chloride in Step 8 and the appropriate alcohol in Step 9 | 836.20 (MNa+) |
| 111 | N-((1S)-1-{5-[(1R)-1-((3,3-dimethylbutyl){[4-(1H-tetrazol-1-yl)phenyl]sulfonyl}amino)-2-hydroxyethyl]-2-thienyl}-2,2,2-trifluoroethyl)-Nα-(methoxycarbonyl)-β-phenyl-L-phenylalaninamide | Example 44 using the appropriate sulfonyl chloride in Step 8 | 836.20 (MNa+) |

-continued

| Example No. | Structure | Procedure | MS (m/z) |
|---|---|---|---|
| 112 | N-{2-[(3S)-3-1[(4-aminophenyl)sulfonyl](2H-triazol-2-yl)amino]-4-hydroxybutyl]phenyl}-Nα-(methoxycarbonyl)-β-phenyl-L-phenylalaninamide | Example 44 using the appropriate sulfonyl chloride in Step 8 | 835.15 (MNa+) |
| 113 | N-{2-[(3S)-3-{[(4-aminophenyl)sulfonyl][(1H-triazol-1-yl)methyl]amino}-4-hydroxybutyl]phenyl}-Nα-(methoxycarbonyl)-β-phenyl-L-phenylalaninamide | Example 44 using the appropriate sulfonyl chloride in Step 8 | 835.15 (MNa+) |
| 114 | N-{(1S)-1-[5-((1R)-1-{(3,3-dimethylbutyl)[(4-isoxazol-5-ylphenyl)sulfonyl]amino}-2-hydroxyethyl)-2-thienyl]-2,2,2-trifluoroethyl}-Nα-(methoxycarbonyl)-β-phenyl-L-phenylalaninamide | Example 44 using the appropriate sulfonyl chloride in Step 8 | 835.15 (MNa+) |
| 115 | N-{(1S)-1-[5-((1R)-1-{(3,3-dimethylbutyl)[4-(1-methyl-1H-pyrazol-4-yl)phenylsulfonyl]amino}-2-hydroxyethyl)-2-thienyl]-2,2,2-trifluoroethyl}-Nα-(methoxycarbonyl)-β-phenyl-L-phenylalaninamide | Example 44 using the appropriate sulfonyl chloride in Step 8 | 772.15 (MNa+) |

-continued

| Example No. | Structure | Procedure | MS (m/z) |
|---|---|---|---|
| 116 | N-[(1S)-1-(5-{(1R)-1-[[(4-amino-3-chlorophenyl)sulfonyl](3,3-dimethylbutyl)amino]-2-hydroxyethyl}-2-thienyl)-2,2,2-trifluoroethyl]-Nα-(methoxycarbonyl)-β-phenyl-L-phenylalaninamide | Example 44 using the appropriate sulfonyl chloride in Step 8 | 795.1 (MH+) |
| 117 | N-[(1S)-1-(5-{(1R)-1-[[(4-amino-2-chlorophenyl)sulfonyl](3,3-dimethylbutyl)amino]-2-hydroxyethyl}-2-thienyl)-2,2,2-trifluoroethyl]-Nα-(methoxycarbonyl)-β-phenyl-L-phenylalaninamide | Example 44 using the appropriate sulfonyl chloride in Step 8 | 795.1 (MH+) |
| 118 | N-[(1S)-1-(5-{(1R)-1-[(3,3-dimethylbutyl)([1,2,4]triazolo[1,5-a]pyridin-6-ylsulfonyl)amino]-2-hydroxyethyl}thiophen-2-yl)-2,2,2-trifluoroethyl]-Nalpha-(methoxycarbonyl)-beta-phenyl-L-phenylalaninamide | Example 44 using the appropriate sulfonyl chloride in Step 8 | 787.2 (MH+) |
| 119 | N-[(1S)-1-{5-[(1R)-1-{[(2-chloroimidazo[1,2-a]pyrazin-6-yl)sulfonyl](3,3-dimethylbutyl)amino}-2-hydroxyethyl]thiophen-2-yl}-2,2,2-trifluoroethyl]-Nα-(methoxycarbonyl)-β-phenyl-L-phenylalaninamide | Example 44 using the appropriate sulfonyl chloride in Step 8 | 821.0 (MH+) |

| Example No. | Structure | Procedure | MS (m/z) |
|---|---|---|---|
| 120 | N-[(1S)-1-(5-{(1R)-1-[(3,3-dimethylbutyl)([1,2,4]triazolo[1,5-a]pyridin-7-ylsulfonyl)amino]-2-hydroxyethyl}thiophen-2-yl)-2,2,2-trifluoroethyl]-Nalpha-(methoxycarbonyl)-beta-phenyl-L-phenylalaninamide onyl)-β-phenyl-L-phenylalaninamide | Example 44 using the appropriate sulfonyl chloride in Step 8 | 787.2 MH+) |
| 121 | N-[(1S)-1-(5-{(1R)-1-[(3,3-dimethylbutyl)([1,2,4]triazolo[1,5-a]pyrazin-6-ylsulfonyl)amino]-2-hydroxyethyl}thiophen-2-yl)-2,2,2-trifluoroethyl]-Nalpha-(methoxycarbonyl)-beta-phenyl-L-phenylalaninamide | Example 44 using the appropriate sulfonyl chloride in Step 8 | 810.1 (MH+) |

Example 122

N-[(1S)-1-(5-{(1R)-1-[(3,3-dimethylbutyl)(imidazo[1,2-a]pyrazin-6-ylsulfonyl)amino]-2-hydroxyethyl}thiophen-2-yl)-2,2,2-trifluoroethyl]-Nα-(methoxycarbonyl)-β-phenyl-L-phenylalaninamide (127)

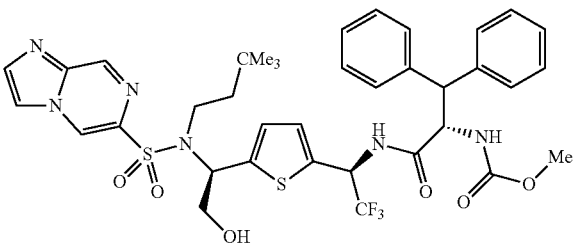

To a suspension of Pd/C (25 mg, 0.235 mmol) in methanol (3 mL) under $N_2$ was added N-[(1S)-1-{5-[(1R)-1-{[(2-chloroimidazo[1,2-a]pyrazin-6-yl)sulfonyl](3,3-dimethylbutyl)amino}-2-hydroxyethyl]thiophen-2-yl}-2,2,2-trifluoroethyl]-Nα-(methoxycarbonyl)-β-phenyl-L-phenylalaninamide (7.5 mg, 9.13 µmol). The resulting slurry was purged under vacuum and backfilled with $H_2$ three times, after which the mixture was stirred for 16 hours at room temperature. Since LCMS showed only 50% conversion, the reaction mixture was transferred to a pressure flask and hydrogenated at 50 psi of $H_2$ for 3 days, after which Pd/C (25 mg, 0.235 mmol) was added and the mixture was hydrogenated at 50 psi for 6 hours. The reaction mixture was filtered over a Celite pad, and the volatile components were evaporated under reduced pressure. The crude residue was purified by flash chromatography (Combiflash® Rf system; $SiO_2$ 4 grams Cat. No. 69-2203-304, solvent flow 18 mL/minute, elution gradient of 20-100% (EtOAc/hexanes). The fractions containing the desired product were pooled and evaporated under reduced pressure to afford the title material as a colorless oil. MS: m/z=787.2 ((MH+)).

Example 123

N-[(5-{(1R)-1-[(1,3-benzothiazol-6-ylsulfonyl)(2-methylpropyl)amino]-2-hydroxyethyl}thiophen-2-yl)methyl]-Nα-(methoxycarbonyl).-β-phenyl-L-phenylalaninamide

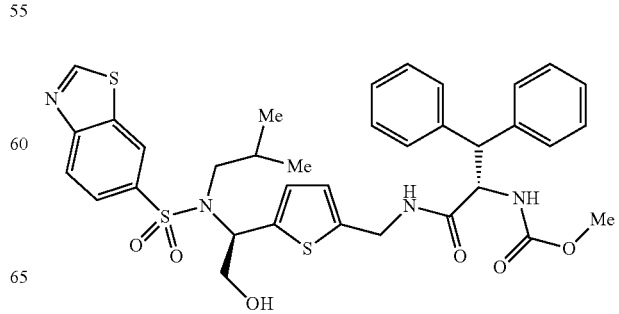

Step 1: N-[(1R)-1-(5-formylthiophen-2-yl)-2-hydroxyethyl]-1,3-benzothiazole-6-sulfonamide To a solution of (2R)-2-amino-2-[5-(5,5-dimethyl-1,3-dioxan-2-yl)thiophen-2-yl]ethanol hydrochloride (11.54 g, 39.3 mmol) in DCM (262 mL) at 0° C. was added slowly triethylamine (25 mL, 179 mmol). The mixture was stirred 15 minutes, after which TMSCl (5.52 mL, 43.2 mmol) was added. The mixture was stirred for 30 minutes at 0° C. and then 1,3-benzothiazole-6-sulfonyl chloride (9.64 g, 41.2 mmol) was added. The reaction mixture was allowed to reach room temperature overnight, and then 1N HCl (100 mL) and MeOH (50 mL) were added and the reaction mixture was stirred for 2 hours. The organic layer was separated and the aqueous layer was extracted 5 times with ethyl acetate (5×300 mL). The organic layers were combined and washed twice with a saturated solution of sodium bicarbonate (2×250 mL), then washed with brine (250 mL), dried over magnesium sulfate, filtered and concentrated under reduced pressure. The residue was swished with ether to obtain the pure desired product.

Step 2: N-[(1R)-2-{[tert-butyl(dimethyl)silyl]oxy}-1-(5-formylthiophen-2-yl)ethyl]-1,3-benzothiazole-6-sulfonamide To a solution of N-[(1R)-1-(5-formylthiophen-2-yl)-2-hydroxyethyl]-1,3-benzothiazole-6-sulfonamide (5.48 g, 14.9 mmol) and imidazole (1.27 g, 18.6 mmol) in DMF (75 mL) was added TBSCl (2.80 g, 18.6 mmol) and the reaction mixture was stirred overnight. The reaction was then quenched by the addition of water (400 mL) and ether (200 mL). The phases were separated and the aqueous layer was extracted with ether (3×250 mL). The combined organic layers were washed twice with brine solution (2×300 mL), dried over magnesium sulfate, filtered and concentrated under reduced pressure. The crude was purified on silica gel eluting with hexanes and ethyl acetate to afford the title compound.

Step 3: N-[(1R)-2-{[tert-butyl(dimethyl)silyl]oxy}-1-(5-{(Z)-[(tert-butylsulfinyl)imino]methyl}thiophen-2-yl)ethyl]-1,3-benzothiazole-6-sulfonamide To a solution of N-[(1R)-2-{[tert-butyl(dimethyl)silyl]oxy}-1-(5-formylthiophen-2-yl)ethyl]-1,3-benzothiazole-6-sulfonamide (5.0 g, 10.4 mmol) and 2-methylpropane-2-sulfinamide (1.51 g, 12.4 mmol) in THF (69 mL) was added titanium isopropoxide (6.52 mL, 31.1 mmol). The mixture was stirred at room temperature overnight.

Step 4: N-[(1R)-2-{[tert-butyl(dimethyl)silyl]oxy}-1-(5-{(Z)-[(tert-butylsulfinyl)imino]methyl}thiophen-2-yl)ethyl]-N-(2-methylpropyl)-1,3-benzothiazole-6-sulfonamide To a solution of N-[(1R)-2-{[tert-butyl(dimethyl)silyl]oxy}-1-(5-{(Z)-[(tert-butylsulfinyl)imino]methyl}thiophen-2-yl)ethyl]-1,3-benzothiazole-6-sulfonamide (2.1 g, 3.58 mmol) and isobutanol (0.66 mL, 7.17 mmol) in toluene (18 mL) was added (tributyl-$\lambda^5$-phosphanylidene)acetonitrile (1.74 mL, 7.17 mmol) and the reaction mixture was stirred at 100° C. for 2 hours. The mixture was cooled and then directly injected on a silica gel column eluting with hexanes and ethyl acetate.

Step 5: N-[(1R)-2-{[tert-butyl(dimethyl)silyl]oxy}-1-(5-{[(tert-butylsulfinyl)amino]methyl}thiophen-2-yl)ethyl]-N-(2-methylpropyl)-1,3-benzothiazole-6-sulfonamide To a solution of N-[(1R)-2-{[tert-butyl(dimethyl)silyl]oxy}-1-(5-{(Z)-[(tert-butylsulfinyl)imino]methyl}thiophen-2-yl)ethyl]-N-(2-methylpropyl)-1,3-benzothiazole-6-sulfonamide (1.78 g, 2.77 mmol) in MeOH (28 mL) at 0° C. was added NaBH$_4$ (0.11 g, 2.77 mmol) and the reaction mixture was stirred for 4 hours before being quenched by the addition of water (50 mL). The slurry was stirred for 20 minutes, then extracted with ethyl acetate (3×100 mL). The organic layers were combined and dried over magnesium sulfate, filtered and concentrated under reduced pressure. The crude was purified on silica gel eluting with hexanes and ethyl acetate.

Step 6: N-{(1R)-1-[5-(aminomethyl)thiophen-2-yl]-2-hydroxyethyl}-N-(2-methylpropyl)-1,3-benzothiazole-6-sulfonamide hydrochloride To a solution of N-[(1R)-2-{[tert-butyl(dimethyl)silyl]oxy}-1-(5-{[(tert-butylsulfinyl)amino]methyl}thiophen-2-yl)ethyl]-N-(2-methylpropyl)-1,3-benzothiazole-6-sulfonamide (1.12 g, 1.74 mmol) in MeOH (8.7 mL) was added 4 N HCl in dioxane (5.0 mL, 20 mmol) and the reaction mixture was stirred for 5 hours. The reaction was concentrated under reduced pressure and concentrated from heptanes. The product was use as such in the next step.

Step 7: N-[(5-{(1R)-1-[(1,3-benzothiazol-6-ylsulfonyl)(2-methylpropyl)amino]-2-hydroxyethyl}thiophen-2-yl)methyl]-Nα-(methoxycarbonyl)-β-phenyl-L-phenylalaninamide To a solution of N-{(1R)-1-[5-(aminomethyl)thiophen-2-yl]-2-hydroxyethyl}-N-(2-methylpropyl)-1,3-benzothiazole-6-sulfonamide hydrochloride (30 mg, 0.065 mmol), N-(methoxycarbonyl)-β-phenyl-L-phenylalanine (21 mg, 0.071 mmol) and DIPEA (45 µL, 0.26 mmol) in DMF (300 µL) at 0° C. was added BOP (32 mg, 0.071 mmol). The reaction mixture was stirred at 0° C. for 4 hours before being quenched with a saturated solution of sodium bicarbonate (3 mL). The quenched mixture was extracted with ether/ethyl acetate (1/1 3×3 mL). The organic layers were combined and washed with brine, dried over magnesium sulfate, filtered and concentrated under reduced pressure. The crude was purified on silica gel eluting with hexanes and ethyl acetate. MS: m/z=729.1 (MNa+).

Examples 124 to 134

The compounds shown in the table below were prepared using the procedure described in Example 123.

| Example No. | Structure & Name | Procedure | MS (m/z) |
|---|---|---|---|
| 124 | N-[1-[[5-[1-(1,3-benzothiazol-6-ylsulfonyl(isobutyl)amino)-2-hydroxy-ethyl]-2-thienyl]methylcarbamoyl]-2-(3-fluoro-4-pyridyl)-2-phenyl-ethyl]benzamide | Example 123 using the appropriate amino acid in Step 7 | 772.2 (MH+) |
| 125 | N-[1-[[5-[1-(1,3-benzothiazol-6-ylsulfonyl(isobutyl)amino)-2-hydroxy-ethyl]-2-thienyl]methylcarbamoyl]-2-phenyl-2-(4-quinolyl)ethyl]benzamide | Example 123 using the appropriate amino acid in Step 7 | 804.2 (MH+) |
| 126 | N-[1[[5-[1-(1,3-benzothiazol-6-ylsulfonyl(isobutyl)amino)-2-hydroxy-ethyl]-2-thienyl]methylcarbamoyl]-2-phenyl-2-(1H-pyrrolo[2,3-b]pyridin-3-yl)ethyl]benzamide | Example 123 using the appropriate amino acid in Step 7 | 793.2 (MH+) |

| Example No. | Structure & Name | Procedure | MS (m/z) |
|---|---|---|---|
| 127 | 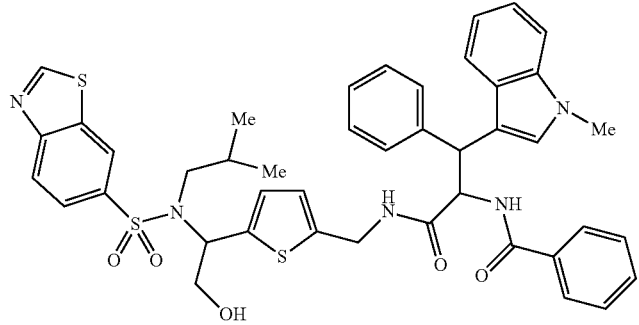 [SMILES: CC(C)CN(C(CO)c1ccc(CNC(=O)C(NC(=O)c2ccccc2)C(c2ccccc2)c2cn(C)c3ccccc23)s1)S(=O)(=O)c1ccc2ncsc2c1]<br>N-[1-[[5-[1-(1,3-benzothiazol-6-ylsulfonyl(isobutyl)amino)-2-hydroxy-ethyl]-2-thienyl]methylcarbamoyl]-2-(1-methylindol-3-yl)-2-phenyl-ethyl]benzamide | Example 123 using the appropriate amino acid in Step 7 | 807.0 (MH+) |
| 128 | 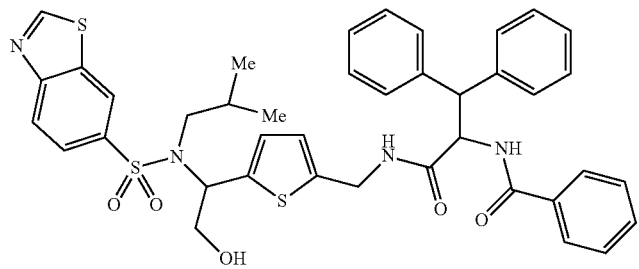 [SMILES: CC(C)CN(C(CO)c1ccc(CNC(=O)C(NC(=O)c2ccccc2)C(c2ccccc2)c2ccccc2)s1)S(=O)(=O)c1ccc2ncsc2c1]<br>N-[1-benzhydryl-2-[[5-[1-(1,3-benzothiazol-6-ylsulfonyl(isobutyl)amino)-2-hydroxy-ethyl]-2-thienyl]methylamino]-2-oxo-ethyl]benzamide | Example 123 using the appropriate amino acid in Step 7 | 753.2 (MH+) |
| 129 | 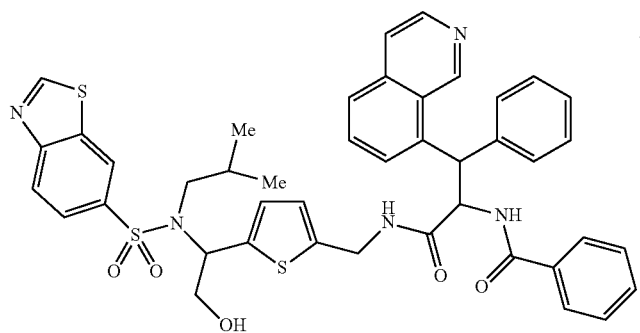 [SMILES: CC(C)CN(C(CO)c1ccc(CNC(=O)C(NC(=O)c2ccccc2)C(c2ccccc2)c2cccc3ccncc23)s1)S(=O)(=O)c1ccc2ncsc2c1]<br>N-[1-[[5-[1-(1,3-benzothiazol-6-ylsulfonyl(isobutyl)amino)-2-hydroxy-ethyl]-2-thienyl]methylcarbamoyl]-2-(8-isoquinolyl)-2-phenyl-ethyl]benzamide | Example 123 using the appropriate amino acid in Step 7 | 804.2 (MH+) |

| Example No. | Structure & Name | Procedure | MS (m/z) |
|---|---|---|---|
| 130 | 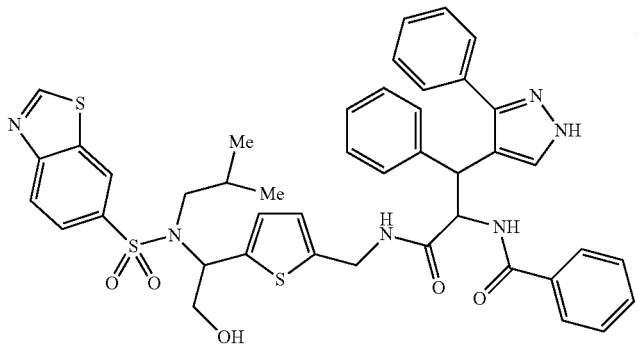 [SMILES: CC(C)CN(C(CO)c1ccc(CNC(=O)C(NC(=O)c2ccccc2)C(c2ccccc2)c2c[nH]nc2-c2ccccc2)s1)S(=O)(=O)c1ccc2ncsc2c1]<br><br>N-[1-[[5-[1-(1,3-benzothiazol-6-ylsulfonyl(isobutyl)amino)-2-hydroxy-ethyl]-2-thienyl]methylcarbamoyl]-2-phenyl-2-(3-phenyl-1H-pyrazol-4-yl)ethyl]benzamide | Example 123 using the appropriate amino acid in Step 7 | 819.2 (MH+) |
| 131 | 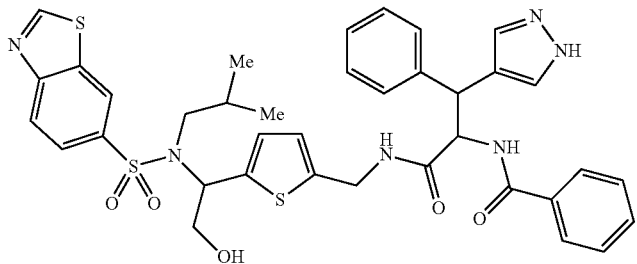 [SMILES: CC(C)CN(C(CO)c1ccc(CNC(=O)C(NC(=O)c2ccccc2)C(c2ccccc2)c2cn[nH]c2)s1)S(=O)(=O)c1ccc2ncsc2c1]<br><br>N-[1-[[5-[1-(1,3-benzothiazol-6-ylsulfonyl(isobutyl)amino)-2-hydroxy-ethyl]-2-thienyl]methylcarbamoyl]-2-phenyl-2-(1H-pyrazol-4-yl)ethyl]benzamide | Example 123 using the appropriate amino acid in Step 7 | 743.2 (MH+) |
| 132 | 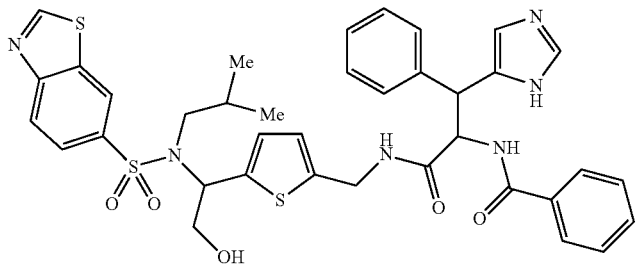 [SMILES: CC(C)CN(C(CO)c1ccc(CNC(=O)C(NC(=O)c2ccccc2)C(c2ccccc2)c2cnc[nH]2)s1)S(=O)(=O)c1ccc2ncsc2c1]<br><br>N-[1-[[5-[1-(1,3-benzothiazol-6-ylsulfonyl(isobutyl)amino)-2-hydroxy-ethyl]-2-thienyl]methylcarbamoyl]-2-(1H-imidazol-5-yl)-2-phenyl-ethyl]benzamide | Example 123 using the appropriate amino acid in Step 7 | 743.2 (MH+) |

| Example No. | Structure & Name | Procedure | MS (m/z) |
|---|---|---|---|
| 133 | 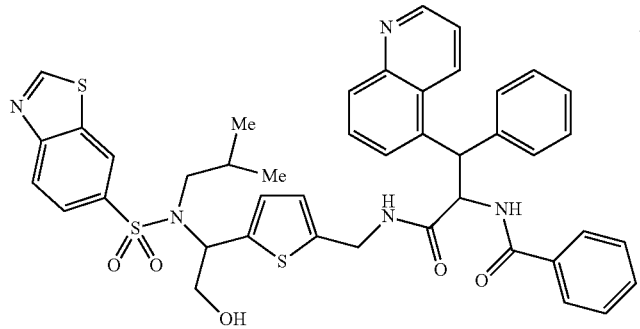 [SMILES: CC(C)CN(C(CO)c1ccc(CNC(=O)C(NC(=O)c2ccccc2)C(c2ccccc2)c2cccc3ncccc23)s1)S(=O)(=O)c1ccc2ncsc2c1]<br>N-[1-[[5-[1-(1,3-benzothiazol-6-ylsulfonyl(isobutyl)amino)-2-hydroxy-ethyl]-2-thienyl]methylcarbamoyl]-2-phenyl-2-(5-quinolyl)ethyl]benzamide | Example 123 using the appropriate amino acid in Step 7 | 804.1 (MH+) |
| 134 | 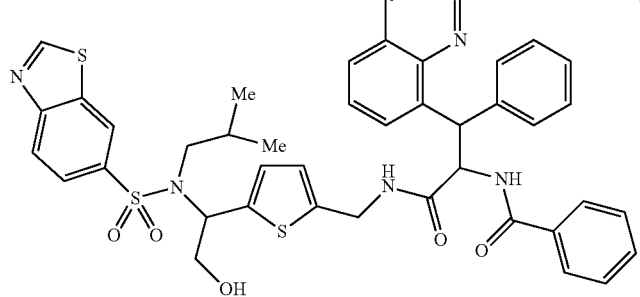<br>N-[1-[[5-[1-(1,3-benzothiazol-6-ylsulfonyl(isobutyl)amino)-2-hydroxy-ethyl]-2-thienyl]methylcarbamoyl]-2-phenyl-2-(7-quinolyl)ethyl]benzamide | Example 123 using the appropriate amino acid in Step 7 | 804.1 (MH+) |

Assay Example 1

Assay for Inhibition of Microbial Expressed HIV Protease

The inhibition of WT HIV-1 protease was studied using the reaction of the protease (expressed in *Eschericia coli*) with a peptide substrate [Val-Ser-Gln-Asn-(betanaphthyl)Ala-Pro-Ile-Val (SEQ ID NO:1)]. Compounds were tested using Procedure A. In Procedure A, the test compound was first preincubated with the enzyme in assay buffer (50 mM sodium acetate, pH 5.5, 100 mM NaCl, and 0.1% BSA) for 30 minutes at room temperature. Substrate was then added to 400 micromolar in a total volume of 80 microliters containing 10 picomolar HIV-1 protease and the reaction was incubated for 1 hour at 30° C. The reaction was quenched with the addition of 120 microliters of 10% phosphoric acid. The product formation was determined after separation of product and substrate on a Zorbax Eclipse XDB-C18 column (Agilent Technologies, Santa Clara, Calif.) connected to an Agilent 1100 high performance liquid chromatography system with fluorescence detection (excitation 270 nanometer and emission 330 nanometer).

Representative compounds of the present invention have exhibited inhibition of HIV-1 protease in this assay. For example, the compounds of Examples 1 to 134 were tested in the assay and exhibited the $IC_{50}$ values shown in Table B below.

Assay Example 2

Cytotoxicity

Cytotoxicity was determined by microscopic examination of the cells, wherein a trained analyst observed each culture for any of the following morphological changes as compared to the control cultures: pH imbalance, cell abnormality, cytostatic, cytopathic, or crystallization (i.e., the compound is not soluble or forms crystals in the well). All of the exemplified compounds were tested in this assay and none was found to exhibit cytotoxicity.

TABLE B

| Example No. | Enzyme inhibition $IC_{50}$ (nM) |
|---|---|
| 1 | 72.8 |
| 2 | 250 |
| 3 | 12.1 |
| 4 | 8.81 |

TABLE B-continued

| Example No. | Enzyme inhibition $IC_{50}$ (nM) |
|---|---|
| 5 | 0.54 |
| 6 | 42.7 |
| 7 | 3.5 |
| 8 | 0.31 |
| 9 | 0.63 |
| 10 | 2.6 |
| 11 | 1.61 |
| 12 | 18.8 |
| 13 | 3.9 |
| 14 | 4.1 |
| 15 | 6.6 |
| 16 | 0.44 |
| 17 | 2.4 |
| 18 | 6.95 |
| 19 | 33.8 |
| 20 | 6.97 |
| 21 | 62.4 |
| 22 | 6.1 |
| 23 | 60.9 |
| 24 | 13.6 |
| 25 | 7.99 |
| 26 | 31.0 |
| 27 | 15.5 |
| 28 | 1.45 |
| 29 | 106 |
| 30 | 5.13 |
| 31 | 3.62 |
| 32 | 2.27 |
| 33 | 96.6 |
| 34 | 35.0 |
| 35 | 11.9 |
| 36 | 3.65 |
| 37 | 5.65 |
| 38 | 13.6 |
| 39 | 26.9 |
| 40 | 175 |
| 41 | 8.83 |
| 42 | 110 |
| 43 | 5.04 |
| 44 | 0.196 |
| 45 | 0.308 |
| 46 | 0.09 |
| 47 | 33.7 |
| 48 | 184.3 |
| 49 | 3.96 |
| 50 | 121 |
| 51 | 17.5 |
| 52 | 2.0 |
| 53 | 0.156 |
| 54 | 21.7 |
| 55 | 45.8 |
| 56 | 59.4 |
| 57 | 1.32 |
| 58 | 2.71 |
| 59 | 4.22 |
| 60 | 2.01 |
| 61 | 23.0 |
| 62 | 18.5 |
| 63 | 3.98 |
| 64 | 6.48 |
| 65 | 0.18 |
| 66 | 8.97 |
| 67 | 11.9 |
| 68 | 27.5 |
| 69 | 9.42 |
| 70 | 3.16 |
| 71 | 6.64 |
| 72 | 43.8 |
| 73 | 2.03 |
| 74 | 0.45 |
| 75 | 7.89 |
| 76 | 11.8 |
| 77 | 23.0 |
| 78 | 66.1 |
| 79 | 12.5 |
| 80 | 30.5 |
| 81 | 74.1 |
| 82 | 92.5 |
| 83 | 0.30 |
| 84 | 0.75 |
| 85 | 0.33 |
| 86 | 0.34 |
| 87 | 194 |
| 88 | 0.33 |
| 89 | 2.6 |
| 90 | 25.9 |
| 91 | 2.9 |
| 92 | 66.6 |
| 93 | 0.31 |
| 94 | 0.09 |
| 95 | 6.95 |
| 96 | 1.95 |
| 97 | 1.23 |
| 98 | 0.44 |
| 99 | 3.39 |
| 100 | 0.90 |
| 101 | 0.84 |
| 102 | 0.63 |
| 103 | 6.14 |
| 104 | 0.85 |
| 105 | 1.77 |
| 106 | 34.7 |
| 107 | 23.4 |
| 108 | 9.4 |
| 109 | 31.5 |
| 110 | 10.5 |
| 111 | 19.3 |
| 112 | 73.5 |
| 113 | 25.9 |
| 114 | 0.77 |
| 115 | 20.9 |
| 116 | 3.54 |
| 117 | 0.47 |
| 118 | 2.43 |
| 119 | 13.9 |
| 120 | 3.00 |
| 121 | 3.59 |
| 122 | 5.78 |
| 123 | 6.30 |
| 124 | 568 |
| 125 | 409 |
| 126 | 4.0 |
| 127 | 8.0 |
| 128 | 53.0 |
| 129 | 7.0 |
| 130 | 952 |
| 131 | 79.0 |
| 132 | 216 |
| 133 | 4.76 |
| 134 | 15.2 |

1. The assay was conducted in 10% fetal bovine serum.
2. N.D. = not determined

While the foregoing specification teaches the principles of the present invention, with examples provided for the purpose of illustration, the practice of the invention encompasses all of the usual variations, adaptations and/or modifications that come within the scope of the following claims.

What is claimed is:

1. A compound of Formula I:

(I)

or a pharmaceutically acceptable salt thereof, wherein:
  $R^1$ is H, $C_{1-6}$ alkyl, $C_{1-6}$ fluoroalkyl, CycA, AryA, HetA, $C_{1-6}$ alkyl substituted with CycA, $C_{1-6}$ alkyl substituted with AryA, or $C_{1-6}$ alkyl substituted with HetA;
  $R^2$ is $C_{1-6}$ alkyl-OH;
  Ring A is:

wherein the asterisks (*) denote the points of attachment to the rest of the compound;
  $R^{3A}$ is H, $C_{1-6}$ alkyl, $C_{1-6}$ haloalkyl, or CycB;
  $R^{3B}$ is H or $C_{1-6}$ alkyl;
  $R^{4A}$ is:

-continued wherein the asterisk (*) denotes the point of attachment to the rest of the compound;
  $R^{4B}$ is H or $C_{1-6}$ alkyl;
  each $X^B$ and each $X^C$ are independently halo;
  m is an integer equal to 0 or 1;
  n is an integer equal to 0 or 1;
  $R^5$ is C(O)—$R^K$;
  $R^K$ is O—$C_{1-6}$ alkyl or AryC;
  $R^6$ is H or $C_{1-6}$ alkyl;
  $R^7$ is AryQ, HetQ, or HetQ;
  AryQ is an aryl which is independently phenyl, naphthyl, tetrahydronaphthyl, indenyl, or dihydroindenyl, wherein the aryl is optionally substituted with from 1 to 3 $X^A$ each of which is independently:
    (1) $C_{1-6}$ haloalkyl,
    (2) OH
    (3) halo,
    (4) $NH_2$,
    (5) N(H)C(O)O—$C_{1-6}$ alkyl,
    (6) C(O)—$C_{1-6}$ alkyl,
    (7) C(O)$NH_2$,
    (8) $C_{1-6}$ alkyl substituted with:
      (a) OH,
      (b) $NH_2$, or
      (c) CH(O),
    (9) $C_{1-6}$ haloalkyl substituted with OH,
    (10) HetD
    (11) C(O)-HetD, or
    (12) $C_{1-6}$ alkyl substituted with HetD;
    with the proviso that no more than 2 $X^A$ are HetD, C(O)-HetD or $C_{1-6}$ alkyl substituted with HetD;
  HetQ is a heteroaryl which is independently (i) a 5- or 6-membered heteroaromatic ring containing from 1 to 4 heteroatoms independently selected from N, O and S, wherein each N is optionally in the form of an oxide or (ii) a 9- or 10-membered bicyclic, fused ring system containing from 1 to 3 heteroatoms independently selected from N, O and S, and wherein at least one of the rings is aromatic, each N in a ring is optionally in the form of an oxide, and each S is optionally S(O) or S(O)₂; and wherein the heteroaryl is optionally substituted with from 1 to 3 substituents selected from halo, NH₂ and O—C₁₋₆ alkyl;

HetQ' is independently a dihydro derivative of the heteroaryl defined in HetQ wherein the dihydro derivative is not or does not contain an aromatic ring; and wherein the derivative is optionally substituted with from 1 to 3 oxo substituents;

CycA is a C₃₋₇ cycloalkyl which is optionally substituted with from 1 to 3 halo substituents;

CycB is a C₃₋₇ cycloalkyl which is optionally substituted with from 1 to 3 substituents each of which is independently halo or C₁₋₆ alkyl;

AryA is an aryl which is independently phenyl or naphthyl, wherein the phenyl or naphthyl is optionally substituted with from 1 to 3 halo substituents;

AryC is an aryl which is independently phenyl or naphthyl, wherein the phenyl or naphthyl is optionally substituted with from 1 to 3 halo substituents;

HetA is a heteroaryl which is independently (i) a 5- or 6-membered heteroaromatic ring containing from 1 to 3 heteroatoms independently selected from N, O and S, or (ii) is a fused, 9- or 10-membered heterobicyclic ring containing from 1 to 3 heteroatoms independently selected from N, O and S, and wherein at least one of the rings is aromatic, each N in a ring is optionally in the form of an oxide, and each S is optionally S(O) or S(O)₂; wherein the heteroaromatic ring (i) or the heterobicyclic ring (ii) is optionally substituted with from 1 to 3 Y^C wherein each Y^C independently
(1) C₁₋₆ alkyl,
(2) O—C₁₋₆ alkyl, or
(3) SO₂—N(C₁₋₆ alkyl)₂;

HetC is a heteroaryl which is independently (i) a 5- or 6-membered heteroaromatic ring containing from 1 to 3 heteroatoms independently selected from N, O and S, or (ii) is a fused, 9- or 10-membered heterobicyclic ring containing from 1 to 3 heteroatoms independently selected from N, O and S, and wherein at least one of the rings is aromatic, each N in a ring is optionally in the form of an oxide, and each S is optionally S(O) or S(O)₂; wherein the heteroaromatic ring (i) or the heterobicyclic ring (ii) is optionally substituted with from 1 to 3 Y^D wherein each Y^D independently is C₁₋₆alkyl or phenyl; and each HetD is independently a 5- or 6-membered heteroaromatic ring containing from 1 to 4 heteroatoms independently selected from N, O and S, wherein the heteroaromatic ring is optionally substituted with from 1 to 3 substituents each of which is independently C₁₋₆ alkyl.

2. A compound according to claim 1, or a pharmaceutically acceptable salt thereof, wherein Ring A is

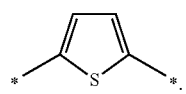

3. A compound according to claim 1, or a pharmaceutically acceptable salt thereof, wherein R¹ is H, C₁₋₆ alkyl, C₁₋₆ fluoroalkyl, (CH₂)₁₋₂CycA, (CH₂)₁₋₂-HetA, or (CH₂)₁₋₂AryA.

4. A compound according to claim 3, or a pharmaceutically acceptable salt thereof, wherein:

CycA is cyclopropyl or cyclobutyl, wherein the cycloalkyl is optionally substituted with 1 or 2 fluoro substituents;

HetA is a heteroaryl which is pyrazolyl, oxadiazolyl, pyridinyl, indolyl, or pyrrolopyridinyl; wherein the heteroaryl is optionally substituted with 1 substituent which is C₁₋₆ alkyl, O—C₁₋₆ alkyl, or SO₂—N(C₁₋₆ alkyl)₂; and AryA is phenyl.

5. A compound according to claim 3, or a pharmaceutically acceptable salt thereof, wherein R¹ is:

(1) H, (2) CH₂CH₃, (3) CH(CH₃)₂, (4) CH(CD₃)₂, (5) CD(CD₃)₂, (6) CH₂CH₂CH₂CH₃, (7) CH₂CH(CH₃)₂, (8) CH₂CH₂CH(CH₃)₂, (9) CH₂CH₂C(CH₃)₃,

(10) CH₂CH₂CF₃,

(11) CH₂CH₂CH₂CF₃, (12)

*—CH₂—cyclopropyl, (13)

*—CH₂—cyclobutyl(F)(F), (14)

*—CH₂CH₂—phenyl, (15)

*—CH₂—pyrazolyl-NH, optionally substituted with 1 substituent which is SO₂N(CH₃)₂, (16)

*—CH₂—pyrazolyl-NH, (17)

*—CH₂—isoxazolyl, optionally mono-substituted with CH₃,

-continued

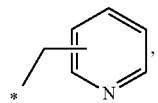
(18)

optionally substituted with 1 substituent which is OCH₃,

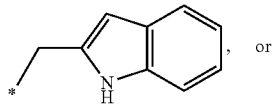
(19)

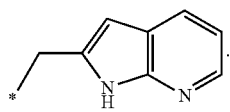
(20)

6. A compound according to claim 1, or a pharmaceutically acceptable salt thereof, wherein $R^2$ is $CH_2OH$.

7. A compound according to any one of claims 1 to 6, or a pharmaceutically acceptable salt thereof, wherein $R^{3A}$ is H, $CH_3$, $CH_2CH_3$, $CF_3$, or cyclopropyl; and $R^{3B}$ is H or $CH_3$.

8. A compound according to claim 7, or a pharmaceutically acceptable salt thereof, wherein $R^{3A}$ is H, $CH_3$, or $CF_3$; and $R^{3B}$ is H.

9. A compound according to any one of claims 1 to 8, or a pharmaceutically acceptable salt thereof, wherein:
$R^{4A}$ is:

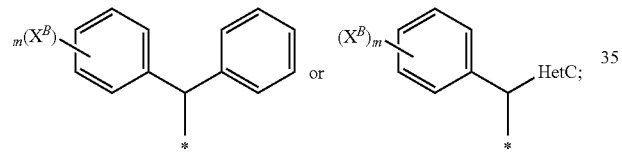

and
$R^{4B}$ is H.

10. A compound according to claim 9, or a pharmaceutically acceptable salt thereof, wherein:
HetC is a heteroaryl which is independently (i) a 5- or 6-membered heteroaromatic ring containing from 1 to 3 N atoms or (ii) a fused, 9- or 10-membered heterobicyclic ring containing from 1 to 3 N atoms, and wherein at least one of the rings is aromatic and each N is optionally in the form of an oxide; wherein the heteroaryl is optionally substituted with from 1 to 3 $Y^D$ wherein each $Y^D$ is independently $C_{1-3}$ alkyl or phenyl; and
$X^B$ is fluoro.

11. The compound according to claim 10, or a pharmaceutically acceptable salt thereof, wherein:
HetC is a heteroaryl which is:

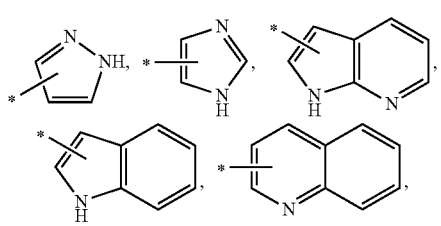

-continued

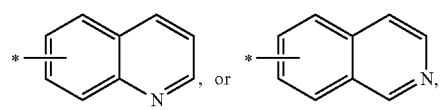

wherein the heteroaryl is optionally substituted with from 1 to 3 $Y^D$ wherein each $Y^D$ is independently $CH_3$ or phenyl.

12. The compound according to claim 9, or a pharmaceutically acceptable salt thereof, wherein:
$R^{4A}$ is:

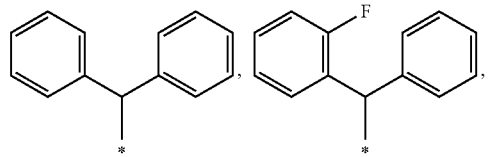

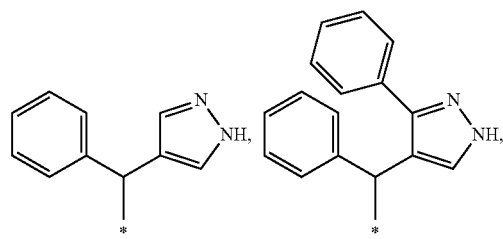

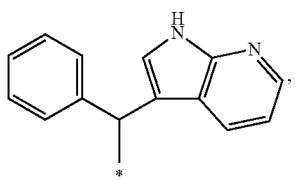

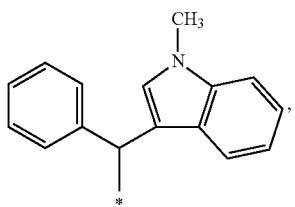

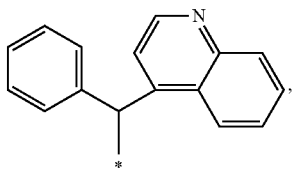

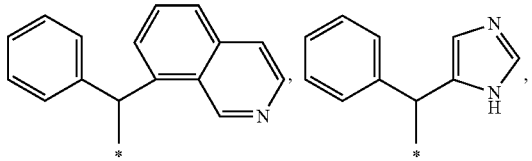

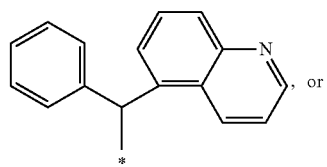

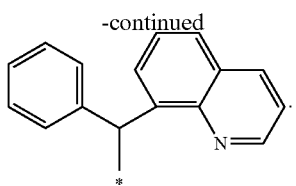

13. The compound according to claim 1, or a pharmaceutically acceptable salt thereof, wherein $R^5$ is $C(O)OCH_3$ or C(O)-phenyl.

14. The compound according to claim 1, or a pharmaceutically acceptable salt thereof, wherein:

AryQ in $R^7$ is phenyl or dihydroindenyl, either of which is optionally substituted with from 1 to 3 $X^A$, each of which is independently:
(1) OH,
(2) Cl,
(3) F,
(4) $NH_2$,
(5) $N(H)C(O)O$—$C_{1-4}$ alkyl,
(6) C(O)—$C_{1-4}$ alkyl,
(7) $C_{1-4}$ alkyl substituted with
  (a) OH,
  (b) $NH_2$,
(8) $C_{1-4}$ fluoroalkyl substituted with OH,
(9) HetD
(10) C(O)-HetD, or
(11) $CH_2$-HetD;
with the proviso that no more than 2 $X^A$ are HetD, C(O)-HetD or $CH_2$—HetD; and wherein HetD is a heteroaromatic ring which is oxazolyl, isoxazolyl, pyrazolyl, triazolyl, tetrazolyl, or pyridinyl, wherein the heteroaromatic ring is optionally substituted with from 1 to 3 substituents which is $C_{1-4}$ alkyl;

HetQ in $R^7$ is a heteroaryl which is thiophenyl (also referred to as thienyl), imidazolyl, pyridinyl, imidazopyridinyl, imidazopyrazinyl, triazolopyridinyl, triazolopyrazinyl, benzoimidazolyl, benzothiophenyl (also referred to as benzothienyl), benzothiadiazolyl, benzotriazolyl, quinolinyl, benzoxazolyl, benzothiazolyl, indolyl, and indazolyl; wherein the heteroaryl is optionally substituted with from 1 to 3 substituents selected from Cl, $NH_2$ and $OCH_3$; and HetQ' in $R^7$ is a non-aromatic dihydroindolyl, dihydropyridinyl, or dihydroisochromenyl, which is optionally substituted with from 1 to 3 $X^A$ substituents which are Cl or oxo.

15. The compound according to claim 1, or a pharmaceutically acceptable salt thereof, wherein $R^7$ is phenyl which is optionally substituted with a total of from 1 to 3 substituents, wherein:

(a) from zero to three substituents which are independently:
  (1) $CF_3$,
  (2) Cl,
  (3) F,
  (4) $NH_2$,
  (5) $N(H)C(O)OCH_3$,
  (6) $C(O)CH_3$,
  (7) $C(O)NH_2$,
  (8) $CH_2OH$,
  (9) $CH(OH)CH_3$,
  (10) $CH_2C(CH_3)_2OH$, or
  (11) $CH(CF_3)OH$, (b) from zero to one substituent which is independently:
  (1) $CH_2$-pyridinyl,
  (2) C(O)-pyridinyl, or
  (3) a heteroaromatic ring selected from the group consisting of oxazolyl, pyrazolyl optionally substituted with $CH_3$, tetrazolyl, triazolyl, and isoxazolyl.

16. The compound according to claim 14, or a pharmaceutically acceptable salt thereof, wherein $R^7$ is:
(1) phenyl,
(2) 4-aminophenyl,
(3) 4-amino-3-fluorophenyl,
(4) 4-amino-2-fluorophenyl,
(5) 4-amino-2-chlorophenyl,
(6) 4-amino-3-chlorophenyl,
(7) 4-aminocarbonylphenyl,
(8) 4-hydroxymethylphenyl,
(9) 4-hydroxymethyl-3-trifluoromethylphenyl,
(10) 3,5-difluoro-4-hydroxymethylphenyl,
(11) 4-(2-hydroxy-2-methylpropyl)phenyl,
(12) 4-(1-hydroxyethyl)phenyl,
(13) 4-(2,2,2-trifluoro-1-hydroxyethyl)phenyl,
(14) 4-acetylphenyl,
(15) 4-[(methoxycarbonyl)amino]phenyl,
(16) 3-(pyridin-2-ylcarbonyl)phenyl,
(17) 3-(pyridin-2-ylmethyl)phenyl,
(18) 4-(1,3-oxazol-5-yl)phenyl,
(19) 4-(1H-pyrazol-3-yl optionally substituted with $CH_3$) phenyl,
(20) 4-(2H-tetrazol-2-yl)phenyl,
(21) 4-(1H-tetrazol-1-yl)phenyl,
(22) 4-(2H-triazol-2-yl)phenyl,
(23) 4-(1H-triazol-1-yl)phenyl,
(24) 4-(isoxazol-5-yl)phenyl,
(25) 4-(1H-pyrazol-4-yl optionally substituted with $CH_3$) phenyl,
(26) 1-hydroxy-2,3-dihydro-1H-inden-5-yl, or
(27) 3-hydroxy-2,3-dihydro-1H-inden-5-yl.

17. The compound according to claim 16, or a pharmaceutically acceptable salt thereof, wherein $R^7$ is 4-aminophenyl.

18. The compound according to claim 14, or a pharmaceutically acceptable salt thereof, wherein $R^7$ is (i) a heteroaryl which is thiophenyl, pyridinyl, indolyl, benzothiazolyl, indazolyl, benzothiadiazolyl, benzimidazolyl, benzothiophenyl, benzooxazolyl, benzotriazolyl, imidazopyridinyl, imidazopyrazinyl, triazolopyridinyl, triazolopyrazinyl, or quinolinyl; wherein the heteroaryl is optionally substituted with from 1 to 3 substituents each of which is independently:
(1) $OCH_3$,
(2) Cl, or
(3) $NH_2$;
or is (ii) a non-aromatic dihydroindolyl, dihydroisoquinolinyl, dihydroisochromenyl, or dihydropyridinyl which is optionally substituted with from 1 to 3 substituents each of which is independently oxo and Cl.

19. The compound according to claim 18, or a pharmaceutically acceptable salt thereof, wherein $R^7$ is:
(1) 1H-benzimidazol-6-yl,
(2) 1,3-benzooxazol-5-yl,
(3) 1,3-benzothiazol-5-yl,
(4) 1,3-benzothiazol-6-yl,
(5) 1,2,3-benzothiadiazol-6-yl,
(6) 1-benzothiophen-2-yl,
(7) 1H-benzotriazol-6-yl,
(8) 1H-indol-2-yl,
(9) 1H-indol-4-yl,
(10) 1H-indol-5-yl,
(11) 1H-indol-6-yl,
(12) 1H-indazol-5-yl,

(13) 1H-indazol-6-yl,
(14) imidazo[1,2-]pyrazin-6-yl
(15) 2-chloroimidazo[1,2-]pyrazin-6-yl
(16) imidazo[1,2-]pyridin-6-yl,
(17) imidazo[1,2-]pyridin-7-yl,
(18) 4-aminopyridin-2-yl,
(19) 6-methoxypyridin-3-yl,
(20) quinolin-6-yl,
(21) 4-aminothiophen-2-yl,
(22) 5-aminothiophen-2-yl,
(23) 5-chlorothiophen-2-yl,
(24) [1,2,4]triazolo[1,5-]pyrazin-6-yl,
(25) [1,2,4]triazolo[1,5-]pyridin-6-yl,
(26) [1,2,4]triazolo[1,5-]pyridin-7-yl,
(27) 3-chloro-3a,7a-dihydro-1H-indol-6-yl,
(28) 3,4-dihydro-1H-isochromen-6-yl,
(29) 1-oxo-1,2-dihydroisoquinolin-6-yl, or
(30) 6-oxo-1,6-dihydropyridin-3-yl.

20. The compound according to claim 1, which is a compound of Formula II:

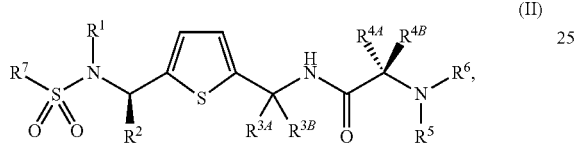

or a pharmaceutically acceptable salt thereof.

21. The compound according to claim 20, or a pharmaceutically acceptable salt thereof, which is a compound of formula III:

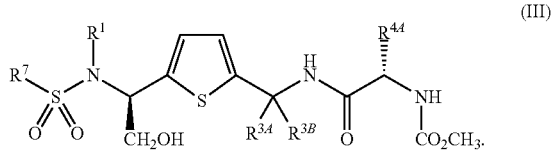

22. A compound which is:
N-[(5-{2-hydroxy-1-[(3-methylbutyl)(phenylsulfonyl)amino]ethyl}thiophen-3-yl)methyl]-Nα-(methoxycarbonyl)-β-phenyl-L-phenylalaninamide;
N-[(2-{2-hydroxy-1-[(3-methylbutyl)(phenylsulfonyl)amino]ethyl}-1,3-thiazol-5-yl)methyl]-Nα-(methoxycarbonyl)-β-phenyl-L-phenylalaninamide;
N-[(5-{2-hydroxy-1-[(3-methylbutyl)(phenylsulfonyl)amino]ethyl}-1,3-thiazol-2-yl)methyl]-Nα-(methoxycarbonyl)-β-phenyl-L-phenylalaninamide;
N-[(5-{2-hydroxy-1-[(3-methylbutyl)(phenylsulfonyl)amino]ethyl}thiophen-2-yl)methyl]-Nα-(methoxycarbonyl)-β-phenyl-L-phenylalaninamide;
N-[(5-{2-hydroxy-1-[{[4-(hydroxymethyl)phenyl]sulfonyl}(3-methylbutyl)amino]ethyl}thiophen-2-yl)methyl]-Nα-(methoxycarbonyl)-β-phenyl-L-phenylalaninamide;
N-[(4-{2-hydroxy-1-[(3-methylbutyl)(phenylsulfonyl)amino]ethyl}thiophen-2-yl)methyl]-Nα-(methoxycarbonyl)-β-phenyl-L-phenylalaninamide;
N-[1-(5-{2-hydroxy-1-[(3-methylbutyl)(phenylsulfonyl)amino]ethyl}thiophen-2-yl)ethyl]-Nα-(methoxycarbonyl)-β-phenyl-L-phenylalaninamide;
N-[1-(5-{2-hydroxy-1-[{[4-(hydroxymethyl)phenyl]sulfonyl}(3-methylbutyl)amino]ethyl}thiophen-2-yl)ethyl]-Nα-(methoxycarbonyl)-β-phenyl-L-phenylalaninamide;
N-[1-(5-{2-hydroxy-1-[{[4-(hydroxymethyl)phenyl]sulfonyl}(3-methylbutyl)amino]ethyl}thiophen-2-yl)propyl]-Nα-(methoxycarbonyl)-β-phenyl-L-phenylalaninamide;
N-({5-[(1R)-1-{[(4-aminophenyl)sulfonyl](2-methylpropyl)amino}-2-hydroxyethyl]thiophen-2-yl}methyl)-Nα-(methoxycarbonyl)-β-phenyl-L-phenylalaninamide;
N-({5-[(1R)-1-{[(4-aminophenyl)sulfonyl][(3,3-difluorocyclobutyl)methyl]amino}-2-hydroxyethyl]thiophen-2-yl}methyl)-Nα-(methoxycarbonyl)-β-phenyl-L-phenylalaninamide;
N-({5-[(1R)-1-{[(4-aminophenyl)sulfonyl](propan-2-yl)amino}-2-hydroxyethyl]thiophen-2-yl}methyl)-Nα-(methoxycarbonyl)-β-phenyl-L-phenylalaninamide;
N-({5-[(1R)-1-{[(4-aminophenyl)sulfonyl](1H-pyrrolo[2,3-b]pyridin-2-ylmethyl)amino}-2-hydroxyethyl]thiophen-2-yl}methyl)-Nα-(methoxycarbonyl)-β-phenyl-L-phenylalaninamide;
N-[(5-{(1R)-2-hydroxy-1-[{[3-(2-hydroxy-2-methylpropyl)phenyl]sulfonyl}(2-methylpropyl)amino]ethyl}thiophen-2-yl)methyl]-Nα-(methoxycarbonyl)-β-phenyl-L-phenylalaninamide;
N-({5-[(1R)-1-([(3,3-difluorocyclobutyl)methyl]{[3-(2-hydroxy-2-methylpropyl)phenyl]sulfonyl}amino)-2-hydroxyethyl]thiophen-2-yl}methyl)-Nα-(methoxycarbonyl)-β-phenyl-L-phenylalaninamide;
Methyl {(2S)— 1-[({5-[(1R)-1-{[(3,3-difluorocyclobutyl)methyl][(1-oxo-1,2-dihydroisoquinolin-6-yl)sulfonyl]amino}-2-hydroxyethyl]thiophen-2-yl}methyl)amino]-1-oxo-3,3-diphenylpropan-2-yl}carbamate;
Methyl {(2S)— 1-[({5-[(1R)-1-{[(3,3-difluorocyclobutyl)methyl](3,4-dihydro-1H-isochromen-6-ylsulfonyl)amino}-2-hydroxyethyl]thiophen-2-yl}methyl)amino]-1-oxo-3,3-diphenylpropan-2-yl}carbamate;
N-({5-[(1R)-1-{[(4-aminophenyl)sulfonyl][(4-methyl-1,2,5-oxadiazol-3-yl)methyl]amino}-2-hydroxyethyl]thiophen-2-yl}methyl)-Nα-(methoxycarbonyl)-β-phenyl-L-phenylalaninamide;
N-({5-[(1R)-1-{[(4-aminophenyl)sulfonyl](1,2,5-oxadiazol-3-ylmethyl)amino}-2-hydroxyethyl]thiophen-2-yl}methyl)-Nα-(methoxycarbonyl)-β-phenyl-L-phenylalaninamide;
N-({5-[(1R)-1-{[(4-aminophenyl)sulfonyl](1,2,5-oxadiazol-3-ylmethyl)amino}-2-hydroxyethyl]thiophen-2-yl}methyl)-Nα-(methoxycarbonyl)-β-phenyl-L-phenylalaninamide;
N-[(5-{1-[(1,3-benzothiazol-5-ylsulfonyl)(propan-2-yl)amino]-2-hydroxyethyl}thiophen-2-yl)methyl]-Nα-(methoxycarbonyl)-β-phenyl-L-phenylalaninamide;
N-[(5-{(1R)-1-[(1,3-benzothiazol-6-ylsulfonyl)(2-methylpropyl)amino]-2-hydroxyethyl}thiophen-2-yl)methyl]-Nα-(methoxycarbonyl)-β-phenyl-L-phenylalaninamide;
N-[(5-{(1S)-1-[(1,3-benzothiazol-6-ylsulfonyl)(2-methylpropyl)amino]-2-hydroxyethyl}thiophen-2-yl)methyl]-Nα-(methoxycarbonyl)-β-phenyl-L-phenylalaninamide;
(+/−) N-[(5-{1-[(1,3-benzothiazol-6-ylsulfonyl)(1H-indol-3-ylmethyl)amino]-2-hydroxyethyl}thiophen-2-yl)methyl]-Nα-(methoxycarbonyl)-β-phenyl-L-phenylalaninamide;

N-[(5-{(1R)-1-[(1,3-benzothiazol-6-ylsulfonyl)(1H-indol-3-ylmethyl)amino]-2-hydroxyethyl}thiophen-2-yl)methyl]-Nα-(methoxycarbonyl)-β-phenyl-L-phenylalaninamide;

N-{[5-(1-{(1,3-benzothiazol-6-ylsulfonyl)[(2-methoxypyridin-3-yl)methyl]amino}-2-hydroxyethyl)thiophen-2-yl]methyl}-Nα-(methoxycarbonyl)-β-phenyl-L-phenylalaninamide;

(+/−) N-{[5-(1-{(1,3-benzothiazol-6-ylsulfonyl)[(2-methoxypyridin-4-yl)methyl]amino}-2-hydroxyethyl)thiophen-2-yl]methyl}-Nα-(methoxycarbonyl)-β-phenyl-L-phenylalaninamide;

N-({5-[(1R)-1-{(1,3-benzothiazol-6-ylsulfonyl)[(2-methoxypyridin-4-yl)methyl]amino}-2-hydroxyethyl]thiophen-2-yl}methyl)-Nα-(methoxycarbonyl)-β-phenyl-L-phenylalaninamide;

N-({5-[(1S)-1-{(1,3-benzothiazol-6-ylsulfonyl)[(2-methoxypyridin-4-yl)methyl]amino}-2-hydroxyethyl]thiophen-2-yl}methyl)-Nα-(methoxycarbonyl)-β-phenyl-L-phenylalaninamide;

N-[(5-{1-[(1,3-benzothiazol-6-ylsulfonyl){[1-(dimethylsulfamoyl)-1H-pyrazol-4-yl]methyl}amino]-2-hydroxyethyl}thiophen-2-yl)methyl]-Nα-(methoxycarbonyl)-β-phenyl-L-phenylalaninamide;

(+/−) N-[(5-{1-[(1,3-benzothiazol-6-ylsulfonyl)(1H-pyrazol-4-ylmethyl)amino]-2-hydroxyethyl}thiophen-2-yl)methyl]-Nα-(methoxycarbonyl)-β-phenyl-L-phenylalaninamide;

N-[(5-{(1R)-1-[(1,3-benzothiazol-6-ylsulfonyl)(1H-pyrazol-4-ylmethyl)amino]-2-hydroxyethyl}thiophen-2-yl)methyl]-Nα-(methoxycarbonyl)-β-phenyl-L-phenylalaninamide;

N-[(5-{(1S)-1-[(1,3-benzothiazol-6-ylsulfonyl)(1H-pyrazol-4-ylmethyl)amino]-2-hydroxyethyl}thiophen-2-yl)methyl]-Nα-(methoxycarbonyl)-β-phenyl-L-phenylalaninamide;

N-[(5-{1-[(1,3-benzothiazol-6-ylsulfonyl)(1H-pyrrolo[2,3-b]pyridin-2-ylmethyl)amino]-2-hydroxyethyl}thiophen-2-yl)methyl]-Nα-(methoxycarbonyl)-β-phenyl-L-phenylalaninamide;

N-[(5-{(1R)-1-[(1,3-benzothiazol-6-ylsulfonyl)(1H-pyrrolo[2,3-b]pyridin-2-ylmethyl)amino]-2-hydroxyethyl}thiophen-2-yl)methyl]-Nα-(methoxycarbonyl)-β-phenyl-L-phenylalaninamide;

(+/−) N-({5-[(1R)-1-{[(3,3-difluorocyclobutyl)methyl][(1-hydroxy-2,3-dihydro-1H-inden-5-yl)sulfonyl]amino}-2-hydroxyethyl]thiophen-2-yl}methyl)-Nα-(methoxycarbonyl)-β-phenyl-L-phenylalaninamide;

N-({5-[(1R)-1-{[(3,3-difluorocyclobutyl)methyl][(1-hydroxy-2,3-dihydro-1H-inden-5-yl)sulfonyl]amino}-2-hydroxyethyl]thiophen-2-yl}methyl)-Nα-(methoxycarbonyl)-β-phenyl-L-phenylalaninamide;

N-({5-[(1R)-1-{[(3,3-difluorocyclobutyl)methyl][(3-hydroxy-2,3-dihydro-1H-inden-5-yl)sulfonyl]amino}-2-hydroxyethyl]thiophen-2-yl}methyl)-Nα-(methoxycarbonyl)-β-phenyl-L-phenylalaninamide;

N-({5-[(1R)-1-{[(3,3-difluorocyclobutyl)methyl]({4-[(1R)-2,2,2-trifluoro-1-hydroxyethyl]phenyl}sulfonyl)amino}-2-hydroxyethyl]thiophen-2-yl}methyl)-Nα-(methoxycarbonyl)-β-phenyl-L-phenylalaninamide;

N-({5-[(1R)-1-([(3,3-difluorocyclobutyl)methyl]{[3-(pyridin-2-ylcarbonyl)phenyl]sulfonyl}amino)-2-hydroxyethyl]thiophen-2-yl}methyl)-Nα-(methoxycarbonyl)-β-phenyl-L-phenylalaninamide;

N-({5-[(1R)-1-{[(3,3-difluorocyclobutyl)methyl](1H-indol-5-ylsulfonyl)amino}-2-hydroxyethyl]thiophen-2-yl}methyl)-Nα-(methoxycarbonyl)-β-phenyl-L-phenylalaninamide;

N-({5-[(1R)-1-([(3,3-difluorocyclobutyl)methyl]{[3-(pyridin-2-ylmethyl)phenyl]sulfonyl}amino)-2-hydroxyethyl]thiophen-2-yl}methyl)-Nα-(methoxycarbonyl)-β-phenyl-L-phenylalaninamide;

N-({5-[(1R)-1-{[(4-amino-3-fluorophenyl)sulfonyl][(3,3-difluorocyclobutyl)methyl]amino}-2-hydroxyethyl]thiophen-2-yl}methyl)-Nα-(methoxycarbonyl)-β-phenyl-L-phenylalaninamide;

N-[(1S)-1-{5-[(1R)-1-{[(4-aminophenyl)sulfonyl](3,3-dimethylbutyl)amino}-2-hydroxyethyl]thiophen-2-yl}-2,2,2-trifluoroethyl]-Nα-(methoxycarbonyl)-β-phenyl-L-phenylalaninamide;

N-[(1S)-1-(5-{(1R)-1-[(3,3-dimethylbutyl)(1H-indazol-5-ylsulfonyl)amino]-2-hydroxyethyl}thiophen-2-yl)-2,2,2-trifluoroethyl]-Nα-(methoxycarbonyl)-β-phenyl-L-phenylalaninamide;

N-[(1S)-1-(5-{(1R)-1-[(3,3-dimethylbutyl)(1H-indol-6-ylsulfonyl)amino]-2-hydroxyethyl}thiophen-2-yl)-2,2,2-trifluoroethyl]-Nα-(methoxycarbonyl)-β-phenyl-L-phenylalaninamide;

N-[(1S)-1-{5-[(1R)-1-{[(4-aminophenyl)sulfonyl][(1,1,1,3,3,3-$^2H_6$)propan-2-yl]amino}-2-hydroxyethyl]thiophen-2-yl}-2,2,2-trifluoroethyl]-Nα-(methoxycarbonyl)-β-phenyl-L-phenylalaninamide;

N-[(1S)-1-{5-[(1R)-1-{[(5-chlorothiophen-2-yl)sulfonyl](propan-2-yl)amino}-2-hydroxyethyl]thiophen-2-yl}-2,2,2-trifluoroethyl]-Nα-(methoxycarbonyl)-β-phenyl-L-phenylalaninamide;

(βS)—N-[(1S)-1-{5-[(1R)-1-{[(4-aminophenyl)sulfonyl](propan-2-yl)amino}-2-hydroxyethyl]thiophen-2-yl}-2,2,2-trifluoroethyl]-Nα-(methoxycarbonyl)-β-1H-pyrrolo[2,3-b]pyridin-3-yl-L-phenylalaninamide;

N-[(1S)-1-{5-[(1R)-1-{[(5-aminothiophen-2-yl)sulfonyl](propan-2-yl)amino}-2-hydroxyethyl]thiophen-2-yl}-2,2,2-trifluoroethyl]-Nα-(methoxycarbonyl)-β-phenyl-L-phenylalaninamide;

N-[(1S)-1-(5-{(1R)-1-[(3,3-dimethylbutyl)(imidazo[1,2-a]pyridin-7-ylsulfonyl)amino]-2-hydroxyethyl}thiophen-2-yl)-2,2,2-trifluoroethyl]-Nα-(methoxycarbonyl)-β-phenyl-L-phenylalaninamide;

N-[(1S)-1-(5-{(1R)-1-{[[3,5-difluoro-4-(hydroxymethyl)phenyl]sulfonyl](3,3-dimethylbutyl)amino}-2-hydroxyethyl}thiophen-2-yl)-2,2,2-trifluoroethyl]-Nα-(methoxycarbonyl)-β-phenyl-L-phenylalaninamide;

N-[(1S)-1-(5-{(1R)-1-[(3,3-dimethylbutyl){[4-(hydroxymethyl)phenyl]sulfonyl}amino]-2-hydroxyethyl}thiophen-2-yl)-2,2,2-trifluoroethyl]-Nα-(methoxycarbonyl)-β-phenyl-L-phenylalaninamide;

N-[(1S)-1-{5-[(1R)-1-{[(4-aminothiophen-2-yl)sulfonyl](propan-2-yl)amino}-2-hydroxyethyl]thiophen-2-yl}-2,2,2-trifluoroethyl]-Nα-(methoxycarbonyl)-β-phenyl-L-phenylalaninamide;

N-[(1S)-1-(5-{(1R)-1-[(3,3-dimethylbutyl)(1H-indol-2-ylsulfonyl)amino]-2-hydroxyethyl}thiophen-2-yl)-2,2,2-trifluoroethyl]-Nα-(methoxycarbonyl)-β-phenyl-L-phenylalaninamide;

N-[(1S)-1-(5-{(1R)-1-[(3,3-dimethylbutyl){[4-(hydroxymethyl)-3-(trifluoromethyl)phenyl]sulfonyl}amino]-2-hydroxyethyl}thiophen-2-yl)-2,2,2-trifluoroethyl]-Nα-(methoxycarbonyl)-β-phenyl-L-phenylalaninamide;

N-[(1S)-1-{5-[(1R)-1-{[(5-aminopyridin-2-yl)sulfonyl](3,3-dimethylbutyl)amino}-2-hydroxyethyl]thiophen- 2-yl}-2,2,2-trifluoroethyl]-Nα-(methoxycarbonyl)-β-phenyl-L-phenylalaninamide;

N-[(1S)-1-(5-{(1R)-1-[(1,2,3-benzothiadiazol-6-ylsulfonyl)(3,3-dimethylbutyl)amino]-2-hydroxyethyl}thiophen-2-yl)-2,2,2-trifluoroethyl]-Nα-(methoxycarbonyl)-β-phenyl-L-phenylalaninamide;

N-[(1S)-1-(5-{(1R)-1-[(3,3-dimethylbutyl)(1H-indol-4-ylsulfonyl)amino]-2-hydroxyethyl}thiophen-2-yl)-2,2,2-trifluoroethyl]-Nα-(methoxycarbonyl)-β-phenyl-L-phenylalaninamide;

N-[(1S)-1-{5-[(1R)-1-{[(4-aminophenyl)sulfonyl](2-methylpropyl)amino}-2-hydroxyethyl]thiophen-2-yl}-2,2,2-trifluoroethyl]-Nα-(methoxycarbonyl)-β-phenyl-L-phenylalaninamide;

N-[(1R)-1-{5-[(1R)-1-{[(4-aminophenyl)sulfonyl](2-methylpropyl)amino}-2-hydroxyethyl]thiophen-2-yl}-2,2,2-trifluoroethyl]-Nα-(methoxycarbonyl)-β-phenyl-L-phenylalaninamide;

N-[(1S)-1-{5-[(1R)-1-{[(4-aminophenyl)sulfonyl](ethyl)amino}-2-hydroxyethyl]thiophen-2-yl}-2,2,2-trifluoroethyl]-Nα-(methoxycarbonyl)-β-phenyl-L-phenylalaninamide;

N—[(S)-{5-[(1R)-1-{[(4-aminophenyl)sulfonyl](2-methylpropyl)amino}-2-hydroxyethyl]thiophen-2-yl}(cyclopropyl)methyl]-Nα-(methoxycarbonyl)-β-phenyl-L-phenylalaninamide;

N-[2-(5-{2-hydroxy-1-[(3-methylbutyl)(phenylsulfonyl)amino]ethyl}thiophen-2-yl)propan-2-yl]-Nα-(methoxycarbonyl)-β-phenyl-L-phenylalaninamide;

Nα-(methoxycarbonyl)-β-phenyl-N-[(1S)-2,2,2-trifluoro-1-(5-{(1R)-2-hydroxy-1-[{[4-(hydroxymethyl)phenyl]sulfonyl}(propan-2-yl)amino]ethyl}thiophen-2-yl)ethyl]-L-phenylalaninamide;

N-({5-[(1R)-1-([(3,3-difluorocyclobutyl)methyl][4-(1-hydroxyethyl)phenyl]sulfonyl}amino)-2-hydroxyethyl]thiophen-2-yl}methyl)-Nα-(methoxycarbonyl)-β-phenyl-L-phenylalaninamide;

N-({5-[(1R)-1-{[(4-acetylphenyl)sulfonyl][(3,3-difluorocyclobutyl)methyl]amino}-2-hydroxyethyl]thiophen-2-yl}methyl)-Nα-(methoxycarbonyl)-β-phenyl-L-phenylalaninamide;

N-{(1S)-1-[5-(1-{(3,3-dimethylbutyl)[(6-methoxypyridin-3-yl)sulfonyl]amino}-2-hydroxyethyl)thiophen-2-yl]-2,2,2-trifluoroethyl}-Nα-(methoxycarbonyl)-β-phenyl-L-phenylalaninamide;

N-[(1S)-1-{5-[(1R)-1-{(3,3-dimethylbutyl)[(6-oxo-1,6-dihydropyridin-3-yl)sulfonyl]amino}-2-hydroxyethyl]thiophen-2-yl}-2,2,2-trifluoroethyl]-Nα-(methoxycarbonyl)-β-phenyl-L-phenylalaninamide;

N-[(1S)-1-(5-{1-[(3,3-dimethylbutyl)({4-[(methoxycarbonyl)amino]phenyl}sulfonyl)amino]-2-hydroxyethyl}thiophen-2-yl)-2,2,2-trifluoroethyl]-Nα-(methoxycarbonyl)-β-phenyl-L-phenylalaninamide;

N-[(1S)-1-(5-{(1R)-1-[(3,3-dimethylbutyl)(imidazo[1,2-c]pyridin-6-ylsulfonyl)amino]-2-hydroxyethyl}thiophen-2-yl)-2,2,2-trifluoroethyl]-Nα-(methoxycarbonyl)-β-phenyl-L-phenylalaninamide;

N-[(1S)-1-{5-[(1R)-1-{[(3-chloro-3a,7a-dihydro-1H-indol-6-yl)sulfonyl]-(3,3-dimethylbutyl)amino}-2-hydroxyethyl]thiophen-2-yl}-2,2,2-trifluoroethyl]-Nα-(methoxycarbonyl)-β-phenyl-L-phenylalaninamide;

Methyl [(2S)-1-{[(1S)-1-(5-{(1R)-1-[(3,3-dimethylbutyl)(quinolin-6-ylsulfonyl)amino]-2-hydroxyethyl}thiophen-2-yl)-2,2,2-trifluoroethyl]amino}-1-oxo-3,3-diphenylpropan-2-yl]carbamate;

N-[(1S)-1-(5-{(1R)-1-[(1H-benzimidazol-6-ylsulfonyl)(3,3-dimethylbutyl)amino]-2-hydroxyethyl}thiophen-2-yl)-2,2,2-trifluoroethyl]-Nα-(methoxycarbonyl)-β-phenyl-L-phenylalaninamide;

N-[(1S)-1-{5-[(1R)-1-{[(4-aminophenyl)sulfonyl](propan-2-yl)amino}-2-hydroxyethyl]thiophen-2-yl}ethyl]-Nα-(methoxycarbonyl)-β-phenyl-L-phenylalaninamide;

N-[(1S)-1-{5-[(1R)-1-{[(4-aminophenyl)sulfonyl](2-methylpropyl)amino}-2-hydroxyethyl]thiophen-2-yl}ethyl]-Nα-(methoxycarbonyl)-β-phenyl-L-phenylalaninamide;

N-[(1S)-1-{5-[(1R)-1-{[(4-aminophenyl)sulfonyl](propan-2-yl)amino}-2-hydroxyethyl]thiophen-2-yl}-2,2,2-trifluoroethyl]-Nα-(methoxycarbonyl)-β-phenyl-L-phenylalaninamide;

Nα-(methoxycarbonyl)-β-phenyl-N-[(1S)-2,2,2-trifluoro-1-(5-{(1R)-2-hydroxy-1-[(1H-indol-5-ylsulfonyl)(propan-2-yl)amino]ethyl}thiophen-2-yl)ethyl]-L-phenylalaninamide;

Nα-(methoxycarbonyl)-β-phenyl-N-[(1S)-2,2,2-trifluoro-1-(5-{(1R)-2-hydroxy-1-[(1H-indol-6-ylsulfonyl)(propan-2-yl)amino]ethyl}thiophen-2-yl)ethyl]-L-phenylalaninamide;

N-[(1S)-1-{5-[(1R)-1-{[(4-amino-3-fluorophenyl)sulfonyl](propan-2-yl)amino}-2-hydroxyethyl]thiophen-2-yl}-2,2,2-trifluoroethyl]-Nα-(methoxycarbonyl)-β-phenyl-L-phenylalaninamide;

Nα-(methoxycarbonyl)-β-phenyl-N-[(1S)-2,2,2-trifluoro-1-(5-{(1R)-2-hydroxy-1-[(1H-indazol-6-ylsulfonyl)(propan-2-yl)amino]ethyl}thiophen-2-yl)ethyl]-L-phenylalaninamide;

N-[(1S)-1-{5-[(1R)-1-{[(4-amino-3-chlorophenyl)sulfonyl](propan-2-yl)amino}-2-hydroxyethyl]thiophen-2-yl}-2,2,2-trifluoroethyl]-Nα-(methoxycarbonyl)-β-phenyl-L-phenylalaninamide;

N-[(1S)-1-{5-[(1R)-1-{[(4-aminophenyl)sulfonyl](3-methylbutyl)amino}-2-hydroxyethyl]thiophen-2-yl}-2,2,2-trifluoroethyl]-Nα-(methoxycarbonyl)-β-phenyl-L-phenylalaninamide;

N-[(1S)-1-{5-[(1R)-1-{[(4-aminophenyl)sulfonyl][(3,3-difluorocyclobutyl)methyl]amino}-2-hydroxyethyl]thiophen-2-yl}-2,2,2-trifluoroethyl]-Nα-(methoxycarbonyl)-β-phenyl-L-phenylalaninamide;

N-[(1S)-1-{5-[(1R)-1-{[(4-aminophenyl)sulfonyl](3,3,3-trifluoropropyl)amino}-2-hydroxyethyl]thiophen-2-yl}-2,2,2-trifluoroethyl]-Nα-(methoxycarbonyl)-β-phenyl-L-phenylalaninamide;

N-[(1S)-1-{5-[(1R)-1-{[(4-aminophenyl)sulfonyl](2-cyclopropylethyl)amino}-2-hydroxyethyl]thiophen-2-yl}-2,2,2-trifluoroethyl]-Nα-(methoxycarbonyl)-β-phenyl-L-phenylalaninamide;

N-[(1S)-1-{5-[(1R)-1-{[(4-aminophenyl)sulfonyl]amino}-2-hydroxyethyl]thiophen-2-yl}-2,2,2-trifluoroethyl]-Nα-(methoxycarbonyl)-β-phenyl-L-phenylalaninamide;

N-[(1S)-1-{5-[(1R)-1-{[(4-aminophenyl)sulfonyl](butyl)amino}-2-hydroxyethyl]thiophen-2-yl}-2,2,2-trifluoroethyl]-Nα-(methoxycarbonyl)-β-phenyl-L-phenylalaninamide;

N-[(1S)-1-{5-[(1R)-1-{[(4-aminophenyl)sulfonyl](2-phenylethyl)amino}-2-hydroxyethyl]thiophen-2-yl}-2,2,2-trifluoroethyl]-Nα-(methoxycarbonyl)-β-phenyl-L-phenylalaninamide;

N-[(1S)-1-(5-{(1R)-1-[(3,3-dimethylbutyl) {[4-(1,3-oxazol-5-yl)phenyl]sulfonyl}amino]-2-hydroxyethyl}thiophen-2-yl)-2,2,2-trifluoroethyl]-Nα-(methoxycarbonyl)-β-phenyl-L-phenylalaninamide;

N-[(1S)-1-(5-{(1R)-1-[(1,3-benzothiazol-5-ylsulfonyl)(3,3-dimethylbutyl)amino]-2-hydroxyethyl}thiophen-2-yl)-2,2,2-trifluoroethyl]-Nα-(methoxycarbonyl)-β-phenyl-L-phenylalaninamide;

N-[(1S)-1-(5-{(1R)-1-[(3,3-dimethylbutyl){[4-(1-methyl-1H-pyrazol-3-yl)phenyl]sulfonyl}amino]-2-hydroxyethyl}thiophen-2-yl)-2,2,2-trifluoroethyl]-Nα-(methoxycarbonyl)-β-phenyl-L-phenylalaninamide;

N-[(1S)-1-(5-{(1R)-1-[(3,3-dimethylbutyl)(1H-indazol-5-ylsulfonyl)amino]-2-hydroxyethyl}thiophen-2-yl)-2,2,2-trifluoroethyl]-Nα-(methoxycarbonyl)-β-phenyl-L-phenylalaninamide;

N-[(1S)-1-(5-{(1R)-1-[(3,3-dimethylbutyl)(1H-indol-6-ylsulfonyl)amino]-2-hydroxyethyl}thiophen-2-yl)-2,2,2-trifluoroethyl]-Nα-(methoxycarbonyl)-β-phenyl-L-phenylalaninamide;

N-[(1S)-1-(5-{(1R)-1-[(1-benzothiophen-2-ylsulfonyl)(3,3-dimethylbutyl)amino]-2-hydroxyethyl}thiophen-2-yl)-2,2,2-trifluoroethyl]-Nα-(methoxycarbonyl)-β-phenyl-L-phenylalaninamide;

N-[(1S)-1-(5-{(1R)-1-[(1,3-benzoxazol-5-ylsulfonyl)(3,3-dimethylbutyl)amino]-2-hydroxyethyl}thiophen-2-yl)-2,2,2-trifluoroethyl]-Nα-(methoxycarbonyl)-β-phenyl-L-phenylalaninamide;

N-[(1S)-1-{5-[(1R)-1-{[(4-amino-3-fluorophenyl)sulfonyl](3,3-dimethylbutyl)amino}-2-hydroxyethyl]thiophen-2-yl}-2,2,2-trifluoroethyl]-Nα-(methoxycarbonyl)-β-phenyl-L-phenylalaninamide;

N-[(1S)-1-{5-[(1R)-1-{[(4-amino-2-fluorophenyl)sulfonyl](3,3-dimethylbutyl)amino}-2-hydroxyethyl]thiophen-2-yl}-2,2,2-trifluoroethyl]-Nα-(methoxycarbonyl)-β-phenyl-L-phenylalaninamide;

N-[(1S)-1-(5-{(1R)-1-[(3,3-dimethylbutyl)(imidazo[1,2-a]pyrazin-6-ylsulfonyl)amino]-2-hydroxyethyl}thiophen-2-yl)-2,2,2-trifluoroethyl]-Nα-(methoxycarbonyl)-β-phenyl-L-phenylalaninamide;

N-[(1S)-1-(5-{(1R)-1-[(1,3-benzothiazol-6-ylsulfonyl)(3,3-dimethylbutyl)amino]-2-hydroxyethyl}thiophen-2-yl)-2,2,2-trifluoroethyl]-Nα-(methoxycarbonyl)-β-phenyl-L-phenylalaninamide;

N-[(1S)-1-(5-{(1R)-1-[(1H-benzotriazol-6-ylsulfonyl)(3,3-dimethylbutyl)amino]-2-hydroxyethyl}thiophen-2-yl)-2,2,2-trifluoroethyl]-Nα-(methoxycarbonyl)-β-phenyl-L-phenylalaninamide;

N-[(1S)-1-(5-{(1R)-1-[(3,3-dimethylbutyl)(1H-indazol-6-ylsulfonyl)amino]-2-hydroxyethyl}thiophen-2-yl)-2,2,2-trifluoroethyl]-Nα-(methoxycarbonyl)-β-phenyl-L-phenylalaninamide;

N-[(1S)-1-(5-{(1R)-1-[(3,3-dimethylbutyl)(1H-indol-5-ylsulfonyl)amino]-2-hydroxyethyl}thiophen-2-yl)-2,2,2-trifluoroethyl]-Nα-(methoxycarbonyl)-β-phenyl-L-phenylalaninamide;

N-[(1S)-1-(5-{(1R)-1-[(1,3-benzothiazol-6-ylsulfonyl)(3,3,3-trifluoropropyl)amino]-2-hydroxyethyl}thiophen-2-yl)-2,2,2-trifluoroethyl]-Nα-(methoxycarbonyl)-β-phenyl-L-phenylalaninamide;

N-[(1S)-1-(5-{(1R)-1-[(1,3-benzothiazol-6-ylsulfonyl)(4,4,4-trifluorobutyl)amino]-2-hydroxyethyl}thiophen-2-yl)-2,2,2-trifluoroethyl]-Nα-(methoxycarbonyl)-β-phenyl-L-phenylalaninamide;

N-[(1S)-1-{5-[(1R)-1-{(1,3-benzothiazol-6-ylsulfonyl)[(2-$^2$H)propan-2-yl]amino}-2-hydroxyethyl]thiophen-2-yl}-2,2,2-trifluoroethyl]-Nα-(methoxycarbonyl)-β-phenyl-L-phenylalaninamide;

Nα-(methoxycarbonyl)-β-phenyl-N-[(1S)-2,2,2-trifluoro-1-{5-[(1R)-2-hydroxy-1-{(1H-indazol-5-ylsulfonyl)[(2-$^2$H)propan-2-yl]amino}ethyl]thiophen-2-yl}ethyl]-L-phenylalaninamide;

N-[(1S)-1-{5-[(1R)-1-{[(4-amino-2-fluorophenyl)sulfonyl][(2-$^2$H)propan-2-yl]amino}-2-hydroxyethyl]thiophen-2-yl}-2,2,2-trifluoroethyl]-Nα-(methoxycarbonyl)-β-phenyl-L-phenylalaninamide;

methyl [(1S)-2-{[(1)-1-(5-{(1R)-1-[{[4-(aminocarbonyl)phenyl]sulfonyl}(isopropyl)amino]-2-hydroxyethyl}-2-thienyl)-2,2,2-trifluoroethyl]amino}-1-(diphenylmethyl)-2-oxoethyl]carbamate;

N-((1S)-1-{5-[(1R)-1-((3,3-dimethylbutyl){[4-(2H-tetrazol-2-yl)phenyl]sulfonyl}amino)-2-hydroxyethyl]-2-thienyl}-2,2,2-trifluoroethyl)-Nα-(methoxycarbonyl)-β-phenyl-L-phenylalaninamide;

N-((1S)-1-{5-[(1R)-1-((3,3-dimethylbutyl){[4-(1H-tetrazol-1-yl)phenyl]sulfonyl}amino)-2-hydroxyethyl]-2-thienyl}-2,2,2-trifluoroethyl)-Nα-(methoxycarbonyl)-β-phenyl-L-phenylalaninamide;

N-{2-[(3S)-3-{[(4-aminophenyl)sulfonyl](2H-triazol-2-yl)amino}-4-hydroxybutyl]phenyl}-Nα-(methoxycarbonyl)-β-phenyl-L-phenylalaninamide;

N-{2-[(3S)-3-{[(4-aminophenyl)sulfonyl][(1H-triazol-1-yl)methyl]amino}-4-hydroxybutyl]phenyl}-Nα-(methoxycarbonyl)-β-phenyl-L-phenylalaninamide;

N-{(1S)-1-[5-((1R)-1-[(3,3-dimethylbutyl)][(4-isoxazol-5-ylphenyl)sulfonyl]amino}-2-hydroxyethyl)-2-thienyl]-2,2,2-trifluoroethyl}-Nα-(methoxycarbonyl)-β-phenyl-L-phenylalaninamide;

N-{(1S)-1-[5-((1R)-1-{(3,3-dimethylbutyl)[4-(1-methyl-1H-pyrazol-4-yl)phenylsulfonyl]amino}-2-hydroxyethyl)-2-thienyl]-2,2,2-trifluoroethyl}-Nα-(methoxycarbonyl)-β-phenyl-L-phenylalaninamide;

N-[(1S)-1-(5-{(1R)-1-[[(4-amino-3-chlorophenyl)sulfonyl](3,3-dimethylbutyl)amino]-2-hydroxyethyl}-2-thienyl)-2,2,2-trifluoroethyl]-Nα-(methoxycarbonyl)-β-phenyl-L-phenylalaninamide;

N-[(1S)-1-(5-{(1R)-1-[[(4-amino-2-chlorophenyl)sulfonyl](3,3-dimethylbutyl)amino]-2-hydroxyethyl}-2-thienyl)-2,2,2-trifluoroethyl]-Nα-(methoxycarbonyl)-β-phenyl-L-phenylalaninamide;

N-[(1S)-1-(5-{(1R)-1-[(3,3-dimethylbutyl)([1,2,4]triazolo[1,5-a]pyridin-6-ylsulfonyl)amino]-2-hydroxyethyl}thiophen-2-yl)-2,2,2-trifluoroethyl]-Nalpha-(methoxycarbonyl)-beta-phenyl-L-phenylalaninamide;

N-[(1S)-1-{5-[(1R)-1-{[(2-chloroimidazo[1,2-a]pyrazin-6-yl)sulfonyl](3,3-dimethylbutyl)amino}-2-hydroxyethyl]thiophen-2-yl}-2,2,2-trifluoroethyl]-Nα-(methoxycarbonyl)-β-phenyl-L-phenylalaninamide;

N-[(1S)-1-(5-{(1R)-1-[(3,3-dimethylbutyl)([1,2,4]triazolo[1,5-a]pyridin-7-ylsulfonyl)amino]-2-hydroxyethyl}thiophen-2-yl)-2,2,2-trifluoroethyl]-Nalpha-(methoxycarbonyl)-beta-phenyl-L-phenylalaninamide;

N-[(1S)-1-(5-{(1R)-1-[(3,3-dimethylbutyl)([1,2,4]triazolo[1,5-a]pyrazin-6-ylsulfonyl)amino]-2-hydroxyethyl}thiophen-2-yl)-2,2,2-trifluoroethyl]-Nalpha-(methoxycarbonyl)-beta-phenyl-L-phenylalaninamide;

N-[(1S)-1-(5-{(1R)-1-[(3,3-dimethylbutyl)(imidazo[1,2-a]pyrazin-6-ylsulfonyl)amino]-2-hydroxyethyl}thiophen-2-yl)-2,2,2-trifluoroethyl]-Nα-(methoxycarbonyl)-β-phenyl-L-phenylalaninamide;

N-[(5-{(1R)-1-[(1,3-benzothiazol-6-ylsulfonyl)(2-methylpropyl)amino]-2-hydroxyethyl}thiophen-2-yl)methyl]-Nα-(methoxycarbonyl)-β-phenyl-L-phenylalaninamide;

N-[1-[[5-[1-(1,3-benzothiazol-6-ylsulfonyl(isobutyl)amino)-2-hydroxy-ethyl]-2-thienyl]methylcarbamoyl]-2-(3-fluoro-4-pyridyl)-2-phenyl-ethyl]benzamide;

N-[1-[[5-[1-(1,3-benzothiazol-6-ylsulfonyl(isobutyl)amino)-2-hydroxy-ethyl]-2-thienyl]methylcarbamoyl]-2-phenyl-2-(4-quinolyl)ethyl]benzamide;

N-[1-[[5-[1-(1,3-benzothiazol-6-ylsulfonyl(isobutyl)amino)-2-hydroxy-ethyl]-2-thienyl]methylcarbamoyl]-2-phenyl-2-(1H-pyrrolo[2,3-b]pyridin-3-yl)ethyl]benzamide;

N-[1-[[5-[1-(1,3-benzothiazol-6-ylsulfonyl(isobutyl)amino)-2-hydroxy-ethyl]-2-thienyl]methylcarbamoyl]-2-(1-methylindol-3-yl)-2-phenyl-ethyl]benzamide;

N-[1-benzhydryl-2-[[5-[1-(1,3-benzothiazol-6-ylsulfonyl(isobutyl)amino)-2-hydroxy-ethyl]-2-thienyl]methylamino]-2-oxo-ethyl]benzamide;

N-[1-[[5-[1-(1,3-benzothiazol-6-ylsulfonyl(isobutyl)amino)-2-hydroxy-ethyl]-2-thienyl]methylcarbamoyl]-2-(8-isoquinolyl)-2-phenyl-ethyl]benzamide;

N-[1-[[5-[1-(1,3-benzothiazol-6-ylsulfonyl(isobutyl)amino)-2-hydroxy-ethyl]-2-thienyl]methylcarbamoyl]-2-phenyl-2-(3-phenyl-1H-pyrazol-4-yl)ethyl]benzamide;

N-[1-[[5-[1-(1,3-benzothiazol-6-ylsulfonyl(isobutyl)amino)-2-hydroxy-ethyl]-2-thienyl]methylcarbamoyl]-2-phenyl-2-(1H-pyrazol-4-yl)ethyl]benzamide;

N-[1-[[5-[1-(1,3-benzothiazol-6-ylsulfonyl(isobutyl)amino)-2-hydroxy-ethyl]-2-thienyl]methylcarbamoyl]-2-(1H-imidazol-5-yl)-2-phenyl-ethyl]benzamide;

N-[1-[[5-[1-(1,3-benzothiazol-6-ylsulfonyl(isobutyl)amino)-2-hydroxy-ethyl]-2-thienyl]methylcarbamoyl]-2-phenyl-2-(5-quinolyl)ethyl]benzamide; or N-[1-[[5-[1-(1,3-benzothiazol-6-ylsulfonyl(isobutyl)amino)-2-hydroxy-ethyl]-2-thienyl]methylcarbamoyl]-2-phenyl-2-(7-quinolyl)ethyl]benzamide;

and pharmaceutically acceptable salts thereof.

23. A pharmaceutical composition comprising an effective amount of a compound according to claim 1 or a pharmaceutically acceptable salt thereof, and a pharmaceutically acceptable carrier.

24. A method for the inhibition of HIV protease, or for the treatment or prophylaxis of infection by HIV or for the treatment, prophylaxis, or delay in the onset of AIDS in a subject in need thereof, which comprises administering to the subject an effective amount of a compound according to claim 1 or a pharmaceutically acceptable salt thereof.

\* \* \* \* \*